(12) United States Patent
Gravestock

(10) Patent No.: US 7,087,629 B2
(45) Date of Patent: *Aug. 8, 2006

(54) HETEROCYCLYLAMINOMETHYL OXAZOLIDINONES AS ANTIBACTERIALS

(75) Inventor: Michael Barry Gravestock, Waltham, MA (US)

(73) Assignee: AstraZeneca AB, Södertälje (SE)

( * ) Notice: Subject to any disclaimer, the term of this patent is extended or adjusted under 35 U.S.C. 154(b) by 297 days.

This patent is subject to a terminal disclaimer.

(21) Appl. No.: 10/382,396

(22) Filed: Mar. 6, 2003

(65) Prior Publication Data

US 2003/0207899 A1    Nov. 6, 2003

Related U.S. Application Data

(63) Continuation of application No. 09/807,113, filed as application No. PCT/GB99/03299 on Oct. 5, 1999, now Pat. No. 6,734,200.

(30) Foreign Application Priority Data

Oct. 9, 1998    (GB) ................................. 9821938.9

(51) Int. Cl.
A61K 31/422 (2006.01)
C07D 413/12 (2006.01)
C07D 417/12 (2006.01)

(52) U.S. Cl. ....................... 514/376; 548/229; 548/231

(58) Field of Classification Search ................ 548/229, 548/231; 514/376
See application file for complete search history.

(56) References Cited

U.S. PATENT DOCUMENTS

| 4,705,799 A | 11/1987 | Gregory |
| 5,792,765 A | 8/1998 | Riedl et al. |
| 6,734,200 B1 * | 5/2004 | Gravestock .................. 514/376 |

FOREIGN PATENT DOCUMENTS

EP    0 127 902 A    12/1984

OTHER PUBLICATIONS

Chemical Abstract; vol. 122, 55826, No. 5, 1995.
Chemical Abstract, vol. 124; 342951, No. 25, 1996.
Society of Toxicologists Annual Meeting, 1996, Abstract No. 564.
M.R. Barcachyn et al., Bioorganic & Med. Chem. Letters, 1996, vol. 6, No. pp. 1009-1014.
D.L. Shinabarger et al, Antimicrobial Agents Chemotehr., 1997, Vo. 41, No. 10, pp. 2132-2136.
D.C. Eustice, J. Antimicrob. Chemother., 1988, Vo. 32, No. 8, pp. 1218-1222.
J.S. Daley et al., J. Antimicrob. Chemother., 1988, vol. 21, No. 6, pp. 721-730.
Interscience Congress of Antimicrobial Agents and Chemotherapy conference abstracts: Sep. 17-20, 1995, Upjohn Oxazolidinone Antibacterial agents.
Interscience Congress of Antimicrobial Agents and Chemotherapy conference abstracts: Sep. 15-18, 1996, 899, C42, F231, F233, F234, C101, F232.
Interscience Congress of Antimicrobial Agents and Chemotherapy conference abstracts: Sep. 28-Oct. 1, 1997, C101, C102, F17-F28.

* cited by examiner

Primary Examiner—Laura L. Stockton

(57) ABSTRACT

Compounds of formula (I)

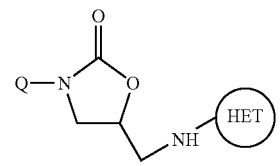

(I)

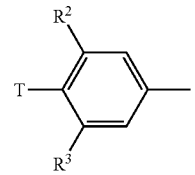

(Q1)

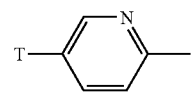

(Q2)

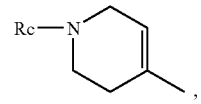

(TC5)

or a pharmaceutically-acceptable salt, or an in-vivo-hydrolysable ester thereof, wherein, for example, HET is an optionally substituted C-linked 5-membered heteroaryl ring containing 2 to 4 heteroatoms independently selected from N, O and S; Q is selected from, for example, Q3 and Q5; $R^2$ and $R^3$ are independently hydrogen or fluoro; T is selected from a range of groups, for example, an N-linked (fully unsaturated) 5-membered heteroaryl ring system or a group of formula (TC5): wherein Rc is, for example, $R^{13}CO$—, $R^{13}SO_2$— or $R^{13}CS$—; wherein $R^{13}$ is, for example, optionally substituted (1–10C)alkyl or $R^{14}C(O)O$ (1–6C)alkyl wherein $R^{14}$ is optionally substituted (1–10C)alkyl; are useful as antibacterial agents; and processes for their manufacture and pharmaceutical compositions containing them are described.

7 Claims, No Drawings

HETEROCYCLYLAMINOMETHYL OXAZOLIDINONES AS ANTIBACTERIALS

This application is a continuation of U.S. patent application Ser. No. 09/807,113, which is the National Stage filing under 35 U.S.C. 371 of International Application No. PCT/GB99/03299, filed Oct. 5, 1999, which claims priority from United Kingdom Application No. 9821938.9, filed Oct. 9, 1998, the specifications of each of which are incorporated by reference herein in their entirety. International Application No. PCT/GB99/03299 was published under PCT Article 21(2) in English.

The present invention relates to antibiotic compounds and in particular to antibiotic compounds containing a substituted oxazolidinone ring. This invention further relates to processes for their preparation, to intermediates useful in their preparation, to their use as therapeutic agents and to pharmaceutical compositions containing them.

The international microbiological community continues to express serious concern that the evolution of antibiotic resistance could result in strains against which currently available antibacterial agents will be ineffective. In general, bacterial pathogens may be classified as either Gram-positive or Gram-negative pathogens. Antibiotic compounds with effective activity against both Gram-positive and Gram-negative pathogens are generally regarded as having a broad spectrum of activity. The compounds of the present invention are regarded primarily as effective against Gram-positive pathogens because of their particularly good activity against such pathogens.

Gram-positive pathogens, for example Staphylococci, Enterococci, Streptococci and mycobacteria, are particularly important because of the development of resistant strains which are both difficult to treat and difficult to eradicate from the hospital environment once established. Examples of such strains are methicillin resistant *staphylococcus* (MRSA), methicillin resistant coagulase negative staphylococci (MRCNS), penicillin resistant *Streptococcus pneumoniae* and multiply resistant *Enterococcus faecium*.

The major clinically effective antibiotic for treatment of such resistant Gram-positive pathogens is vancomycin. Vancomycin is a glycopeptide and is associated with nephrotoxicity and ototoxicity. Furthermore, and most importantly, antibacterial resistance to vancomycin and other glycopeptides is also appearing. This resistance is increasing at a steady rate rendering these agents less and less effective in the treatment of Gram-positive pathogens.

Certain antibacterial compounds containing an oxazolidinone ring have been described in the art (for example, Walter A. Gregory et al in J. Med. Chem. 1990, 33, 2569–2578 and Chung-Ho Park et al in J. Med. Chem. 1992, 35, 1156–1165). Such antibacterial oxazolidinone compounds with a 5-methylacetamide sidechain may be subject to mammalian peptidase metabolism. Furthermore, bacterial resistance to known antibacterial agents may develop, for example, by (i) the evolution of active binding sites in the bacteria rendering a previously active pharmacophore less effective or redundant, and/or (ii) the evolution of means to chemically deactivate a given pharmacophore. Therefore, there remains an ongoing need to find new antibacterial agents with a favourable pharmacological profile, in particular for compounds containing new pharmacophores.

We have discovered a class of antibiotic compounds containing a new class of substituted oxazolidinone ring which has useful activity against Gram-positive pathogens including MRSA and MRCNS and, in particular, against various strains exhibiting resistance to vancomycin and against *E. faecium* strains resistant to both aminoglycosides and clinically used β-lactams.

Accordingly the present invention provides a compound of the formula (I), or a pharmaceutically-acceptable salt, or an in-vivo-hydrolysable ester thereof,

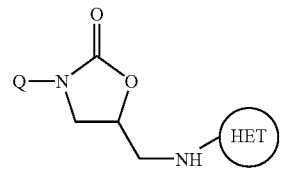

(I)

wherein

HET is a C-linked 5-membered heteroaryl ring containing 2 to 4 heteroatoms independently selected from N, O and S, which ring is optionally substituted on an available carbon atom by 1 or 2 substituents independently selected from (1–4C)alkyl, amino, (1–4C)alkylamino, (1–4C)alkoxy, (1–4C)alkoxycarbonyl and halogen, and/or on an available nitrogen atom (provided that the ring is not thereby quaternised) by (1–4C)alkyl; or HET is a C-linked 6-membered heteroaryl ring containing 2 or 3 nitrogen heteroatoms, which ring is optionally substituted on any available C atom by 1, 2 or 3 substituents independently selected from (1–4C)alkyl, amino, (1–4C) alkylamino, (1–4C)alkoxy, (1–4C)alkoxycarbonyl and halogen;

Q is selected from Q1 to Q9:—

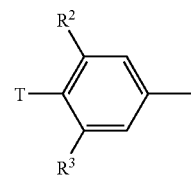

Q1

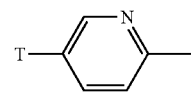

Q2

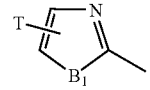

Q3

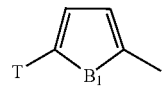

Q4

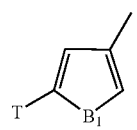

Q5

-continued

Q6

Q7

Q8

Q9 wherein $R^2$ and $R^3$ are independently hydrogen or fluoro;

wherein $A_1$ is carbon or nitrogen; $B_1$ is O or S (or, in Q9 only, NH); $X_q$ is O, S or N—$R^1$ (wherein $R^1$ is hydrogen, (1–4C) alkyl or hydroxy-(1–4C)alkyl); and wherein in Q7 each $A_1$ is independently selected from carbon or nitrogen, with a maximum of 2 nitrogen heteroatoms in the 6-membered ring, and Q7 is linked to T via any of the $A_1$ atoms (when $A_1$ is carbon), and linked in the 5-membered ring via the specified carbon atom, or via $A_1$ when $A_1$ is carbon; Q8 is linked to T via either of the specified carbon atoms in the 5-membered ring, and linked in the benzo-ring via either of the two specified carbon atoms on either side of the linking bond shown; and Q9 is linked via either of the two specified carbon atoms on either side of the linking bond shown;

wherein T is selected from the groups in (TA) to (TD) below (wherein AR1, AR2, AR2a, AR2b, AR3, AR3a, AR3b, AR4, AR4a, CY1 and CY2 are defined hereinbelow);

(TA) T is selected from the following groups:—

(TAa) AR1, AR1-(1–4C)alkyl-, AR2 (carbon linked), AR3;

(TAb) AR1-CH(OH), AR2-CH(OH)—, AR3-CH(OH)—;

(TAc) AR1-CO—, AR2-CO—, AR3-CO—, AR4-CO—;

(TAd) AR1-O—, AR2-O—, AR3-O—;

(TAe) AR1-S(O)$_q$—, AR2-S(O)$_q$—, AR3—S(O)$_q$— (q is 0, 1 or 2);

(TAf) an optionally substituted N-linked (fully unsaturated) 5-membered heteroaryl ring system containing 1, 2 or 3 nitrogen atoms;

(TAg) a carbon linked tropol-3-one or tropol-4-one, optionally substituted in a position not adjacent to the linking position; or (TB) T is selected from the following groups:—

(TBa) halo or (1–4C)alkyl {optionally substituted by one or more groups each independently selected from hydroxy, (1–4C)alkoxy, (1–4C)alkanoyl, cyano, halo, trifluoromethyl, (1–4C)alkoxycarbonyl, —NRvRw, (1–6C)alkanoylamino, (1–4C)alkoxycarbonylamino, N-(1–4C)alkyl-N-(1–6C)alkanoylamino, (1–4C)alkylS(O)$_q$— (q is 0, 1 or 2), CY1, CY2 or AR1};

(TBb) —NRv$^1$Rw$^1$;

(TBc) ethenyl, 2-(1–4C)alkylethenyl, 2-cyanoethenyl, 2-cyano-2-((1–4C)alkyl)ethenyl, 2-nitroethenyl, 2-nitro-2-((1–4C)alkyl)ethenyl, 2-((1–4C)alkylaminocarbonyl)ethenyl, 2-((1–4C)alkoxycarbonyl)ethenyl, 2-(AR1)ethenyl, 2-(AR2)ethenyl;

(TBd) $R^{10}$CO—, $R^{10}$S(O)$_q$— (q is 0, 1 or 2) or $R^{10}$CS— wherein $R^{10}$ is selected from the following groups:—

(TBda) CY1 or CY2;

(TBdb) hydrogen, (1–4C)alkoxycarbonyl, trifluoromethyl, —NRvRw, ethenyl, 2-(1–4C)alkylethenyl, 2-cyanoethenyl, 2-cyano-2-((1–4C)alkyl)ethenyl, 2-nitroethenyl, 2-nitro-2-((1–4C)alkyl)ethenyl, 2-((1–4C)alkylaminocarbonyl)ethenyl, 2-((1–4C)alkoxycarbonyl)ethenyl, 2-(AR1)ethenyl or 2-(AR2)ethenyl; or (TBdc) (1–4C)alkyl {optionally substituted as defined in (TBa) above, or by (1–4C)alkylS(O)$_p$NH— or (1–4C)alkylS(O)$_p$-((1–4C)alkyl)N— (p is 1 or 2)};

wherein Rv is hydrogen or (1–4C)alkyl; Rw is hydrogen or (1–4C)alkyl; Rv$^1$ is hydrogen, (1–4C)alkyl or (3–8C)cycloalkyl; Rw$^1$ is hydrogen, (1–4C)alkyl, (3–8C)cycloalkyl, (1–4C)alkyl-CO— or (1–4C)alkylS(O)$_q$— (q is 1 or 2); or (TC) T is selected from the following groups:—

(TCa) an optionally substituted, fully saturated 4-membered monocyclic ring containing 1 heteroatom selected from O, N and S (optionally oxidised), and linked via a ring nitrogen or sp$^3$ carbon atom;

(TCb) an optionally substituted 5-membered monocyclic ring containing 1 heteroatom selected from O, N and S (optionally oxidised), and linked via a ring nitrogen atom or a ring sp$^3$ or sp$^2$ carbon atom, which monocyclic ring is fully saturated other than (where appropriate) at a linking sp$^2$ carbon atom;

(TCc) an optionally substituted 6- or 7-membered monocyclic ring containing 1 or 2 heteroatoms independently selected from O, N and S (optionally oxidised), and linked via a ring nitrogen atom or a ring sp$^3$ or sp$^2$ carbon atom, which monocyclic ring is fully saturated other than (where appropriate) at a linking sp$^2$ carbon atom; or (TD) T is selected from the following groups:—

(TDa) a bicyclic spiro-ring system containing 0, 1 or 2 ring nitrogen atoms as the only ring heteroatoms, the structure consisting of a 5- or 6-membered ring system (linked via a ring nitrogen atom or a ring sp$^3$ or sp$^2$ carbon atom) substituted (but not adjacent to the linking position) by a 3-, 4- or 5-membered spiro-carbon-linked ring; which bicyclic ring system is (i) fully saturated other than (where appropriate) at a linking sp$^2$ carbon atom;

(ii) contains one —N(Rc)— group in the ring system (at least two carbon atoms away from the linking position when the link is via a nitrogen atom or an sp$^2$ carbon atom) or one —N(Rc)— group in an optional substituent (not adjacent to the linking position) and is (iii) optionally further substituted on an available ring carbon atom; or (TDb) a 7-, 8- or 9-membered bicyclic ring system (linked via a ring nitrogen atom or a ring sp$^3$ or sp$^2$ carbon atom) containing 0, 1 or 2 ring nitrogen atoms (and optionally a further O or S ring heteroatom), the structure containing a bridge of 1, 2 or 3 carbon atoms; which bicyclic ring system is (i) fully saturated other than (where appropriate) at a linking sp$^2$ carbon atom;

(ii) contains one O or S heteroatom, or one —N(Rc)— group in the ring (at least two carbon atoms away from the linking position when the link is via a nitrogen atom or an sp$^2$ carbon atom) or one —N(Rc)— group in an optional substituent (not adjacent to the linking position) and is (iii) optionally further substituted on an available ring carbon atom;

wherein Rc is selected from groups (Rc1) to (Rc5):—

(Rc1) (1–6C)alkyl {optionally substituted by one or more (1–4C)alkanoyl groups (including geminal disubstitution) and/or optionally monosubstituted by cyano, (1–4C)alkoxy, trifluoromethyl, (1–4C)alkoxycarbonyl, phenyl (optionally substituted as for AR defined hereinafter), (1–4C)alkylS(O)$_q$— (q is 0, 1 or 2); or, on any but the first carbon atom of the (1–6C)alkyl chain, optionally substituted by one or more groups (including geminal disubstitution) each independently selected from hydroxy and fluoro, and/or optionally monosubstituted by oxo, —NRvRw [wherein Rv is hydrogen or (1–4C)alkyl; Rw is hydrogen or (1–4C) alkyl], (1–6C)alkanoylamino, (1–4C)alkoxycarbonylamino, N-(1–4C)alkyl-N-(1–6C)alkanoylamino, (1–4C)alkylS(O)$_p$NH— or (1–4C)alkylS(O)$_p$-((1–4C)alkyl)N— (p is 1 or 2)};

(Rc2) R$^{13}$CO—, R$^{13}$SO$_2$— or R$^{13}$CS— wherein R$^{13}$ is selected from (Rc2a) to (Rc2e):—

(Rc2a) AR1, AR2, AR2a, AR2b, AR3, AR3a, AR3b, AR4, AR4a, CY1, CY2;

(Rc2b) hydrogen, (1–4C)alkoxycarbonyl, trifluoromethyl, —NRvRw [wherein Rv is hydrogen or (1–4C)alkyl; Rw is hydrogen or (1–4C)alkyl], ethenyl, 2-(1–4C)alkylethenyl, 2-cyanoethenyl, 2-cyano-2-((1–4C)alkyl)ethenyl, 2-nitroethenyl, 2-nitro-2-((1–4C)alkyl)ethenyl, 2-((1–4C)alkylaminocarbonyl)ethenyl, 2-((1–4C)alkoxycarbonyl)ethenyl, 2-(AR1)ethenyl, 2-(AR2)ethenyl, 2-(AR2a)ethenyl;

(Rc2c) (1–10C)alkyl

{optionally substituted by one or more groups (including geminal disubstitution) each independently selected from hydroxy, (1–10C)alkoxy, (1–4C)alkoxy-(1–4C)alkoxy, (1–4C)alkoxy-(1–4C)alkoxy-(1–4C)alkoxy, (1–4C)alkanoyl, phosphoryl [—O—P(O)(OH)$_2$, and mono- and di-(1–4C)alkoxy derivatives thereof], phosphiryl [—O—P(OH)$_2$ and mono- and di-(1–4C)alkoxy derivatives thereof], and amino; and/or optionally substituted by one group selected from phosphonate [phosphono, —P(O)(OH)$_2$, and mono- and di-(1–4C)alkoxy derivatives thereof], phosphinate [—P(OH)$_2$ and mono- and di-(1–4C)alkoxy derivatives thereof], cyano, halo, trifluoromethyl, (1–4C)alkoxycarbonyl, (1–4C)alkoxy-(1–4C)alkoxycarbonyl, (1–4C)alkoxy-(1–4C)alkoxy-(1–4C)alkoxycarbonyl, (1–4C)alkylamino, di((1–4C)alkyl)amino, (1–6C)alkanoylamino, (1–4C)alkoxycarbonylamino, N-(1–4C)alkyl-N-(1–6C)alkanoylamino, (1–4C)alkylaminocarbonyl, di((1–4C)alkyl)aminocarbonyl, (1–4C)alkylS(O)$_p$NH—, (1–4C)alkylS(O)$_p$-((1–4C)alkyl)N—, fluoro(1–4C)alkylS(O)$_p$NH—, fluoro(1–4C)alkylS(O)$_p$((1–4C)alkyl)N—, (1–4C)alkylS(O)$_q$— [the (1–4C)alkyl group of (1–4C)alkylS(O)$_q$— being optionally substituted by one substituent selected from hydroxy, (1–4C)alkoxy, (1–4C)alkanoyl, phosphoryl [—O—P(O)(OH)$_2$, and mono- and di-(1–4C)alkoxy derivatives thereof], phosphiryl [—O—P(OH)$_2$ and mono- and di-(1–4C)alkoxy derivatives thereof], amino, cyano, halo, trifluoromethyl, (1–4C)alkoxycarbonyl, (1–4C)alkoxy-(1–4C)alkoxycarbonyl, (1–4C)alkoxy-(1–4C)alkoxy-(1–4C)alkoxycarbonyl, carboxy, (1–4C)alkylamino, di((1–4C)alkyl)amino, (1–6C)alkanoylamino, (1–4C)alkoxycarbonylamino, N-(1–4C)alkyl-N-(1–6C)alkanoylamino, (1–4C)alkylaminocarbonyl, di((1–4C)alkyl)aminocarbonyl, (1–4C)alkylS(O)$_p$NH—, (1–4C)alkylS(O)$_p$-((1–4C)alkyl)N—, (1–4C)alkylS(O)$_q$—, AR1-S(O)$_q$—, AR2-S(O)$_q$—, AR3-S(O)$_q$— and also AR2a, AR2b, AR3a and AR3b versions of AR2 and AR3 containing groups], CY1, CY2, AR1, AR2, AR3, AR1-O—, AR2-O—, AR3-O—, AR1-S(O)$_q$—, AR2-S(O)$_q$—, AR3-S(O)$_q$—, AR1-NH—, AR2-NH—, AR3-NH— (p is 1 or 2 and q is 0, 1 or 2), and also AR2a, AR2b, AR3a and AR3b versions of AR2 and AR3 containing groups};

(Rc2d) R$^{14}$C(O)O(1–6C)alkyl wherein R$^{14}$ is AR1, AR2, (1–4C)alkylamino (the (1–4C)alkyl group being optionally substituted by (1–4C)alkoxycarbonyl or by carboxy), benzyloxy-(1–4C)alkyl or (1–10C)alkyl {optionally substituted as defined for (Rc2c)};

(Rc2e) R$^{15}$O— wherein R$^{15}$ is benzyl, (1–6C)alkyl {optionally substituted as defined for (Rc2c)}, CY1, CY2 or AR2b;

(Rc3) hydrogen, cyano, 2-cyanoethenyl, 2-cyano-2-((1–4C)alkyl)ethenyl, 2-((1–4C)alkylaminocarbonyl)ethenyl, 2-((1–4C)alkoxycarbonyl)ethenyl, 2-nitroethenyl, 2-nitro-2-((1–4C)alkyl)ethenyl, 2-(AR1)ethenyl, 2-(AR2)ethenyl, or of the formula (Rc3a)

(Rc3a)

wherein X$^{00}$ is —OR$^{17}$, —SR$^{17}$, —NHR$^{17}$ and —N(R$^{17}$)$_2$;

wherein R$^{17}$ is hydrogen (when X$^{00}$ is —NHR$^{17}$ and —N(R$^{17}$)$_2$), and R$^{17}$ is (1–4C)alkyl, phenyl or AR2 (when X$^{00}$ is —OR$^{17}$, —SR$^{17}$ and —NHR$^{17}$); and R$^{16}$ is cyano, nitro, (1–4C)alkylsulfonyl, (4–7C)cycloalkylsulfonyl, phenylsulfonyl, (1–4C)alkanoyl and (1–4C)alkoxycarbonyl;

(Rc4) trityl, AR1, AR2, AR2a, AR2b, AR3, AR3a, AR3b;

(Rc5) RdOC(Re)=CH(C=O)—, RfC(=O)C(=O)—, RgN=C(Rh)C(=O) or

RiNHC(Rj)=CHC(=O)— wherein Rd is (1–6C)alkyl; Re is hydrogen or (1–6C)alkyl, or Rd and Re together form a (3–4C)alkylene chain; Rf is hydrogen, (1–6C)alkyl, hydroxy (1–6C)alkyl, (1–6C)alkoxy(1–6C)alkyl, —NRvRw [wherein Rv is hydrogen or (1–4C)alkyl; Rw is hydrogen or (1–4C)alkyl], (1–4C)alkoxy, (1–4C)alkoxy(1–6C)alkoxy, hydroxy(2–6C)alkoxy, (1–4C)alkylamino(2–6C)alkoxy, di-(1–4C)alkylamino(2–6C)alkoxy; Rg is (1–6C)alkyl, hydroxy or (1–6C)alkoxy; Rh is hydrogen or (1–6C)alkyl; Ri is hydrogen, (1–6C)alkyl, AR1, AR2, AR2a, AR2b and Rj is hydrogen or (1–6C)alkyl;

wherein

AR1 is an optionally substituted phenyl or optionally substituted naphthyl;

AR2 is an optionally substituted 5- or 6-membered, fully unsaturated (i.e with the maximum degree of unsaturation) monocyclic heteroaryl ring containing up to four heteroatoms independently selected from O, N and S (but not containing any O—O, O—S or S—S bonds), and linked via a ring carbon atom, or a ring nitrogen atom if the ring is not thereby quaternised;

AR2a is a partially hydrogenated version of AR2 (i.e. AR2 systems retaining some, but not the full, degree of unsaturation), linked via a ring carbon atom or linked via a ring nitrogen atom if the ring is not thereby quaternised;

AR2b is a fully hydrogenated version of AR2 (i.e. AR2 systems having no unsaturation), linked via a ring carbon atom or linked via a ring nitrogen atom;

AR3 is an optionally substituted 8-, 9- or 10-membered, fully unsaturated (i.e with the maximum degree of unsaturation) bicyclic heteroaryl ring containing up to four heteroatoms independently selected from O, N and S (but not containing any O—O, O—S or S—S bonds), and linked via a ring carbon atom in either of the rings comprising the bicyclic system;

AR3a is a partially hydrogenated version of AR3 (i.e. AR3 systems retaining some, but not the full, degree of unsaturation), linked via a ring carbon atom, or linked via a ring nitrogen atom if the ring is not thereby quaternised, in either of the rings comprising the bicyclic system;

AR3b is a fully hydrogenated version of AR3 (i.e. AR3 systems having no unsaturation), linked via a ring carbon atom, or linked via a ring nitrogen atom, in either of the rings comprising the bicyclic system;

AR4 is an optionally substituted 13- or 14-membered, fully unsaturated (i.e with the maximum degree of unsaturation) tricyclic heteroaryl ring containing up to four heteroatoms independently selected from O, N and S (but not containing any O—O, O—S or S—S bonds), and linked via a ring carbon atom in any of the rings comprising the tricyclic system;

AR4a is a partially hydrogenated version of AR4 (i.e. AR4 systems retaining some, but not the full, degree of unsaturation), linked via a ring carbon atom, or linked via a ring nitrogen atom if the ring is not thereby quaternised, in any of the rings comprising the tricyclic system;

CY1 is an optionally substituted cyclobutyl, cyclopentyl or cyclohexyl ring;

CY2 is an optionally substituted cyclopentenyl or cyclohexenyl ring.

In this specification, where it is stated that a ring may be linked via an $sp^2$ carbon atom, which ring is fully saturated other than (where appropriate) at a linking $sp^2$ carbon atom, it is to be understood that the ring is linked via one of the carbon atoms in a C═C double bond.

In another embodiment, (Rc1) is as defined above other than the optional phenyl substituent on (1–6C)alkyl is optionally substituted as for AR1 defined hereinafter, and (Rc2c), is as defined above and further includes carboxy as an optional substituent on $R^{13}$ as (1–10C)alkyl.

(TAf) When T is an optionally substituted N-linked (fully unsaturated) 5-membered heteroaryl ring system containing 1, 2 or 3 nitrogen atoms, it is preferably selected from a group of formula (TAf1) to (TAf6) below (particularly (TAf1), (TAf2), (TAf4) and (TAf5), and especially (TAf1) and/or (TAf2)). The above preferred values of (TAf) are particularly preferred when present in Q1 or Q2, especially Q1.

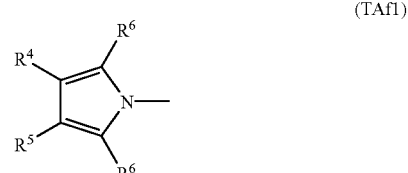

(TAf1)

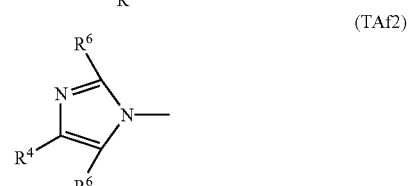

(TAf2)

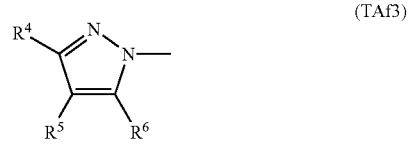

(TAf3)

(TAf4)

(TAf5)

(TAf6)

wherein:

$R^6$ is selected (independently where appropriate) from hydrogen, (1–4C)alkyl, (1–4C)alkoxycarbonyl, (1–4C)alkanoyl, carbamoyl and cyano;

$R^4$ and $R^5$ are independently selected from hydrogen, halo, trifluoromethyl, cyano, nitro, (1–4C)alkoxy, (1–4C)alkylS(O)$_q$— (q is 0, 1 or 2), (1–4C)alkanoyl, (1–4C)alkoxycarbonyl, (2–4C)alkanoyloxy-(1–4C)alkyl, benzoxy-(1–4C)alkyl, (2–4C)alkanoylamino, —CONRvRw, —NRvRw and (1–4C)alkyl {optionally substituted by hydroxy, trifluoromethyl, cyano, nitro, (1–4C)alkoxy, (1–4C)alkylS(O)$_q$— (q is 0, 1 or 2), (1–4C)alkoxycarbonyl, (1–4C)alkanoylamino, —CONRvRw, —NRvRw; wherein RvRw is hydrogen or (1–4C)alkyl; Rw is hydrogen or (1–4C)alkyl};

or $R^4$ is selected from one of the groups in (TAfa) to (TAfc) below, or (where appropriate) one of $R^4$ and $R^5$ is selected from the above list of $R^4$ and $R^5$ values, and the other is selected from one of the groups in (TAfa) to (TAfc) below:—

(TAfa) a group of the formula (TAfa1)

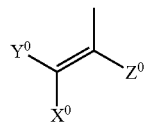

(TAfa1)

wherein $Z^0$ is hydrogen or (1–4C)alkyl;

$X^0$ and $Y^0$ are independently selected from hydrogen, (1–4C)alkyl, (1–4C)alkoxycarbonyl, halo, cyano, nitro, (1–4C)alkylS(O)$_q$— (q is 0, 1 or 2), RvRwNSO$_2$—, trifluoromethyl, pentafluoroethyl, (1–4C)alkanoyl and —CONRvRw [wherein Rv is hydrogen or (1–4C)alkyl; Rw is hydrogen or (1–4C)alkyl]; or one of $X^0$ and $Y^0$ is selected from the above list of $X^0$ and $Y^0$ values, and the other is selected from phenyl, phenylcarbonyl, —S(O)$_q$-phenyl (q is 0, 1 or 2), N-(phenyl)carbamoyl, phenylaminosulfonyl, AR2, (AR2)-CO—, (AR2)-S(O)$_q$— (q is 0, 1 or 2), N-(AR2)carbamoyl and (AR2)aminosulfonyl; wherein any phenyl group in (TAfa) may be optionally substituted by up to three substituents independently selected from (1–4C)alkyl, cyano, trifluoromethyl, nitro, halo and (1–4C)alkylsulfonyl;

(TAjb) an acetylene of the formula —≡—H or -≡-(1–4C)alkyl;

(TAfc) —$X^1$—$Y^1$—AR2, —$X^1$—$Y^1$—AR2a, —$X^1$—$Y^1$—AR2b, —$X^1$—$Y^1$—AR3, —$X^1$—$Y^1$—AR3a or —$X^1$—$Y^1$—AR3b;

wherein $X^1$ is a direct bond or —CH(OH)— and $Y^1$ is —(CH$_2$)$_m$—, —(CH$_2$)$_n$—NH—(CH$_2$)$_m$—, —CO—(CH$_2$)$_m$—, —CONH—(CH$_2$)$_m$—, —C(=S)NH—(CH$_2$)$_m$— or —C(=O)O—(CH$_2$)$_m$—;

or wherein $X^1$ is —(CH$_2$)$_n$— or —CH(Me)—(CH$_2$)$_m$— and $Y^1$ is —(CH$_2$)$_m$—NH—(CH$_2$)$_m$—, —CO—(CH$_2$)$_m$—, —CONH—(CH$_2$)$_m$—, —C(=S)NH—(CH)$_m$—, —C(=O)O—(CH$_2$)$_m$— or —S(O)$_q$—(CH$_2$)$_m$—;

or wherein $X^1$ is —CH$_2$O—, —CH$_2$NH— or —CH$_2$N((1–4C)alkyl)- and $Y^1$ is —CO—(CH$_2$)$_m$—, —CONH—(CH$_2$)$_m$— or —C(=S)NH—(CH$_2$)$_m$—; and additionally $Y^1$ is —SO$_2$— when $X^1$ is —CH$_2$NH— or —CH$_2$N((1–4C)alkyl)-, and $Y^1$ is —(CH$_2$)$_m$ when $X^1$ is —CH$_2$O— or —CH$_2$N((1–4C)alkyl)-; wherein n is 1, 2 or 3; m is 0, 1, 2 or 3 and q is 0, 1 or 2; and when $Y^1$ is —(CH$_2$)$_m$—NH—(CH$_2$)$_m$— each m is independently selected from 0, 1, 2 or 3.

It is to be understood that when a value for —$X^1$— is a two-atom link and is written, for example, as —CH$_2$NH— it is the left hand part (—CH$_2$— here) which is bonded to the group of formula (TAf1) to (TAf6) and the right hand part (—NH— here) which is bonded to —$Y^1$— in the definition in (TAfc). Similarly, when —$Y^1$— is a two-atom link and is written, for example, as —CONH— it is the left hand part of —$Y^1$— (—CO— here) which is bonded to the right hand part of —$X^1$—, and the right hand part of —$Y^1$— (—NH— here) which is bonded to the AR2, AR2a, AR2b, AR3, AR3a or AR3b moiety in the definition in (TAfc).

Preferably $R^6$ is hydrogen or (1–4C)alkyl, and $R^4$ and $R^5$ are independently selected from hydrogen, (1–4C)alkyl or one of $R^4$ and $R^5$ is selected from group (TAfa). Other preferable substituents on the (TAf1) to (TAf6) are illustrated in the accompanying Examples. Most preferable is (TAf2) with such preferable substituents.

(TAg) When T is a carbon linked tropol-3-one or tropol-4-one, optionally substituted in a position not adjacent to the linking position (TAg), it is preferably selected from a group of formula (TAg1), (TAg2) or (TAg3). The above preferred values of (TAg) are particularly preferred when present in Q1 or Q2, especially Q1.

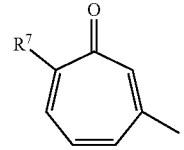

(TAg1)

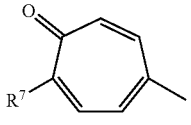

(TAg2)

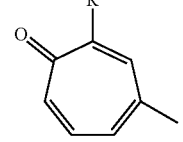

(TAg3)

wherein $R^7$ is selected from (TAga) hydrogen, (1–4C)alkyl {optionally substituted by one or two substituents (excluding geminal disubstitution) independently selected from fluoro, hydroxy, (1–4C)alkoxy and —NRvRw]}; or (TAgb) $R^8$—O—, $R^8$—S—, $R^8$—NH— or $R^8R^8$—N—;

wherein $R^8$ is selected (independently where appropriate) from hydrogen, (1–4C)alkyl or (3–8C)cycloalkyl {both optionally substituted by one or two substituents (excluding geminal disubstitution) independently selected from hydroxy, (1–4C)alkoxy, (1–4C)alkoxycarbonyl and —NRvRw}, (2–4C)alkenyl {optionally substituted by one or two —NRvRw substituents}, (1–4C)alkanoyl {optionally substituted by one or two substituents independently selected from —NRvRw and hydroxy}, phenyl-(1–4C)alkyl or pyridyl-(1–4C)alkyl {the phenyl and pyridyl (preferably pyridin-4-yl) rings being optionally substituted by one or two —NRvRw substituents}; or (TAgc) morpholino, thiomorpholino, pyrrolidino {optionally independently substituted in the 3- and/or 4-positions by (1–4C)alkyl}, piperidino substituted in the 4-position by $R^9$—, $R^9$—O—, $R^9$—S—, $R^9$—NH— or $R^9R^9$—N—; wherein $R^9$ is selected (independently where appropriate) from hydrogen, (1–4C)alkyl {optionally substituted by one or two (excluding geminal disubstitution) hydroxy, (1–4C)alkoxy, (1–4C)alkoxycarbonyl or —NRvRw} and piperazino {optionally substituted in the 4-position by (1–4C)

alkyl, (3–8C)cycloalkyl, (1–4C)alkanoyl, (1–4C) alkoxycarbonyl or (1–4C)alkylsulfonyl, and optionally independently substituted in the 3- and/or 5-positions by (1–4C)alkyl}; wherein Rv is hydrogen or (1–4C)alkyl; Rw is hydrogen or (1–4C)alkyl.

(TC) Preferred values for the optional substituents and groups defined in (TCa) to (TCc) are defined by formulae (TC1) to (TC4):—

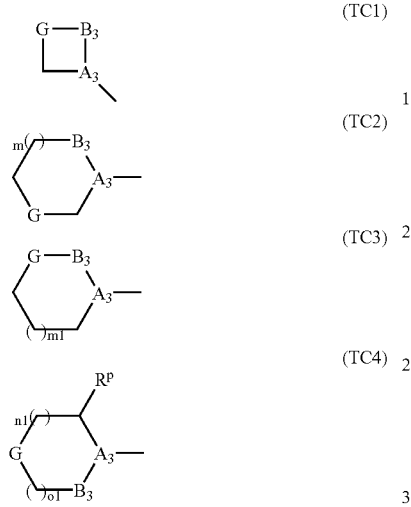

wherein in (TC1): >$A_3$—$B_3$— is >C(Rq)—CH(Rr)— and G is —O—, —S—, —SO—, —SO$_2$— or >N(Rc);

wherein in (TC2): m1 is 0, 1 or 2; >$A_3$—$B_3$— is >C=C(Rr)— or >C(Rq)—CH(Rr)— and G is —O—, —S—, —SO—, —SO$_2$— or >N(Rc);

wherein in (TC3): m1 is 0, 1 or 2; >$A_3$—$B_3$— is >C(Rq)—CH(Rr)— (other than when Rq and Rr are both together hydrogen) and G is —O—, —S—, —SO—, —SO$_2$— or >N(Rc);

wherein in (TC4): n1 is 1 or 2; o1 is 1 or 2 and n1+o1=2 or 3; >$A_3$—$B_3$— is >C=C(Rr)— or >C(Rq)—CH(Rr)— or >N—CH$_2$— and G is —O—, —S—, —SO—, —SO$_2$— or >N(Rc); Rp is hydrogen, (1–4C)alkyl (other than when such substitution is defined by >$A_3$—$B_3$—), hydroxy, (1–4C)alkoxy or (1–4C)alkanoyloxy;

wherein in (TC1), (TC2) and (TC4); m1, n1 and o1 are as defined hereinbefore:

>$A_3$—$B_3$— is >N—CH$_2$— and G is >C($R^{11}$)($R^{12}$), >C=O, >C—OH, >C-(1–4C)alkoxy, >C=N—OH, >C=N-(1–4C)alkoxy, >C=N—NH-(1–4C)alkyl, >C=N—N((1–4C)alkyl)$_2$ (the last two (1–4C)alkyl groups above in G being optionally substituted by hydroxy) or >C=N—N—CO-(1–4C)alkoxy; wherein > represents two single bonds;

Rq is hydrogen, hydroxy, halo, (1–4C)alkyl or (1–4C)alkanoyloxy;

Rr is (independently where appropriate) hydrogen or (1–4C)alkyl;

$R^{11}$ is hydrogen, (1–4C)alkyl, fluoro(1–4C)alkyl, (1–4C)alkyl-thio-(1–4C)alkyl or hydroxy-(1–4C)alkyl and $R^{12}$ is —[C(Rr)(Rr)]$_{m2}$—N(Rr)(Rc) wherein m2 is 0, 1 or 2;

and, other than the ring substitution defined by G, >$A_3$—$B_3$— and Rp, each ring system may be optionally further substituted on a carbon atom not adjacent to the link at >$A_3$— by up to two substituents independently selected from (1–4C)alkyl, fluoro(1–4C)alkyl (including trifluoromethyl), (1–4C)alkyl-thio-(1–4C)alkyl, hydroxy-(1–4C)alkyl, amino, amino-(1–4C)alkyl, (1–4C)alkanoylamino, (1–4C)alkanoylamino-(1–4C)alkyl, carboxy, (1–4C)alkoxycarbonyl, AR-oxymethyl, AR-thiomethyl, oxo (=O) (other than when G is >N—Rc and Rc is group (Rc2) defined hereinbefore) or independently selected from Rc; and also hydroxy or halo (the last two optional substituents only when G is —O— or —S—); wherein AR (or ARp) is as defined for formula (IP) hereinafter; Rc is selected from groups (Rc1) to (Rc5) defined hereinbefore.

For the avoidance of doubt, ( )$_{m1}$, ( )$_{n1}$ and ( )$_{o1}$ indicate (—CH$_2$—)$_{m1}$, (—CH$_2$—)$_{n1}$, and (—CH$_2$—)$_{o1}$, respectively (optionally substituted as described above).

In the above definition of (TC1) to (TC4) and of the further optional substituents, AR is preferably AR2, and the further optional substituents are preferably not selected from the values listed for Rc. A preferred value for G is >N(Rc) or >C($R^{11}$)($R^{12}$).

Particularly preferred values for the optional substituents and groups defined in (TCa) to (TCc), and (TC1) to (TC4) are contained in the following definitions (TC5) to (TC11):—

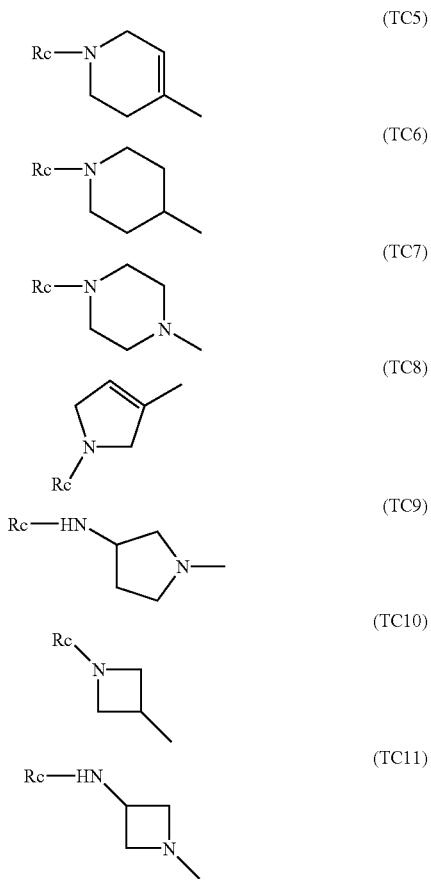

wherein Rc has any of the values listed hereinbefore or hereinafter.

Especially preferred are (TC5), (TC6), (TC7) and (TC9), most especially (TC5) in which Rc has any of the values listed hereinbefore or hereinafter (especially $R^{13}CO$— with the preferable $R^{13}$ values given hereinafter). In (TC5) Rc is preferably selected from the group (Rc2), especially $R^{13}CO$— with the preferable $R^{13}$ values given hereinafter. In (TC7) Rc is preferably selected from group (Rc3) or (Rc4).

The above preferred values of (TCa) to (TCc) are particularly preferred when present in Q1 or Q2, especially Q1 (especially when HET is isoxazole).

(TDa) When T is a bicyclic spiro-ring system as defined in (TDa), it is preferably selected from a group of formula (TDa1) to (TDa9). The above preferred values of (TDa) are particularly preferred when present in Q1 or Q2, especially Q1.

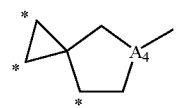
(TDa1)

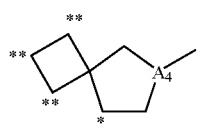
(TDa2)

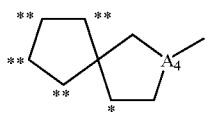
(TDa3)

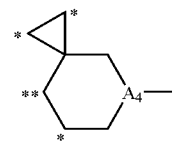
(TDa4)

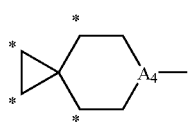
(TDa5)

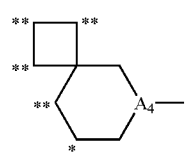
(TDa6)

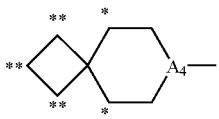
(TDa7)

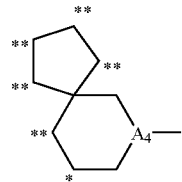
(TDa8)

(TDa9)

wherein;

(i) the $A_4$ linking group is a nitrogen atom or an $sp^3$ or $sp^2$ carbon atom (with the double bond, where appropriate, orientated in either direction); and (ii) one of the ring carbon atoms at positions marked * and ** is replaced by one of the following groups —NRc—, >CH—NHRc, >CH—NRc-(1–4C)alkyl, >CH—CH$_2$—NHRc, >CH—CH$_2$—NRc-(1–4C)alkyl [wherein a central —CH$_2$— chain link is optionally mono- or di-substituted by (1–4C)alkyl]; with the provisos that positions marked * are not replaced by —NH— in the ring containing the $A_4$ link when $A_4$ is a nitrogen atom or an $sp^2$ carbon atom, and that positions marked * are not replaced by —NH— in the three membered ring in (TDa1), (TDa4) and (TDa5); and (iii) the ring system is optionally (further) substituted on an available ring carbon atom by up to two substituents independently selected from (1–4C)alkyl, fluoro(1–4C)alkyl (including trifluoromethyl), (1–4C)alkyl-thio-(1–4C)alkyl, hydroxy-(1–4C)alkyl, amino, amino-(1–4C)alkyl, (1–4C)alkanoylamino, (1–4C)alkanoylamino-(1–4C)alkyl, carboxy, (1–4C)alkoxycarbonyl, AR2-oxymethyl, AR2-thiomethyl, oxo (═O) (other than when the ring contains an >N—Rc and Rc is group (Rc2)) and also hydroxy or halo; wherein Rc has any of the values listed hereinbefore or hereinafter.

(TDb) When T is a 7-, 8- or 9-membered bicyclic ring system containing a bridge of 1, 2 or 3 carbon atoms as defined in (TDb), it is preferably selected from a group defined by the ring skeletons shown in formulae (TDb1) to (TDb14):—

7-membered ring skeletons

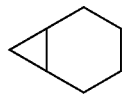
[4,1,0]
(TDb1)

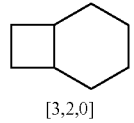
[3,2,0]
(TDb2)

-continued

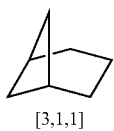
[3,1,1]

[2,2,1]

8-membered ring skeletons

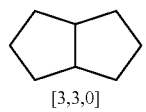
[3,3,0]

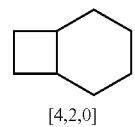
[4,2,0]

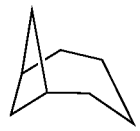
[4,1,1]

[3,2,1]

[2,2,2]

9-membered ring skeletons

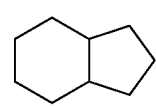
[4,3,0]

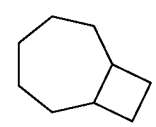
[5,2,0]

-continued (TDb3)

(TDb4)

(TDb5)

(TDb6)

(TDb7)

(TDb8)

(TDb9)

(TDb10)

(TDb11)

[4,2,1]
(TDb12)

[3,3,1]
(TDb13)

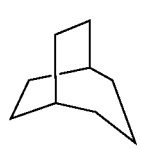
[3,2,2]
(TDb14)

wherein;

(i) the ring system contains 0, 1 or 2 ring nitrogen atoms (and optionally a further O or S ring heteroatom), and when present the ring nitrogen, O or S heteroatom/s are at any position other than as part of the 3-membered ring in (TDb1);

(ii) the ring system is linked via a ring nitrogen atom or a ring sp³ or sp² carbon atom (with the double bond, where appropriate, orientated in either direction) from any position in either ring [other than from a bridgehead position or from an sp² carbon atom in the 4-membered ring in (TDb2), (TDb6) and (TDb11)];

(iii) one of the ring carbon atoms at a position not adjacent to the linking position, is replaced (other than when the ring contains an O or S heteroatom) by one of the following groups —NRc— [not at a bridgehead position], >C(H)—NHRc, >C(H)—NRc-(1–4C)alkyl, >C(H)—CH₂—NHRc, >C(H)—CH₂—NRc-(1–4C)alkyl [wherein the hydrogen atom shown in brackets is not present when the replacement is made at a bridgehead position and wherein a central —CH₂— chain link is optionally mono- or di-substituted by (1–4C)alkyl]; with the proviso that when the ring system is linked via a ring nitrogen atom or an sp² carbon atom any replacement of a ring carbon atom by —NRc—, O or S is at least two carbon atoms away from the linking position; and (iv) the ring system is optionally (further) substituted on an available ring carbon atom as for the bicyclic spiro-ring systems described in (TDa); wherein Rc has any of the values listed hereinbefore or hereinafter.

It will be appreciated that unstable anti-Bredt compounds are not contemplated in this definition (i.e. compounds with stuctures (TDb3), (TDb4), (TDb7), (TDb8), (TDb9), (TDb12), (TDb13) and (TDb14) in which an sp² carbon atom is directed towards a bridgehead position).

Particularly preferred values of (TDb) are the following structures of formula (TDb4), (TDb8) and/or (TDb9); wherein Rc has any of the values listed hereinbefore or hereinafter. The above preferred values of (TDb) are particularly preferred when present in Q1 or Q2, especially Q1.

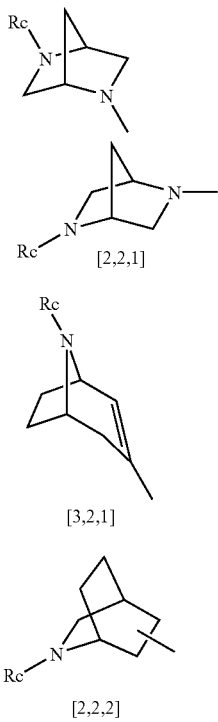

(TDb4a & b)

[2,2,1] (TDb8)

[3,2,1] (TDb9)

[2,2,2]

In another embodiment there is provided a compound of formula (I) as defined by formula (IP) below:

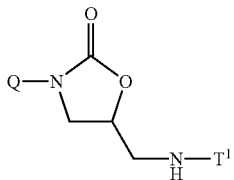

(IP)

wherein $T^1$ is a C-linked isoxazole ring which is optionally substituted on any available C atom by 1 or 2 substituents independently selected from (1–4C)alkyl, amino, (1–4C)alkylamino, (1–4C)alkoxy and halogen;

Q is

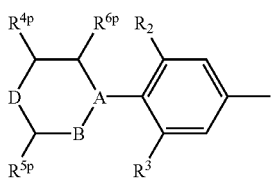

wherein:

$R^2$ and $R^3$ are independently hydrogen or fluoro;

$R^{6p}$ is hydrogen, (1–4C)alkyl, hydroxy, (1–4C)alkoxy or (2–4C)alkanoyloxy; >A—B— is of the formula >C=C($R^a$)—, >CHCHR$^a$—, >C(OH)CHR$^a$— or >N—CH$_2$— (>represents two single bonds) wherein R$^a$ is hydrogen or (1–4C)alkyl;

D is O, S, SO, SO$_2$ or NR$^{7p}$;

$R^{4p}$ and $R^{5p}$ are independently oxo (=O) [but not when $R^{7p}$ is group (PC) below], (1–4C)alkyl, (1–4C)alkanoylamino-(1–4C)alkyl, hydroxy-(1–4C)alkyl, carboxy, (1–4C)alkoxycarbonyl, ARp-oxymethyl, ARp-thiomethyl (wherein ARp is as defined hereinbelow) or independently as defined for $R^{7p}$ hereinbelow with the proviso that $R^{4p}$ and $R^{5p}$ are not phenyl, benzyl, ARp (as defined hereinbelow), a tetrazole ring system, cyclopentyl or cyclohexyl; and when D is O or S, $R^{4p}$ and $R^{5p}$ are additionally independently hydroxy or bromo;

wherein $R^{7p}$ is selected from (PA) to (PE):—

(PA) hydrogen, cyano, 2-((1–4C)alkoxycarbonyl)ethenyl, 2-cyanoethenyl, 2-cyano-2-((1–4C)alkyl)ethenyl, 2-((1–4C)alkylaminocarbonyl)ethenyl;

(PB) phenyl, benzyl, ARp (as defined hereinbelow) or a tetrazole ring system [optionally mono-substituted in the 1- or 2-position of the tetrazole ring by (1–4C)alkyl, (2–4C)alkenyl, (2–4C)alkynyl or (1–4C)alkanoyl] wherein the tetrazole ring system is joined to the nitrogen in NR$^{7p}$ by a ring carbon atom;

(PC)$R^{10p}$CO—, $R^{10p}$SO$_2$— or $R^{10p}$CS— wherein $R^{10p}$ is selected from (PCa) to (PCf):—

(PCa) ARp (as defined hereinbelow);

(PCb) cyclopentyl or cyclohexyl or 1,3-dioxolan-4-yl or 1,4-dioxan-2-yl or 1,3-dioxan-4-yl [optionally mono- or disubstituted by substituents independently selected from (1–4C)alkyl (including geminal disubstitution), hydroxy (but excluding 1,3-dioxolan-4-yl, 1,4-dioxan-2-yl and 1,3-dioxan-4-yl substituted by hydroxy), (1–4C)alkoxy, (1–4C)alkylthio, acetamido, (1–4C)alkanoyl, cyano and trifluoromethyl];

(PCc) hydrogen, (1–4C)alkoxycarbonyl, trifluoromethyl, amino, (1–4C)alkylamino, di((1–4C)alkyl)amino, 2-(5- or 6-membered heteroaryl)ethenyl, 2-(5- or 6-membered (partially) hydrogenated heteroaryl)ethenyl, 2-phenylethenyl [wherein the heteroaryl or phenyl substituent is optionally substituted on an available carbon atom by up to three substituents independently selected from (1–4C)alkoxy, halo, cyano and (for the phenyl substituent only) (1–4C)alkylsulfonyl];

(PCd) (1–10C)alkyl [optionally substituted by one or more groups (including geminal disubstitution) each independently selected from hydroxy and amino, or optionally monosubstituted by cyano, halo, (1–10C)alkoxy, trifluoromethyl, (1–4C)alkoxy-(1–4C)alkoxy, (1–4C)alkoxy-(1–4C)alkoxy-(1–4C)alkoxy, (1–4C)alkanoyl, (1–4C)alkoxycarbonyl, (1–4C)alkylamino, di((1–4C)alkyl)amino, (1–6C)alkanoylamino, (1–4C)alkoxycarbonylamino, N-(1–4C)alkyl-N-(2–6C)alkanoylamino, (1–4C)alkylS(O)$_p$NH—, (1–4C)alkylS(O)$_p$((1–4C)alkyl)N—, fluoro(1–4C)alkylS(O)$_p$NH—, fluoro(1–4C)alkylS(O)$_p$((1–4C)alkyl)N—, phosphono, (1–4C)alkoxy(hydroxy)phosphoryl, di-(1–4C)alkoxyphosphoryl, (1–4C)alkylS(O)$_q$—, phenyl, naphthyl, phenoxy, naphthoxy, phenylamino, naphthylamino, phenylS(O)$_q$—, naphthylS(O)$_q$— [wherein said phenyl and naphthyl groups are optionally substituted by up to three substituents independently selected from (1–4C)

alkoxy, halo and cyano], or CYp (as defined hereinbelow), wherein (where appropriate) p is 1 or 2 and q is 0, 1 or 2];

(PCe) $R^{11p}C(O)O(1-6C)$alkyl wherein $R^{11p}$ is an optionally substituted 5- or 6-membered heteroaryl, optionally substituted phenyl, (1–4C)alkylamino, benzyloxy-(1–4C)alkyl or optionally substituted (1–10C)alkyl;

(PCf) $R^{12p}O$— wherein $R^{12p}$ is benzyl or optionally substituted (1–6C)alkyl;

(PD) $R^dOC(R^e)$=CH(C=O)—, $R^fC$(=O)C(=O)—, $R^gN$=C($R^h$)C(=O)— or $R^iNHC(R^j)$=CHC(=O)— wherein $R^d$ is (1–6C)alkyl, $R^e$ is hydrogen or (1–6C)alkyl, or $R^d$ and $R^e$ together form a (3–4C)alkylene chain, $R^f$ is hydrogen, (1–6C)alkyl, hydroxy(1–6C)alkyl, (1–6C)alkoxy (1–6C)alkyl, amino, (1–4C)alkylamino, di-(1–4C)alkylamino, (1–6C)alkoxy, (1–6C)alkoxy(1–6C)alkoxy, hydroxy (2–6C)alkoxy, (1–4C)alkylamino(2–6C)alkoxy, di-(1–4C)alkylamino(2–6C)alkoxy, $R^g$ is (1–6C)alkyl, hydroxy or (1–6C)alkoxy, $R^h$ is hydrogen or (1–6C)alkyl, $R^i$ is hydrogen, (1–6C)alkyl, optionally substituted phenyl or an optionally substituted 5- or 6-membered heteroaryl [and (partially) hydrogenated versions thereof] and $R^j$ is hydrogen or (1–6C)alkyl;

(PE) $R^{14p}CH(R^{13p})(CH_2)_m$— wherein m is 0 or 1, $R^{13p}$ is fluoro, cyano, (1–4C)alkoxy, (1–4C)alkylsulfonyl, (1–4C)alkoxycarbonyl or hydroxy, (provided that when m is 0, $R^{13p}$ is not fluoro or hydroxy) and $R^{14p}$ is hydrogen or (1–4C)alkyl;

wherein ARp is optionally substituted phenyl, optionally substituted phenyl(1–4C)alkyl, optionally substituted naphthyl, optionally substituted 5- or 6-membered heteroaryl;

wherein ARp is also an optionally substituted 5/6 or 6/6 bicyclic heteroaryl ring system, in which the bicyclic heteroaryl ring systems may be linked via an atom in either of the rings comprising the bicyclic system, and wherein both the mono- and bicyclic heteroaryl ring systems are linked via a ring carbon atom and may be (partially) hydrogenated;

wherein CYp is selected from:—

(i) 4-, 5- or 6-membered cycloalkyl ring;

(ii) 5- or 6-membered cycloalkenyl ring;

(iii) 5- or 6-membered heteroaryl, 5- or 6-membered heteroaryloxy, 5- or 6-membered heteroaryl-S(O)$_q$—, 5- or 6-membered heteroarylamino [and (partially) hydrogenated versions thereof] and (iv) 5/6 or 6/6 bicyclic heteroaryl, 5/6 or 6/6 bicyclic heteroaryloxy, 5/6 or 6/6 bicyclic heteroaryl-S(O)$_q$—, 5/6 or 6/6 bicyclic heteroarylamino [and (partially) hydrogenated versions thereof];

wherein q is 0, 1 or 2 and any of the aforementioned ring systems in CYp may be optionally substituted by up to three substituents independently selected from halo, (1–4C)alkyl [including geminal disubstitution when CYp is a cycloalkyl or cycloalkenyl ring], acyl, oxo and nitro-(1–4C)alkyl; and pharmaceutically-acceptable salts thereof.

In this embodiment (IP) of the specification the term 'alkyl' includes straight chained and branched structures. For example, (1–6C)alkyl includes propyl, isopropyl and tert-butyl. However, references to individual alkyl groups such as "propyl" are specific for the straight chained version only, and references to individual branched chain alkyl groups such as "isopropyl" are specific for the branched chain version only. A similar convention applies to other radicals, for example halo(1–4C)alkyl includes 1-bromoethyl and 2-bromoethyl.

In this embodiment (IP) of the specification a '5- or 6-membered heteroaryl' and 'heteroaryl (monocyclic) ring' means a 5- or 6-membered aryl ring wherein (unless stated otherwise) 1, 2 or 3 of the ring atoms are selected from nitrogen, oxygen and sulfur. Unless stated otherwise, such rings are fully aromatic. Particular examples of 5- or 6-membered heteroaryl ring systems are furan, pyrrole, pyrazole, imidazole, triazole, pyrimidine, pyridazine, pyridine, isoxazole, oxazole, isothiazole, thiazole and thiophene.

In this embodiment (IP) of the specification a '5/6 or 6/6 bicyclic heteroaryl ring system' and 'heteroaryl (bicyclic) ring' means an aromatic bicyclic ring system comprising a 6-membered ring fused to either a 5 membered ring or another 6 membered ring, the bicyclic ring system containing 1 to 4 heteroatoms selected from nitrogen, oxygen and sulfur. Unless stated otherwise, such rings are fully aromatic. Particular examples of 5/6 and 6/6 bicyclic ring systems are indole, benzofuran, benzoimidazole, benzothiophene, benzisothiazole, benzoxazole, benzisoxazole, pyridoimidazole, pyrimidoimidazole, quinoline, quinoxaline, quinazoline, phthalazine, cinnoline and naphthyridine.

In this embodiment (IP) of the specification a '4-, 5- or 6-membered cycloalkyl ring' means a cyclobutyl, cyclopentyl or cyclohexyl ring; and a '5- or 6-membered cycloalkenyl ring' a means cyclopentenyl or cyclohexenyl ring.

Particular optional substituents for alkyl, phenyl (and phenyl containing moieties) and naphthyl groups and ring carbon atoms in heteroaryl (mono or bicyclic) rings in $R^{11p}$, $R^{12p}$, $R^i$ and ARp include halo, (1–4C)alkyl, hydroxy, nitro, carbamoyl, (1–4C)alkylcarbamoyl, di-((1–4C)alkyl)carbamoyl, cyano, trifluoromethyl, trifluoromethoxy, amino, (1–4C)alkylamino, di((1–4C)alkyl)amino, ($^{14}$C)alkylS(O)$_q$—, (wherein q is 0, 1 or 2), carboxy, (1–4C)alkoxycarbonyl, (24C)alkenyl, (2–4C)alkynyl, (1–4C)alkanoyl, (1–4C)alkoxy, (1–4C)alkylS(O)$_2$amino, (1–4C)alkanoylamino, benzoylamino, benzoyl, phenyl (optionally substituted by up to three substituents selected from halo, (1–4C)alkoxy or cyano), furan, pyrrole, pyrazole, imidazole, triazole, pyrimidine, pyridazine, pyridine, isoxazole, oxazole, isothiazole, thiazole, thiophene, hydroxyimino (1–4C)alkyl, (1–4C)alkoxyimino(1–4C)alkyl, hydroxy-(1–4C)alkyl, halo-(1–4C)alkyl, nitro(1–4C)alkyl, amino (1–4C)alkyl, cyano(1–4C)alkyl, (1–4C)alkanesulfonamido, aminosulfonyl, (1–4C)alkylaminosulfonyl and di-((1–4C)alkyl)aminosulfonyl. The phenyl and naphthyl groups and heteroaryl (mono- or bicyclic) rings in $R^{11p}$, $R^i$ and ARp may be mono- or disubstituted on ring carbon atoms with substituents independently selected from the above list of particular optional substituents.

For the avoidance of doubt, phosphono is —P(O)(OH)$_2$; (1–4C)alkoxy(hydroxy)-phosphoryl is a mono-(1–4C)alkoxy derivative of —O—P(O)(OH)$_2$; and di-(1–4C)alkoxyphosphoryl is a di-(1–4C)alkoxy derivative of —O—P(O)(OH)$_2$.

In this embodiment of formula (IP) a '5- or 6-membered heteroaryl' and 'heteroaryl (monocyclic) ring' means a 5- or 6-membered aryl ring wherein (unless stated otherwise) 1, 2 or 3 of the ring atoms are selected from nitrogen, oxygen and sulfur. Unless stated otherwise, such rings are fully aromatic. Particular examples of 5- or 6-membered heteroaryl ring systems are furan, pyrrole, pyrazole, imidazole, triazole, pyrimidine, pyridazine, pyridine, isoxazole, oxazole, isothiazole, thiazole and thiophene.

Particular examples of 5-membered heteroaryl rings containing 2 or 3 heteroatoms independently selected from N, O and S (with the proviso that there are no O—O, O—S or S—S bonds; and in an alternative embodiment, also no N—S bonds) are pyrazole, imidazole, 1,2,3-triazole, 1,2,4-triazole, oxazole, isoxazole, thiazole, 1,2,3-oxadiazole, 1,2,4-oxadiazole, 1,2,5-oxadiazole, 1,3,4-oxadiazole; and also in an alternative embodiment, isothiazole, 1,2,5-thiadiazole, 1,2,4-thiadiazole or 1,2,3-thiadiazole.

In this embodiment of formula (IP) a '5/6 or 6/6 bicyclic heteroaryl ring system' and 'heteroaryl (bicyclic) ring' means an aromatic bicyclic ring system comprising a 6-membered ring fused to either a 5 membered ring or another 6 membered ring, the bicyclic ring system containing 1 to 4 heteroatoms selected from nitrogen, oxygen and sulfur. Unless stated otherwise, such rings are fully aromatic. Particular examples of 5/6 and 6/6 bicyclic ring systems are indole, benzofuran, benzimidazole, benzothiophene, benzisothiazole, benzoxazole, benzisoxazole, pyridoimidazole, pyrimidoimidazole, quinoline, quinoxaline, quinazoline, phthalazine, cinnoline and naphthyridine.

Particular optional substituents for alkyl, phenyl (and phenyl containing moieties) and naphthyl groups and ring carbon atoms in heteroaryl (mono or bicyclic) rings in $R^{14p}$, $R^{15p}$, $R^i$ and ARp include halo, (1–4C)alkyl, hydroxy, nitro, carbamoyl, (1–4C)alkylcarbamoyl, di-((1–4C)alkyl)carbamoyl, cyano, trifluoromethyl, trifluoromethoxy, amino, (1–4C)alkylamino, di((1–4C)alkyl)amino, (1–4C)alkyl S(O)— (q is 0, 1 or 2), carboxy, (1–4C)alkoxycarbonyl, (2–4C)alkenyl, (2–4C)alkynyl, (1–4C)alkanoyl, (1–4C) alkoxy, (1–4C)alkylS(O)$_2$amino, (1–4C)alkanoylamino, benzoylamino, benzoyl, phenyl (optionally substituted by up to three substituents selected from halo, (1–4C)alkoxy or cyano), furan, pyrrole, pyrazole, imidazole, triazole, pyrimidine, pyridazine, pyridine, isoxazole, oxazole, isothiazole, thiazole, thiophene, hydroxyimino(1–4C)alkyl, (1–4C) alkoxyimino(1–4C)alkyl, hydroxy-(1–4C)alkyl, halo-(1–4C)alkyl, nitro(1–4C)alkyl, amino(1–4C)alkyl, cyano (1–4C)alkyl, (1–4C)alkanesulfonamido, aminosulfonyl, (1–4C)alkylaminosulfonyl and di-((1–4C)alkyl)aminosulfonyl. The phenyl and naphthyl groups and heteroaryl (mono- or bicyclic) rings in $R^{14p}$, $R^i$ and ARp may be mono- or di-substituted on ring carbon atoms with substituents independently selected from the above list of particular optional substituents.

In this specification the term 'alkyl' includes straight chained and branched structures. For example, (1–6C)alkyl includes propyl, isopropyl and tert-butyl. However, references to individual alkyl groups such as "propyl" are specific for the straight chained version only, and references to individual branched chain alkyl groups such as "isopropyl" are specific for the branched chain version only. A similar convention applies to other radicals, for example halo(1–4C) alkyl includes 1-bromoethyl and 2-bromoethyl.

There follow particular and suitable values for certain substituents and groups referred to in this specification. These values may be used where appropriate with any of the definitions and embodiments disclosed hereinbefore, or hereinafter.

Examples of (1–4C)alkyl and (1–5C)alkyl include methyl, ethyl, propyl, isopropyl and t-butyl; examples of (1–6C)alkyl include methyl, ethyl, propyl, isopropyl, t-butyl, pentyl and hexyl; examples of (1–10C)alkyl include methyl, ethyl, propyl, isopropyl, pentyl, hexyl, heptyl, octyl and nonyl; examples of (1–4C)alkanoylamino-(1–4C)alkyl include formamidomethyl, acetamidomethyl and acetamidoethyl; examples of hydroxy(1–4C)alkyl and hydroxy (1–6C)alkyl include hydroxymethyl, 1-hydroxyethyl, 2-hydroxyethyl and 3-hydroxypropyl; examples of (1–4C) alkoxycarbonyl include methoxycarbonyl, ethoxycarbonyl and propoxycarbonyl; examples of 2-((1–4C)alkoxycarbonyl)ethenyl include 2-(methoxycarbonyl)ethenyl and 2-(ethoxycarbonyl)ethenyl; examples of 2-cyano-2-((1–4C) alkyl)ethenyl include 2-cyano-2-methylethenyl and 2-cyano-2-ethylethenyl; examples of 2-nitro-2-((1–4C)alkyl) ethenyl include 2-nitro-2-methylethenyl and 2-nitro-2-ethylethenyl; examples of 2-((1–4C)alkylaminocarbonyl) ethenyl include 2-(methylaminocarbonyl)ethenyl and 2-(ethylaminocarbonyl)ethenyl; examples of (2–4C)alkenyl include allyl and vinyl; examples of (24C)alkynyl include ethynyl and 2-propynyl; examples of (1–4C)alkanoyl include formyl, acetyl and propionyl; examples of (1–4C) alkoxy include methoxy, ethoxy and propoxy; examples of (1–6C)alkoxy and (1–10C)alkoxy include methoxy, ethoxy, propoxy and pentoxy; examples of (1–4C)alkylthio include methylthio and ethylthio; examples of (1–4C)alkylamino include methylamino, ethylamino and propylamino; examples of di-((1–4C)alkyl)amino include dimethylamino, N-ethyl-N-methylamino, diethylamino, N-methyl-N-propylamino and dipropylamino; examples of halo groups include fluoro, chloro and bromo; examples of (1–4C)alkylsulfonyl include methylsulfonyl and ethylsulfonyl; examples of (1–4C)alkoxy-(1–4C)alkoxy and (1–6C)alkoxy-(1–6C) alkoxy include methoxymethoxy, 2-methoxyethoxy, 2-ethoxyethoxy and 3-methoxypropoxy; examples of (1–4C)alkoxy-(1–4C)alkoxy-(1–4C)alkoxy include 2-(methoxymethoxy)ethoxy, 2-(2-methoxyethoxy)ethoxy; 3-(2-methoxyethoxy)propoxy and 2-(2-ethoxyethoxy) ethoxy; examples of (1–4C)alkylS(O)$_2$amino include methylsulfonylamino and ethylsulfonylamino; examples of (1–4C)alkanoylamino and (1–6C)alkanoylamino include formamido, acetamido and propionylamino; examples of (1–4C)alkoxycarbonylamino include methoxycarbonylamino and ethoxycarbonylamino; examples of N-(1–4C) alkyl-N-(1–6C)alkanoylamino include N-methylacetamido, N-ethylacetamido and N-methylpropionamido; examples of (1–4C)alkylS(O)$_p$NH— wherein p is 1 or 2 include methylsulfinylamino, methylsulfonylamino, ethylsulfinylamino and ethylsulfonylamino; examples of (1–4C)alkylS(O)$_p$ ((1–4C)alkyl)N— wherein p is 1 or 2 include methylsulfinylmethylamino, methylsulfonylmethylamino, 2-(ethylsulfinyl)ethylamino and 2-(ethylsulfonyl)ethylamino; examples of fluoro(1–4C)alkylS(O)$_p$NH— wherein p is 1 or 2 include trifluoromethylsulfinylamino and trifluoromethylsulfonylamino; examples of fluoro(1–4C)alkylS(O)$_p$ ((1–4C)alkyl)NH— wherein p is 1 or 2 include trifluoromethylsulfinylmethylamino and trifluoromethylsulfonylmethylamino examples of (1–4C) alkoxy(hydroxy)phosphoryl include methoxy(hydroxy) phosphoryl and ethoxy(hydroxy)phosphoryl; examples of di-(1–4C)alkoxyphosphoryl include di-methoxyphosphoryl, di-ethoxyphosphoryl and ethoxy(methoxy)phosphoryl; examples of (1–4C)alkylS(O)$_q$— wherein q is 0, 1 or 2 include methylthio, ethylthio, methylsulfinyl, ethylsulfinyl, methylsulfonyl and ethylsulfonyl; examples of phenylS(O)$_q$ and naphthylS(O)$_q$— wherein q is 0, 1 or 2 are phenylthio, phenylsulfinyl, phenylsulfonyl and naphthylthio, naphthylsulfinyl and naphthylsulfonyl respectively; examples of benzyloxy-(1–4C)alkyl include benzyloxymethyl and benzyloxyethyl; examples of a (3–4C)alkylene chain are trimethylene or tetramethylene; examples of (1–6C)alkoxy-(1–6C)alkyl include methoxymethyl, ethoxymethyl and 2-methoxyethyl; examples of hydroxy-(2–6C)alkoxy include 2-hydroxyethoxy and 3-hydroxypropoxy; examples of (1–4C)alkylamino-(2–6C)alkoxy include 2-methylaminoethoxy and 2-ethylaminoethoxy; examples of di-(1–4C)alkylamino-(2–6C)alkoxy include 2-dimethylaminoethoxy and 2-diethylaminoethoxy; examples of phenyl(1–4C)alkyl include benzyl and phenethyl; examples of (1–4C)alkylcarbamoyl include methylcarbamoyl and ethylcarbamoyl; examples of di((1–4C)alkyl)carbamoyl include di(methyl)carbamoyl and di(ethyl)carbamoyl; examples of hydroxyimino(1–4C)alkyl include hydroxyiminomethyl, 2-(hydroxyimino)ethyl and I-(hydroxyimino)ethyl; examples of (1–4C)alkoxyimino-(1–4C)alkyl include methoxyiminomethyl, ethoxyiminomethyl, 1-(methoxyimino)ethyl and 2-(methoxyimino)ethyl; examples of halo(1–4C)alkyl include, halomethyl, 1-haloethyl, 2-haloethyl, and 3-halopropyl; examples of nitro(1–4C)alkyl include nitromethyl, 1-nitroethyl, 2-nitroethyl and 3-nitropropyl; examples of amino(1–4C)alkyl include aminomethyl, 1-aminoethyl, 2-aminoethyl and 3-aminopropyl; examples of cyano(1–4C)alkyl include cyanomethyl, 1-cyanoethyl, 2-cyanoethyl and 3-cyanopropyl; examples of (1–4C)alkanesulfonamido include methanesulfonamido and ethanesulfonamido; examples of (1–4C)alkylaminosulfonyl include methylaminosulfonyl and ethylaminosulfonyl; and examples of di-(1–4C)alkylaminosulfonyl include dimethylaminosulfonyl, diethylaminosulfonyl and N-methyl-N-ethylaminosulfonyl; examples of (1–4C)alkanesulfonyloxy include methylsulfonyloxy, ethylsulfonyloxy and propylsulfonyloxy; examples of (1–4C)alkanoyloxy include acetoxy; examples of (1–4C)alkylaminocarbonyl include methylaminocarbonyl and ethylaminocarbonyl; examples of di((1–4C)alkyl)aminocarbonyl include dimethylaminocarbonyl and diethylaminocarbonyl; examples of (3–8C)cycloalkyl include cyclopropyl, cyclobutyl, cyclopentyl and cyclohexyl; examples of (4–7C)cycloalkyl include cyclobutyl, cyclopentyl and cyclohexyl; examples of di(N-(1–4C)alkyl)aminomethylimino include dimethylaminomethylimino and diethylaminomethylimino.

Particular values for AR2 include, for example, for those AR2 containing one heteroatom, furan, pyrrole, thiophene; for those AR2 containing one to four N atoms, pyrazole, imidazole, pyridine, pyrimidine, pyrazine, pyridazine, 1,2,3- & 1,2,4-triazole and tetrazole; for those AR2 containing one N and one O atom, oxazole, isoxazole and oxazine; for those AR2 containing one N and one S atom, thiazole and isothiazole; for those AR2 containing two N atoms and one S atom, 1,2,4- and 1,3,4-thiadiazole.

Particular examples of AR2a include, for example, dihydropyrrole (especially 2,5-dihydropyrrol-4-yl) and tetrahydropyridine (especially 1,2,5,6-tetrahydropyridfyl).

Particular examples of AR2b include, for example, tetrahydrofuran, pyrrolidine, morpholine (preferably morpholino), thiomorpholine (preferably thiomorpholino), piperazine (preferably piperazino), imidazoline and piperidine, 1,3-dioxolanfyl, 1,3-dioxan-4-yl, 1,3-dioxan-5-yl and 1,4-dioxan-2-yl.

Particular values for AR3 include, for example, bicyclic benzo-fused systems containing a 5- or 6-membered heteroaryl ring containing one nitrogen atom and optionally 1–3 further heteroatoms chosen from oxygen, sulfur and nitrogen. Specific examples of such ring systems include, for example, indole, benzofuran, benzothiophene, benzimidazole, benzothiazole, benzisothiazole, benzoxazole, benzisoxazole, quinoline, quinoxaline, quinazoline, phthalazine and cinnoline.

Other particular examples of AR3 include 5/5-, 5/6 and 6/6 bicyclic ring systems containing heteroatoms in both of the rings. Specific examples of such ring systems include, for example, purine and naphthyridine.

Further particular examples of AR3 include bicyclic heteroaryl ring systems with at least one bridgehead nitrogen and optionally a ffurther 1–3 heteroatoms chosen from oxygen, sulfur and nitrogen. Specific examples of such ring systems include, for example, 3H-pyrrolo[1,2-a]pyrrole, pyrrolo[2,1-b]thiazole, 1H-imidazo[1,2-a]pyrrole, 1H-imidazo[1,2-a]imidazole, 1H,3H-pyrrolo[1,2-c]oxazole, 1H-imidazo[1,5-a]pyrrole, pyrrolo[1,2-b]isoxazole, imidazo[5,1-b]thiazole, imidazo[2,1-b]thiazole, indolizine, imidazo[1,2-a]pyridine, imidazo[1,5-a]pyridine, pyrazolo[1,5-a]pyridine, pyrrolo[1,2-b]pyridazine, pyrrolo[1,2-c]pyrimidine, pyrrolo[1,2-a]pyrazine, pyrrolo[1,2-a]pyrimidine, pyrido[2,1-c]-s-triazole, s-triazole[1,5-a]pyridine, imidazo[1,2-c]pyrimidine, imidazo[1,2-a]pyrazine, imidazo[1,2-a]pyrimidine, imidazo[1,5-a]pyrazine, imidazo[1,5-a]pyrimidine, imidazo[1,2-b]-pyridazine, s-triazolo[4,3-a]pyrimidine, imidazo[5,1-b]oxazole and imidazo[2,1-b]oxazole. Other specific examples of such ring systems include, for example, [1H]-pyrrolo[2,1-c]oxazine, [3H]-oxazolo[3,4-a]pyridine, [6H]-pyrrolo[2,1-c]oxazine and pyrido[2,1-c][1,4]oxazine. Other specific examples of 5/5-bicyclic ring systems are imidazooxazole or imidazothiazole, in particular imidazo[5,1-b]thiazole, imidazo[2,1-b]thiazole, imidazo[5,1-b]oxazole or imidazo[2,1-b]oxazole.

Particular examples of AR3a and AR3b include, for example, indoline, 1,3,4,6,9,9a-hexahydropyrido[2,1c][1,4]oxazin-8-yl, 1,2,3,5,8,8a-hexahydroimidazo[1,5a]pyridin-7-yl, 1,5,8,8a-tetrahydrooxazolo[3,4a]pyridin-7-yl, 1,5,6,7,8,8a-hexahydrooxazolo[3,4a]pyridin-7-yl, (7aS)[3H,5H]-1,7a-dihydropyrrolo[1,2c]oxazol-6-yl, (7aS)[5H]-1,2,3,7a-tetrahydropyrrolo[1,2c]imidazol-6-yl, (7aR)[3H,5H]-1,7a-dihydropyrrolo[1,2c]oxazol-6-yl, [3H,5H]-pyrrolo[1,2-c]oxazol-6-yl, [5H]-2,3-dihydropyrrolo[1,2-c]imidazol-6-yl, [3H,5H]-pyrrolo[1,2-c]thiazol-6-yl, [3H,5H]-1,7a-dihydropyrrolo[1,2-c]thiazol-6-yl, [5H]-pyrrolo[1,2-c]imidazol-6-yl, [1H]-3,4,8,8a-tetrahydropyrrolo[2,1-c]oxazin-7-yl, [3H]-1,5,8,8a-tetrahydrooxazolo[3,4-a]pyrid-7-yl, [3H]-5,8-dihydroxazolo[3,4-a]pyrid-7-yl and 5,8-dihydroimidazo[1,5-a]pyrid-7-yl.

Particular values for AR4 include, for example, pyrrolo[a]quinoline, 2,3-pyrroloisoquinoline, pyrrolo[a]isoquinoline, 1H-pyrrolo[1,2-a]benzimidazole, 9H-imidazo[1,2-a]indole, 5H-imidazo[2,1-a]isoindole,1H-imidazo[3,4-a]indole, imidazo[1,2-a]quinoline, imidazo[2,1-a]isoquinoline, imidazo[1,5-a]quinoline and imidazo[5,1-a]isoquinoline.

The nomenclature used is that found in, for example, "Heterocyclic Compounds (Systems with bridgehead nitrogen)", W. L. Mosby (Intercsience Publishers Inc., New York), 1961, Parts 1 and 2.

Where optional substituents are listed such substitution is preferably not geminal disubstitution unless stated otherwise. If not stated elsewhere suitable optional substituents for a particular group are those as stated for similar groups herein.

Suitable substituents on AR1, AR2, AR2a, AR2b, AR3, AR3a, AR3b, AR4, AR4a, CY1 and CY2 are (on an available carbon atom) up to three substituents independently selected from (1–4C)alkyl {optionally substituted by (preferably one) substituents selected independently from hydroxy, trifluoromethyl, (1–4C)alkyl $S(O)_q$— (q is 0, 1 or 2) (this last substituent preferably on AR1 only), (1–4C)alkoxy, (1–4C)alkoxycarbonyl, cyano, nitro, (1–4C)alkanoylamino, —CONRvRw or —NRvRw}, trifluoromethyl, hydroxy, halo, nitro, cyano, thiol, (1–4C)alkoxy, (1–4C)alkanoyloxy, dimethylaminomethyleneaminocarbonyl, di(N-(1–4C)alkyl)aminomethylimino, carboxy, (1–4C)alkoxycarbonyl, (1–4C)alkanoyl, (1–4C)

alkylSO$_2$amino, (24C)alkenyl {optionally substituted by carboxy or (1–4C)alkoxycarbonyl}, (2–4C)alkynyl, (1–4C) alkanoylamino, oxo (═O), thioxo (═S), (1–4C)alkanoylamino {the (1–4C)alkanoyl group being optionally substituted by hydroxy}, (1–4C)alkyl S(O)$_q$— (q is 0, 1 or 2) {the (1–4C)alkyl group being optionally substituted by one or more groups independently selected from cyano, hydroxy and (1–4C)alkoxy}, —CONRvRw or —NRvRw [wherein Rv is hydrogen or (1–4C)alkyl; Rw is hydrogen or (1–4C) alkyl].

Further suitable substituents on AR1, AR2, AR2a, AR2b, AR3, AR3a, AR3b, AR4, AR4a, CY1 and CY2 (on an available carbon atom), and also on alkyl groups (unless indicated otherwise) are up to three substituents independently selected from trifluoromethoxy, benzoylamino, benzoyl, phenyl {optionally substituted by up to three substituents independently selected from halo, (1–4C)alkoxy or cyano}, fluran, pyrrole, pyrazole, imidazole, triazole, pyrimidine, pyridazine, pyridine, isoxazole, oxazole, isothiazole, thiazole, thiophene, hydroxyimino(1–4C)alkyl, (1–4C) alkoxyimino(1–4C)alkyl, halo-(1–4C)alkyl, (1–4C) alkanesulfonamido, —SO$_2$NRvRw [wherein Rv is hydrogen or (1–4C)alkyl; Rw is hydrogen or (1–4C)alkyl].

Preferable optional substituents on Ar2b as 1,3-dioxolan-4-yl, 1,3-dioxan-4-yl, 1,3-dioxan-5-yl or 1,4-dioxan-2-yl are mono- or disubstitution by substituents independently selected from (1–4C)alkyl (including geminal disubstitution), (1–4C)alkoxy, (1–4C)alkylthio, acetamido, (1–4C)alkanoyl, cyano, trifluoromethyl and phenyl].

Preferable optional substituents on CY1 & CY2 are mono- or disubstitution by substituents independently selected from (1–4C)alkyl (including geminal disubstitution), hydroxy, (1–4C)alkoxy, (1–4C)alkylthio, acetamido, (1–4C)alkanoyl, cyano, and trifluoromethyl.

Suitable substituents on AR2, AR2a, AR2b, AR3, AR3a, AR3b, AR4 and AR4a are (on an available nitrogen atom, where such substitution does not result in quaternization) (1–4C)alkyl, (1–4C)alkanoyl {wherein the (1–4C)alkyl and (1–4C)alkanoyl groups are optionally substituted by (preferably one) substituents independently selected from cyano, hydroxy, nitro, trifluoromethyl, (1–4C)alkyl S(O)$_q$— (q is 0, 1 or 2), (1–4C)alkoxy, (1–4C)alkoxycarbonyl, (1–4C)alkanoylamino, —CONRvRw or —NRvRw [wherein Rv is hydrogen or (1–4C)alkyl; Rw is hydrogen or (1–4C)alkyl]}, (24C)alkenyl, (2–4C)alkynyl, (1–4C)alkoxycarbonyl or oxo (to form an N-oxide).

Suitable pharmaceutically-acceptable salts include acid addition salts such as methanesulfonate, fumarate, hydrochloride, citrate, maleate, tartrate and (less preferably) hydrobromide. Also suitable are salts formed with phosphoric and sulfuric acid. In another aspect suitable salts are base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine, tris-(2-hydroxyethyl)amine, N-methyl d-glucamine and amino acids such as lysine. There may be more than one cation or anion depending on the number of charged functions and the valency of the cations or anions. A preferred pharmaceutically-acceptable salt is the sodium salt.

However, to facilitate isolation of the salt during preparation, salts which are less soluble in the chosen solvent may be preferred whether pharmaceutically-acceptable or not.

The compounds of the formula (I) may be administered in the form of a pro-drug which is broken down in the human or animal body to give a compound of the formula (I). A prodrug may be used to alter or improve the physical and/or pharmacokinetic profile of the parent compound and can be formed when the parent compound contains a suitable group or substituent which can be derivatised to form a prodrug. Examples of pro-drugs include in-vivo hydrolysable esters of a compound of the formula (I) or a pharmaceutically-acceptable salt thereof.

Various forms of prodrugs are known in the art, for examples see:

a) Design of Prodrugs, edited by H. Bundgaard, (Elsevier, 1985) and Methods in Enzymology, Vol. 42, p. 309–396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p. 113–191 (1991);

c) H. Bundgaard, Advanced Drug Delivery Reviews, 8, 1–38 (1992);

d) H. Bundgaard, et al., Journal of Pharmaceutical Sciences, 77, 285 (1988); and e) N. Kakeya, et al., Chem Pharm Bull, 32, 692 (1984).

An in-vivo hydrolysable ester of a compound of the formula (I) or a pharmaceutically-acceptable salt thereof containing carboxy or hydroxy group is, for example, a pharmaceutically-acceptable ester which is hydrolysed in the human or animal body to produce the parent acid or alcohol. Suitable pharmaceutically-acceptable esters for carboxy include (1–6C)alkoxymethyl esters for example methoxymethyl, (1–6C)alkanoyloxymethyl esters for example pivaloyloxymethyl, phthalidyl esters, (3–8C)cycloalkoxycarbonyloxy(1–6C)alkyl esters for example 1-cyclohexylcarbonyloxyethyl; 1,3-dioxolan-2-onylmethyl esters for example 5-methyl-1,3-dioxolan-2-ylmethyl; and (1–6C) alkoxycarbonyloxyethyl esters for example 1-methoxycarbonyloxyethyl and may be formed at any carboxy group in the compounds of this invention.

An in-vivo hydrolysable ester of a compound of the formula (I) or a pharmaceutically-acceptable salt thereof containing a hydroxy group or groups includes inorganic esters such as phosphate esters (including phosphoramidic cyclic esters) and α-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethylpropionyloxymethoxy. A selection of in-vivo hydrolysable ester forming groups for hydroxy include (1–10C)alkanoyl, benzoyl, phenylacetyl and substituted benzoyl and phenylacetyl, (1–10C)alkoxycarbonyl (to give alkyl carbonate esters), di-(1–4C)alkylcarbamoyl and N-(di-(1–4C)alkylaminoethyl)-N-(1–4C)alkylcarbamoyl (to give carbamates), di-(1–4C)alkylaminoacetyl and carboxyacetyl. Examples of substituents on benzoyl include chloromethyl or aminomethyl, (1–4C)alkylaminomethyl and di-((1–4C)alkyl)aminomethyl, and morpholino or piperazino linked from a ring nitrogen atom via a methylene linking group to the 3- or 4-position of the benzoyl ring.

Certain suitable in-vivo hydrolysable esters of a compound of the formula (I) are described within the definitions listed in this specification, for example esters described by the definition (Rc2d), and some groups within (Rc2c). Suitable in-vivo hydrolysable esters of a compound of the formula (I) are described as follows. For example, a 1,2-diol may be cyclised to form a cyclic ester of formula (PD1) or a pyrophosphate of formula (PD2):

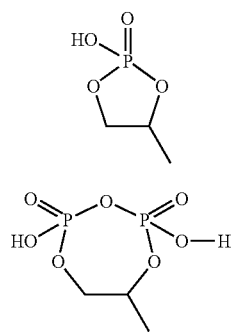
(PD1)

(PD2)

Particularly interesting are such cyclised pro-drugs when the 1,2-diol is on a (1–4C)alkyl chain linked to a carbonyl group in a substituent of formula Rc borne by a nitrogen atom in (TC4). Esters of compounds of formula (I) wherein the HO— function/s in (PD1) and (PD2) are protected by (1–4C)alkyl, phenyl or benzyl are useful intermediates for the preparation of such pro-drugs.

Further in-vivo hydrolysable esters include phosphoramidic esters, and also compounds of formula (I) in which any free hydroxy group independently forms a phosphoryl (npd is 1) or phosphiryl (npd is 0) ester of the formula (PD3):

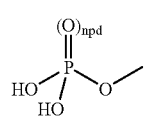
(PD3)

Useful intermediates for the preparation of such esters include compounds containing a group/s of formula (PD3) in which either or both of the —OH groups in (PD3) is independently protected by (1–4C)alkyl (such compounds also being interesting compounds in their own right), phenyl or phenyl-(1–4C)alkyl (such phenyl groups being optionally substituted by 1 or 2 groups independently selected from (1–4C)alkyl, nitro, halo and (1–4C)alkoxy).

Thus, prodrugs containing groups such as (PD I), (PD2) and (PD3) may be prepared by reaction of a compound of formula (I) containing suitable hydroxy group/s with a suitably protected phosphorylating agent (for example, containing a chloro or dialkylamino leaving group), followed by oxidation (if necessary) and deprotection.

When a compound of formula (I) contains a number of free hydroxy group, those groups not being converted into a prodrug functionality may be protected (for example, using a t-butyl-dimethylsilyl group), and later deprotected. Also, enzymatic methods may be used to selectively phosphorylate or dephosphorylate alcohol functionalities.

Other interesting in-vivo hydrolysable esters include, for example, those in which Rc is defined by, for example, $R^{14}C(O)O(1–6C)alkyl-CO$— (wherein $R^{14}$ is for example, benzyloxy-(1–4C)alkyl, or phenyl). Suitable substituents on a phenyl group in such esters include, for example, 4-(1–4C)piperazino-(1–4C)alkyl, piperazino-(1–4C)alkyl and morpholino-(1–4C)alkyl.

Where pharmaceutically-acceptable salts of an in-vivo hydrolysable ester may be formed this is achieved by conventional techniques. Thus, for example, compounds containing a group of formula (PD1), (PD2) and/or (PD3) may ionise (partially or fully) to form salts with an appropriate number of counter-ions. Thus, by way of example, if an in-vivo hydrolysable ester prodrug of a compound of formula (I) contains two (PD3) groups, there are four HO—P— functionalities present in the overall molecule, each of which may form an appropriate salt (i.e. the overall molecule may form, for example, a mono-, di-, tri- or tetra-sodium salt).

The compounds of the present invention have a chiral centre at the C-5 position of the oxazolidinone ring. The pharmaceutically active enantiomer is of the formula (IA):

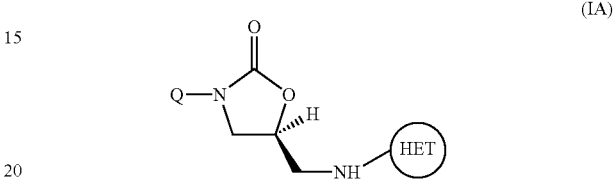
(IA)

The present invention includes the pure enantiomer depicted above or mixtures of the 5R and 5S enantiomers, for example a racemic mixture. If a mixture of enantiomers is used, a larger amount (depending upon the ratio of the enantiomers) will be required to achieve the same effect as the same weight of the pharmaceutically active enantiomer. For the avoidance of doubt the enantiomer depicted above is the 5(S) enantiomer.

Furthermore, some compounds of the formula (I) may have other chiral centres. It is to be understood that the invention encompasses all such optical and diastereo-isomers, and racemic mixtures, that possess antibacterial activity. It is well known in the art how to prepare optically-active forms (for example by resolution of the racemic form by recrystallisation techniques, by chiral synthesis, by enzymatic resolution, by biotransformation or by chromatographic separation) and how to determine antibacterial activity as described hereinafter.

The invention relates to all tautomeric forms of the compounds of the formula (I) that possess antibacterial activity.

It is also to be understood that certain compounds of the formula (I) can exist in solvated as well as unsolvated forms such as, for example, hydrated forms. It is to be understood that the invention encompasses all such solvated forms which possess antibacterial activity.

It is also to be understood that certain compounds of the formula (I) may exhibit polymorphism, and that the invention encompasses all such forms which possess antibacterial activity.

As stated before, we have discovered a range of compounds that have good activity against a broad range of Gram-positive pathogens including organisms known to be resistant to most commonly used antibiotics. Physical and/or pharmacokinetic properties, for example increased stability to mammalian peptidase metabolism and a favourable toxicological profile are important features. The following compounds possess favourable physical and/or pharmacokinetic properties and are preferred.

Particularly preferred compounds of the invention comprise a compound of formula (I) or of formula (IP), or a pharmaceutically-acceptable salt or an in-vivo hydrolysable ester thereof, wherein the substituents Q, HET, T, $T^1$ and other substituents mentioned above have values disclosed hereinbefore, or any of the following values (which may be used where appropriate with any of the definitions and embodiments disclosed hereinbefore or hereinafter):

Preferably Q is selected from Q1, Q2, Q4, Q6 and Q9; especially Q1, Q2 and Q9; more particularly Q1 and Q2; and most preferably Q is Q1.

Preferably T is selected from (TAf), (TDb) or (TC); especially groups (TAf2), (TCb) and (TCc); more particularly (TC2), (TC3) and (TC4); and most preferably (TC5), (TC7) or (TC9), and most particularly (TC9) and (TC5). Especially preferred is each of these values of T when present in Q1 and Q2, particularly in Q1.

Preferable values for other substituents (which may be used where appropriate with any of the definitions and embodiments disclosed hereinbefore or hereinafter) are:—

(a0) In one embodiment HET is a 6-membered heteroaryl as defined herein, and in another embodiment HET is a 5-membered heteroaryl as defined herein.

(a) When HET is a 6-membered heteroaryl as defined herein, preferably HET is pyrimidine, pyridazine or pyrazine; more preferably HET is pyrimidin-2-yl, pyridazin-3-yl or pyrazin-2-yl; preferably HET is unsubstituted.

(b) When HET is a 5-membered heteroaryl as defined herein, preferably HET is not thiazole; preferably HET is pyrazole, imidazole, oxazole, isoxazole, 1,2,4-oxadiazole, 1,2,5-oxadiazole, 1,3,4-oxadiazole, isothiazole, 1,2,3-thiadiazole, 1,2,4-thiadiazole, 1,2,5-thiadiazole, 1,3,4-thiadiazole, 1,2,3-triazole or 1,2,4-triazole.

(c) Yet more preferably HET is pyrazol-3-yl, imidazol-2-yl (optionally 3-methyl substituted), imidazol-4-yl (optionally 1-methyl substituted), oxazol-2-yl, isoxazol-3-yl, isoxazol-5-yl, 1,2,5-oxadiazol-3-yl, 1,2,4-oxadiazol-3-yl, 1,3,4-oxadiazol-2-yl, isothiazol-3-yl, isothiazol-5-yl, 1,2,3-thiadiazol-4-yl, 1,2,4-thiadiazol-3-yl, 1,2,4-thiadiazol-S-yl, 1,2,5-thiadiazol-3-yl or 1,3,4-thiadiazol-2-yl.

(d) Further preferred as HET is isoxazol-3-yl, isoxazol-5-yl, 1,2,5-oxadiazol-3-yl, 1,2,4-oxadiazol-3-yl, 1,3,4-oxadiazol-2-yl, isothiazol-3-yl, isothiazol-5-yl, 1,2,3-thiadiazol-4-yl, 1,2,4-thiadiazol-3-yl, 1,2,4-thiadiazol-5-yl, 1,2,5-thiadiazol-3-yl or 1,3,4-thiadiazol-2-yl.

(e) Particularly preferred as HET is isoxazol-3-yl, isoxazol-5-yl, 1,2,5-oxadiazol-3-yl, isothiazol-3-yl, isothiazol-5-yl, 1,2,3-thiadiazol-4-yl, 1,2,4-thiadiazol-3-yl, 1,2,4-thiadiazol-5-yl, 1,2,5-thiadiazol-3-yl or 1,3,4-thiadiazol-2-yl.

(f) Most preferred is HET as isoxazole (optionally substituted as disclosed hereinbefore), particularly isoxazol-3-yl.

(g) Preferably HET is unsubstituted.

(h) Preferably $R^{6p}$ is hydrogen;

(i) Preferably $R^{4p}$ and $R^{5p}$ are independently selected from hydrogen, (1–4C)alkyl, carboxy, (1–4C)alkoxycarbonyl, hydroxymethyl, (1–4C)alkoxymethyl or carbamoyl;

(j) More preferably $R^{4p}$ and $R^{5p}$ are hydrogen;

(k) Preferably $R^2$ and $R^3$ are hydrogen or fluoro;

(l) In one aspect of the invention more preferably one of $R^2$ and $R^3$ is hydrogen and the other fluoro. In another aspect of the invention both $R^2$ and $R^3$ are fluoro;

(m) Preferably >A—B— is of the formula >C=CH— (i.e. $R^a$ is preferably hydrogen) or >N—CH$_2$—;

(n) Preferably D is O or NR$^{7p}$;

(O) Preferably $R^{7p}$ is ARp, $R^{10p}CO$—, $R^{10p}SO_2$—, $R^{10p}CS$—;

(p) More preferably $R^{7p}$ is ARp (most preferably benzyl, pyrimidyl, pyridinyl, pyridazinyl or pyrazinyl) or $R^{10p}CO$—;

(q) Particularly $R^{7p}$ is $R^{10p}CO$—;

(q1) Especially preferred is $R^{10p}CO$— (or $R^{13}CO$—) wherein $R^{10p}$ (or $R^{13}$) is (1–10)alkyl optionally substituted by hydroxy or (1–4C)alkylS(O)$_q$— (wherein q is 0, 1 or 2), wherein the (1–4C)alkyl group is optionally substituted as defined herein for this particular substituent;

(r) Preferably ARp is 5- or 6-membered heteroaryl; more preferably ARp is 6-membered heteroaryl, such as pyridinyl;

(s) Preferred substituents for phenyl and carbon atoms in heteroaryl (mono- and bicyclic) ring systems in ARp, $R^{11p}$ and $R^i$ include halo, (1–4C)alkyl, hydroxy, nitro, amino, cyano, (1–4C)alkylS(O)$_p$— and (1–4C)alkoxy;

(t) Preferably the optionally substituted ring systems in ARp, $R^{11p}$ and $R^i$ are unsubstituted;

(u) In another embodiment in the definition of $R^{10p}$ in (PC) of embodiment (IP), 1,3-dioxolan-4-yl and 1,4-dioxan-2-yl are excluded.

(v) In one aspect of the invention, preferably $R^{10p}$ is (1–4C)alkoxycarbonyl, hydroxy(1–4C)alkyl, (1–4C)alkyl (optionally substituted by one or two hydroxy groups, or by an (1–4C)alkanoyl group), (1–4C)alkylamino, dimethylamino (1–4C)alkyl, (1–4C)alkoxymethyl, (1–4C)alkanoylmethyl, (1–4C)alkanoyloxy(1–4C)alkyl, (1–5C)alkoxy or 2-cyanoethyl;

(w) In one aspect of the invention, more preferably $R^{10p}$ is 1,2-dihydroxyethyl, 1,3-dihydroxyprop-2-yl, 1,2,3-trihydroxyprop-1-yl, methoxycarbonyl, hydroxymethyl, methyl, methylamino, dimethylaminomethyl, methoxymethyl, acetoxymethyl, methoxy, methylthio, naphthyl, tert-butoxy or 2-cyanoethyl;

(x) In one aspect of the invention, particularly $R^{10p}$ is 1,2-dihydroxyethyl, 1,3-dihydroxyprop-2-yl or 1,2,3-trihydroxyprop-1-yl;

(y) In another aspect of the invention preferably $R^{10p}$ is hydrogen, (1–10C)alkyl [optionally substituted by one or more hydroxy] or $R^{11p}C(O)O(1–6C)alkyl$.

(z) In another aspect of the invention, more preferably $R^{10p}$ is hydrogen, hydroxymethyl, 1,2-dihydroxyethyl or acteoxyacetyl; and/or Rc2c is (1–10C)alkyl optionally substituted by (1–4C)alkyl S(O)$_q$-(q is 0–2), optionally substituted as in claim 1.

(aa) Preferably $R^{11p}$ is (1–10C)alkyl;

(ab) Preferred optional substituents for (1–10C)alkyl in $R^{11p}$ are hydroxy, cyano, amino, (1–4C)alkylamino, di((1–4C)alkyl)amino, (1–4C)alkylS(O)$_p$ (wherein p is 1 or 2), carboxy, (1–4C)alkoxycarbonyl, (1–4C)alkoxy, piperazino or morpholino;

(ac) Preferred optional substituents for (1–6C)alkyl in $R^{12p}$ are hydroxy, (1–4C)alkoxy, cyano, amino, (1–4C)alkylamino, di((1–2C)alkyl)amino, (1–4C)alktlS(O)P— (wherein p is 1 or 2);

(ad) Preferably 5- or 6-membered heteroaryl in $R^{11p}$ is pyridinyl or imidazol-1-yl;

(ae) Preferably $R^{12p}$ is (1–6C)alkyl; most preferably $R^{12p}$ is tert-butylor methyl;

(af) Preferably $R^{13p}$ is cyano or fluoro;

(ag) Preferably $R^{14p}$ is hydrogen;

(ah) Preferably CYp is naphthoxy, especially naphth-1-oxy or naphth-2-oxy.

Where preferable values are given for substituents in a compound of formula (IP), the corresponding substituents in a compound of formula (I) have the same preferable values (thus, for example, Rc and $R^{13}$ in formula (I) correspond with $R^{7p}$ and $R^{10p}$ in formula (IP), and similarly for groups D and G). The preferred values of $R^{7p}$, for example, defined with reference to (IP) are also preferred values of Rc and may be used as preferred values of Rc in any compound of formula (I). For compounds of formula (I) preferred values for Rc are those in group (Rc2) when present in any of the definitions herein containing Rc—for example when present in compounds in which there is a (TC5) or (TC9) ring system. The preferred values for $R^{10p}$ listed above for compounds of formula (IP) are also preferred values for $R^{13}$ in compounds of formula (I). In the definition of (Rc2c) the AR2a, AR2b, AR3a and AR3b versions of AR2 and AR3 containing groups are preferably excluded.

In another aspect, HET is a C-linked 5-membered heteroaryl ring containing 2 or 3 heteroatoms independently selected from N, O and S (with the proviso that there are no O—O, O—S, S—S or N—S bonds), which ring is optionally substituted on any available C atom (provided that when a N atom is adjacent to the NH-link, there is no substitution on any C atom that is adjacent to this N atom) by 1 or 2 substituents independently selected from (1–4C)alkyl, amino, (1–4C)alkylamino, (1–4C)alkoxy and halogen, and/or on an available N atom (provided that the ring is not thereby quaternised), by (1–4C)alkyl.

In another aspect, HET is selected from the formulae (HET1) to (HET3) below:—

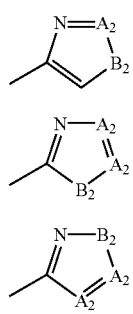

wherein $A_2$ is carbon or nitrogen and $B_2$ is O S or N (with a maximum of 3 hetero atoms per ring), with carbon or nitrogen ring atoms being optionally substituted as described for HET hereinbefore (preferably with no substitution on any carbon atom that is adjacent to the specified N atom).

The above HET definitions are especially preferred in embodiment (IP).

Especially preferred compounds of the present invention are of the formula (IB):

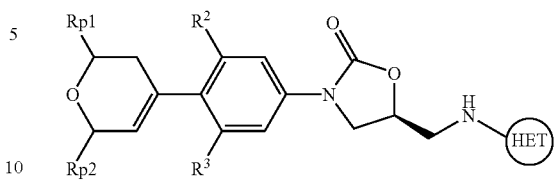

wherein HET is isoxazol-3-yl, isoxazol-5-yl, 1,2,4-oxadiazol-3-yl, isothiazol-3-yl, 1,2,4-thiadiazol-3-yl or 1,2,5-thiadiazol-3-yl;

$R^2$ and $R^3$ are independently hydrogen or fluoro; and Rp 1 and Rp2 are independently hydrogen, hydroxy, bromo, (1–4C)alkyl, carboxy, (1–4C)alkoxycarbonyl, hydroxymethyl, (1–4C)alkoxymethyl or carbamoyl; or pharmaceutically-acceptable salts thereof.

Further especially preferred compounds of the invention are of the formula (IB) wherein HET is isoxazol-3-yl, isoxazol-5-yl, 1,2,4-oxadiazol-3-yl, isothiazol-3-yl, 1,2,4-thiadiazol-3-yl or 1,2,5-thiadiazol-3-yl; $R^2$ and $R^3$ are independently hydrogen or fluoro; and Rp1 and Rp2 are independently hydrogen, AR-oxymethyl or AR-thiomethyl (wherein AR is phenyl, phenyl-(1–4C)alkyl, naphthyl, furan, pyrrole, pyrazole, imidazole, triazole, pyrimidine, pyridazine, pyridine, isoxazole, oxazole, isothiazole, thiazole or thiophene); or pharmaceutically-acceptable salts thereof.

Of the above especially preferred compounds of the invention of the formula (IB), particularly preferred compounds are those wherein Rp 1 and Rp2 are hydrogen are particularly preferred.

Further, especially preferred compounds of the invention are of the formula (IC):

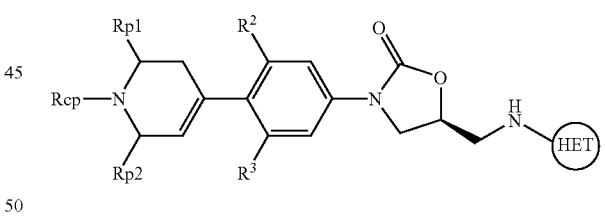

wherein HET is isoxazol-3-yl, isoxazol-5-yl, 1,2,4-oxadiazol-3-yl, isothiazol-3-yl, 1,2,4-thiadiazol-3-yl or 1,2,5-thiadiazol-3-yl; $R^2$ and $R^3$ are independently hydrogen or fluoro; Rp1 and Rp2 are independently hydrogen, AR-oxymethyl or AR-thiomethyl (wherein AR is phenyl, phenyl-(1–4C)alkyl, naphthyl, firan, pyrrole, pyrazole, imidazole, triazole, pyrimidine, pyridazine, pyridine, isoxazole, oxazole, isothiazole, thiazole or thiophene), (1–4C)alkyl, carboxy, (1–4C) alkoxycarbonyl, hydroxymethyl, (1–4C)alkoxymethyl or carbamoyl and Rcp is cyano, pyrimidin-2-yl, 2-cyanoethenyl, 2-cyano-2-((1–4C)alkyl)ethenyl or Rcp is of the formula $R^{10p}CO—$, $R^{10p}SO_2—$ or $R^{10p}CS—$ (wherein $R^{10p}$ is hydrogen, (1–5C)alkyl [optionally substituted by one or more groups each independently selected from hydroxy and amino, or optionally monosubstituted by (1–4C)alkoxy, (1–4C)alkylS(O)$_q$—, (1–4C)alkylamino, (1–4C)alkanoyl, naphthoxy, (2–6C)alkanoylamino or (1–4C)alkylS(O)$_p$NH— wherein p is 1 or 2 and q is 0, 1 or 2], imidazole, triazole, pyrimidine, pyridazine, pyridine, isoxazole, oxazole, isothiazole, thiazole, pyridoimidazole, pyrimidoimidazole, quinoxaline, quinazoline, phthalazine, cinnoline or naphthyridine, or R$^{10p}$ is of the formula R$^{11p}$C(O)O(1–6C)alkyl wherein R$^{11p}$ is (1–6C)alkyl), or Rcp is of the formula RfC(=O)C(=O)— herein Rf is (1–6C)alkoxy; or pharmaceutically-acceptable salts thereof.

Of the above especially preferred compounds of the invention of the formula (IC), those wherein HET is isoxazol-3-yl, isoxazol-5-yl, 1,2,4-oxadiazol-3-yl, isothiazol-3-yl, 1,2,4-thiadiazol-3-yl or 1,2,5-thiadiazol-3-yl; R$^2$ and R$^3$ are independently hydrogen or fluoro; Rp1 and Rp2 are independently hydrogen, AR-oxymethyl or AR-thiomethyl (wherein AR is phenyl, phenyl-(1–4C)alkyl, naphthyl, furan, pyrrole, pyrazole, imidazole, triazole, pyrimidine, pyridazine, pyridine, isoxazole, oxazole, isothiazole, thiazole or thiophene), (1–4C)alkyl, carboxy, (1–4C)alkoxycarbonyl, hydroxymethyl, (1–4C)alkoxymethyl or carbamoyl and Rcp is cyano, pyrimidin-2-yl, 2-cyanoethenyl, 2-cyano-2-((1–4C)alkyl)ethenyl or Rcp is of the formula R$^{10p}$CO—, R$^{10p}$SO$_2$— or R$^{10p}$CS— (wherein R$^{10p}$ is hydrogen, (1–5C)alkyl [optionally substituted by one or more groups each independently selected from hydroxy and amino, or optionally monosubstituted by (1–4C)alkoxy, (1–4C)alkylS(O)$_q$, (1–4C)alkylamino, (1–4C)alkanoyl, (2–6C)alkanoylamino or (1–4C)alkylS(O)$_p$NH— wherein p is 1 or 2 and q is 0, 1 or 2], pyridine, or R$^{10p}$ is of the formula R$^{11p}$C(O)O(1–6C)alkyl wherein R$^{11p}$ is (1–6C)alkyl), or Rcp is of the formula RfC(=O)C(=O)— wherein Rf is (1–6C)alkoxy; or pharmaceutically-acceptable salts thereof are further preferred.

Of the above especially preferred compounds of the invention of the formula (IC), particularly preferred compounds are those wherein HET is isoxazol-3-yl, isoxazol-5-yl, 1,2,4-oxadiazol-3-yl, isothiazol-3-yl, 1,2,4-thiadiazol-3-yl or 1,2,5-thiadiazol-3-yl; R$^2$ and R$^3$ are independently hydrogen or fluoro; Rp1 and Rp2 are hydrogen, and Rcp is pyridin-2-yl (optionally substituted with cyano) or Rcp is of the formula R$^{10p}$CO— (wherein R$^{10p}$ is hydrogen, 1,3-dioxolan-4-yl (optionally disubstituted with (1–4C)alkyl) or (1–5C)alkyl [optionally substituted by one or more hydroxy groups] or R$^{10p}$ is of the formula R$^{11p}$C(O)O(1–6C)alkyl wherein R$^{11p}$ is (1–6C)alkyl)); or pharmaceutically-acceptable salts thereof.

Of the above especially preferred compounds of the invention of the formula (IC), particularly preferred compounds are those wherein Rcp is of the formula R$^{10p}$CO— (wherein R$^{10p}$ is hydrogen, 1,3-dioxolan-4-yl (optionally disubstituted with (1–4C)alkyl) or (1–5C)alkyl [substituted by two hydroxy groups]; or pharmaceutically-acceptable salts thereof.

In another aspect of the invention particularly preferred compounds of the invention are of the formula (IC) wherein HET is isoxazol-3-yl; R$^2$ and R$^3$ are independently hydrogen or fluoro; Rp1 and Rp2 are hydrogen and Rcp is R$^{10p}$CO— (wherein R$^{10p}$ is hydrogen, (1–5C)alkyl [optionally substituted by one or two hydroxy groups], or R$^{10p}$ is of the formula R$^{11p}$C(O)O(1–6C)alkyl (wherein R$^{11p}$ is (1–6C)alkyl)); and pharmaceutically-acceptable salts thereof.

In another aspect of the invention all of the compounds of formula (IB) or (IC) described above are further preferred when HET is isoxazol-3-yl, isothiazol-3-yl or 1,2,5-thiadiazol-3-yl.

In yet another aspect the invention relates to all of the compounds of formula (IB) or (IC) described above wherein HET is isoxazol-3-yl or 1,2,4-oxadiazol-3yl.

In yet another aspect the invention relates to all of the compounds of formula (IB) or (IC) described above wherein HET is isoxazol-3-yl.

In another aspect of the invention there are provided preferred compounds of the formula (IP) wherein HET is isoxazol-3-yl, 1,2,4-oxadiazol-3-yl, isothiazol-3-yl, 1,2,5-thiadiazol-3-yl; >A—B— is >N—CH$_2$— and D is NR$^{7p}$ (or D is O) wherein Rep is a 6-membered heteroaryl ring containing 1, 2 or 3 ring nitrogen atoms as the only ring heteroatoms, linked via a ring carbon atom and optionally substituted on a ring carbon atom by one, two or three substituents independently selected from (1–4C)alkyl, halo, trifluoromethyl, (1–4C)alkyl S(O)$_q$—, (wherein q is 0, 1 or 2), (1–4C)alkylS(O)$_2$amino, (1–4C)alkanoylamino, carboxy, hydroxy, amino, (1–4C)alkylamino, di-(1–4C)alkylamino, (1–4C)alkoxycarbonyl, carbamoyl, N-(1–4C)alkylcarbamoyl, di-(N-(1–4C)alkyl)carbamoyl, (1–4C)alkoxy, cyano or nitro; or pharmaceutically-acceptable salts thereof.

In yet another aspect the invention relates to all of the compounds of formula (IP) described immediately above wherein >A—B— is >N—CH$_2$— and D is NR$^{7p}$ and wherein HET is isoxazol-3-yl, isoxazol-5-yl, 1,2,4-oxadiazol-3-yl, isothiazol-3-yl, 1,2,4-thiadiazol-3-yl or 1,2,5-thiadiazol-3-yl.

In all of the above aspects and preferred compounds of formula (IB) or (IC), in-vivo hydrolysable esters are preferred where appropriate, especially phosphoryl esters (as defined by formula (PD3) with npd as 1).

In all of the above definitions the preferred compounds are as shown in formula (IA), i.e. the pharmaceutically active (5(S)) enantiomer.

Particular compounds of the present invention include the following:—

5(S)-Isoxazol-3-ylaminomethyl-3-(3-fluoro-4-(3,6-dihydro-(2H)-pyran-4-yl)phenyl)oxazolidin-2-one;

5(S)-Isoxazol-3-ylaminomethyl-3-(3-fluoro-4-morpholinophenyl)-oxazolidin-2-one;

5(S)-Isoxazol-3-ylaminomethyl-3-[3-fluoro-4-(1-hydroxyacetyl-1,2,5,6-tetrahydropyrid-4-yl)phenyl]oxazolidin-2-one;

5(S)-Isoxazol-3-ylaminomethyl-3-[3-fluoro-4-(1-(2(S),3-dihydroxypropanoyl)-1,2,5,6-tetrahydropyrid-4-yl)phenyl]oxazolidin-2-one;

5(S)-Isoxazol-3-ylaminomethyl-3-(3,5-difluoro-4-(1-hydroxyacetyl-1,2,5,6-tetrthydropyrid-4-yl)phenyl)oxazolidin-2-one;

5(S)-Isoxazol-3-ylaminomethyl-3-(3,5-difluoro-4-(1-(2(S),3-dihydroxypropanoyl)-1,2,5,6-tetrahydropyrid-4-yl)phenyl)oxazolidin-2-one;

5(S)-(Isoxazol-3-ylaminomethyl)-3-(1-hydroxyacetyl-1,2,5,6-tetrahydropyrid-4-yl)phenyl)oxazolidin-2-one;

5(S)-(Isoxazol-3-ylaminomethyl)-3-(1-(2(S),3-dihydroxypropanoyl)-1,2,5,6-tetrahydropyrid-4-yl)phenyl)oxazolidin-2-one.

Thus, most particularly preferred Examples are Example Nos. 1, 2, 5, 6, 34, 35, 46 and 48, or pharmaceutically-acceptable salts thereof. Particularly preferred salts are the sodium salts. In-vivo hydrolysable esters of Examples 5, 6, 34, 35, 46 and 48 are also preferred, especially phosphoryl esters.

Process Section:

In a further aspect the present invention provides a process for preparing a compound of formula (I) or a pharmaceutically-acceptable salt or an in-vivo hydrolysable ester thereof. It will be appreciated that during certain of the following processes certain substituents may require protection to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Thus, if reactants include, for example, groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The protecting groups may be removed at any convenient stage in the synthesis using conventional techniques well known in the chemical art.

A compound of the formula (I), or a pharmaceutically-acceptable salt or an in vivo hydrolysable ester thereof, may be prepared by any process known to be applicable to the preparation of chemically-related compounds. Such processes, when used to prepare a compound of the formula (I), or a pharmaceutically-acceptable salt or an in vivo hydrolysable ester thereof, are provided as a further feature of the invention and are illustrated by the following representative examples. Necessary starting materials may be obtained by standard procedures of organic chemistry (see, for example, Advanced Organic Chemistry (Wiley-Interscience), Jerry March). The preparation of such starting materials is described within the accompanying non-limiting Examples (in which, for example, 3,5-difluorophenyl, 3-fluorophenyl and (des-fluoro)phenyl containing intermediates may all be prepared by analagous procedures; or by alternative procedures—for example, the preparation of (T group)-(fluoro) phenyl intermediates by reaction of a (fluoro)phenylstannane with, for example, a pyran or (tetrahydro)pyridine compound, may also be prepared by anion chemistry (see, for example, WO97/30995). Alternatively, necessary starting materials are obtainable by analogous procedures to those illustrated which are within the ordinary skill of an organic chemist. Information on the preparation of necessary starting materials or related compounds (which may be adapted to form necessary starting materials) may also be found in the following patent and application Publications, the contents of the relevant process sections of which are hereby incorporated herein by reference:

WO99/02525; WO98/54161; WO97/37980; WO97/30981 (& U.S. Pat. No. 5,736,545); WO97/21708 (& U.S. Pat. No. 5,719,154); WO97/10223; WO97/09328; WO96/35691; WO96/23788; WO96/15130; WO96/13502; WO95/25106 (& U.S. Pat. No. 5,668,286); WO95/14684 (& U.S. Pat. No. 5,652,238); WO95/07271 (& U.S. Pat. No. 5,688,792); WO94/13649; WO94/01110; WO93/23384 (& U.S. Pat. No. 5,547,950 & U.S. Pat. No. 5,700,799); WO93/09103 (& U.S. Pat. No. 5,565,571, U.S. Pat. No. 5,654,428, U.S. Pat. No. 5,654,435, U.S. Pat. No. 5,756,732 & U.S. Pat. No. 5,801,246); U.S. Pat. No. 5,231,188; U.S. Pat. No. 5,247,090; U.S. Pat. No. 5,523,403; WO97/27188; WO97/30995; WO97/31917; WO98/01447; WO98/01446; WO99/10342; WO99/10343; WO99/11642; European Patent Application Nos. 0,359,418 and 0,609,905; 0,693,491 A1 (& U.S. Pat. No. 5,698,574); 0,694,543 A1 (& AU 24985/95); 0,694,544 A1 (& CA 2,154,024); 0,697,412 A1 (& U.S. Pat. No. 5,529,998); 0,738,726 A1 (& AU 50735/96); 0,785,201 A1 (& AU 10123/97); German Patent Application Nos. DE 195 14 313 A1 (& U.S. Pat. No. 5,529,998); DE 196 01 264 A1 (& AU 10098/97); DE 196 01 265 A1 (& AU 10097/97); DE 196 04 223 A1 (& AU 12516/97); DE 196 49 095 A1 (& AU 12517/97).

The following patent and application Publications may also provide useful information and the contents of the relevant process sections are hereby incorporated herein by reference:

FR 2458547; FR 2500450 (& GB 2094299, GB 2141716 & U.S. Pat. No. 4,476,136); DE 2923295 (& GB 2028306, GB 2054575, U.S. Pat. No. 4,287,351, U.S. Pat. No. 4,348,393, U.S. Pat. No. 4,413,001, U.S. Pat. No. 4,435,415 & U.S. Pat. No. 4,526,786), DE 3017499 (& GB 2053196, U.S. Pat. No. 4,346,102 & U.S. Pat. No. 4,372,967); U.S. Pat. No. 4,705,799; European Patent Application Nos. 0,312,000; 0,127,902; 0,184,170; 0,352,781; 0,316,594;

The skilled organic chemist will be able to use and adapt the information contained and referenced within the above references to obtain necessary starting materials.

Thus, the present invention also provides that the compounds of the formulae (I) and pharmaceutically-acceptable salts and in vivo hydrolysable esters thereof, can be prepared by a process (a) to (d) as follows (wherein the variables are as defined above unless otherwise stated):

(wherein the variables are as defined above unless otherwise stated):

(a) by modifying a substituent in or introducing a substituent into another compound of formula (I);

(b) by reaction of a compound of formula (II):

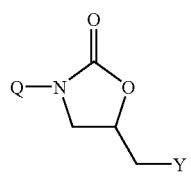

(II)

wherein Y is either (i) hydroxy; or (ii) a displaceable group with a compound of the formula (III):

HN(Pg)—HET   (III)

wherein Pg is a suitable protecting group; or (c) by reaction of a compound of the formula (IV)

Q—Z   (IV)

wherein Z is an isocyanate, amine or urethane group with an epoxide of the formula (V):

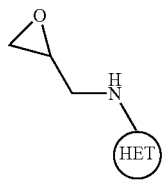

(V)

(d) by reaction of a compound of formula (II) wherein Y is an amino group with a compound of the formula (IIIA):

Lg—HET   (IIIA)

wherein Lg is a leaving group; and thereafter if necessary:

(i) removing any protecting groups; (ii) forming a pharmaceutically-acceptable salt; (iii) forming an in-vivo hydrolysable ester.

Deprotection, salt formation or in-vivo hydrolysable ester formation may each be provided as a specific final process step.

Where Y is a displaceable group, suitable values for Y are for example, a halogeno or sulfonyloxy group, for example a chloro, bromo, methanesulfonyloxy or toluene-4-sulfonyloxy group.

General guidance on reaction conditions and reagents may be obtained in Advanced Organic Chemistry, 4$^{th}$ Edition, Jerry March (publisher: J. Wiley & Sons), 1992.

Necessary starting materials may be obtained by standard procedures of organic chemistry, such as described in this process section, in the Examples section or by analogous procedures within the ordinary skill of an organic chemist. Certain references are also provided which describe the preparation of certain suitable starting materials, for example International Patent Application Publication No. WO 97/37980, the contents of which are incorporated here by reference. Processes analogous to those described in the references may also be used by the ordinary organic chemist to obtain necessary starting materials.

(a) Methods for converting substituents into other substituents are known in the arL For example an alkylthio group may be oxidised to an alkylsulfinyl or alkysulfonyl group, a cyano group reduced to an amino group, a nitro group reduced to an amino group, a hydroxy group alkylated to a methoxy group, a hydroxy group thiomethylated to an arylthiomethyl or a heteroarylthiomethyl group (see, for example, Tet. Lett., 585, 1972), a carbonyl group converted to a thiocarbonyl group (eg. using Lawsson's reagent) or a bromo group converted to an alkylthio group. It is also possible to convert one Rc group into another Rc group as a final step in the preparation of a compound of the formula (I), for example, acylation of a group of formula (TC5) wherein Rc is hydrogen.

(b)(i) Reaction (b)(i) is performed under Mitsunobu conditions, for example, in the presence of tri-n-butylphosphine and diethyl azodicarboxylate (DEAD) in an organic solvent such as THF, and in the temperature range 0° C.–60° C., but preferably at ambient temperature. Details of Mitsunobu reactions are contained in Tet. Letts., 31, 699, (1990); The Mitsunobu Reaction, D. L. Hughes, Organic Reactions, 1992, Vol. 42, 335–656 and Progress in the Mitsunobu Reaction, D. L. Hughes, Organic Preparations and Procedures International, 1996, Vol. 28, 127–164.

Particularly suitable values for Pg are the following, or suitable derivatives thereof; Pg such as to give a carbamate (for example Pg as t-BOC or 2,2,2-trichloroethyloxycarbonyl), Pg as (1–4C)alkanoyl (for example acxetyl or chloroacetyl), phosphoramidate, allyloxy, benzyloxy (and methyl/nitro derivatives thereof) or sulfonyl (such as, for example, tosylate, mesylate, 4-nitrophenylsulfonyl, 4-methoxy-2,3,6-trimethyl-phenylsulfonyl). See the accompanying Examples for particular values of Pg.

Pg may be removed by techniques available to the skilled chemist (see also techniques described elsewhere herein). For example, tosylate and mesylate may be removed using standard deprotection conditions, or Na/Li amalgam or Mg/MeOH under standard conditions; 4-nitrophenylsulfonyl may be removed using base and phenylthio or thioacetic acid; 4-methoxy-2,3,6-trimethyl-phenylsulfonyl may be removed using TFA deprotection under standard conditions.

Compounds of the formula (II) wherein Y is hydroxy may be obtained as described in the references cited herein (particularly in the section proceeding the discussion of protecting groups), for example, by reacting a compound of the formula (VI) with a compound of formula (VII):

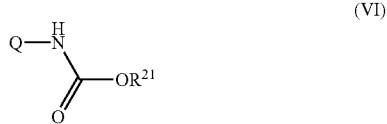

(VI)

-continued

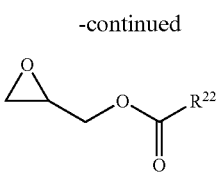
(VII)

wherein $R^{21}$ is (1–6C)alkyl or benzyl and $R^{22}$ is (1–4C)alkyl or —S(O)$_a$(1–4C)alkyl where n is 0, 1 or 2. Preferably $R^{22}$ is (1–4C)alkyl.

In particular, compounds of the formula (II), (VI) and (VII) may be prepared by the skilled man, for example as described in International Patent Application Publication Nos. WO95/07271, WO97/27188, WO 97/30995, WO 98/01446 and WO 98/01446, the contents of which are hereby incorporated by reference, and by analogous processes.

If not commercially available, compounds of the formula (III) may be prepared by procedures which are selected from standard chemical techniques, techniques which are analogous to the synthesis of known, structurally similar compounds, or techniques which are analogous to the procedures described in the Examples. For example, standard chemical techniques are as described in Houben Weyl, Methoden der Organische Chemie, E8a, Pt.I (1993), 45–225, B. J. Wakefield. Many amino-HET compounds are commercially available and may be converted into HN(Pg)—HET by standard techniques.

(b)(ii) Reactions (b)(ii) are performed conveniently in the presence of a suitable base such as, for example, an alkali or alkaline earth metal carbonate, alkoxide or hydroxide, for example sodium carbonate or potassium carbonate, or, for example, an organic amine base such as, for example, pyridine, 2,6-lutidine, collidine, 4-dimethylaminopyridine, triethylamine, morpholine or diazabicyclo-[5.4.0]undec-7-ene, the reaction is also preferably carried out in a suitable inert solvent or diluent, for example methylene chloride, acetonitrile, tetrahydrofuran, 1,2-dimethoxyethane, N,N-dimethylformamide, N,N-dimethylacetamide, N-methylpyrrolidin-2-one or dimethylsulfoxide at and at a temperature in the range 25–60° C.

When Y is chloro, the compound of the formula (II) may be formed by reacting a compound of the formula (II) wherein Y is hydroxy (hydroxy compound) with a chlorinating agent. For example, by reacting the hydroxy compound with thionyl chloride, in a temperature range of ambient temperature to reflux, optionally in a chlorinated solvent such as dichloromethane or by reacting the hydroxy compound with carbon tetrachloride/triphenyl phosphine in dichloromethane, in a temperature range of 0° C. to ambient temperature. A compound of the formula (II) wherein Y is chloro or iodo may also be prepared from a compound of the formula (II) wherein Y is mesylate or tosylate, by reacting the latter compound with lithium chloride or lithium iodide and crown ether, in a suitable organic solvent such as THF, in a temperature range of ambient temperature to reflux When Y is (1–4C)alkanesulfonyloxy or tosylate the compound (II) may be prepared by reacting the hydroxy compound with (1–4C)alkanesulfonyl chloride or tosyl chloride in the presence of a mild base such as triethylamine or pyridine.

When Y is a phosphoryl ester (such as $PhO_2$—P(O)—O—) or $Ph_2$—P(O)O— the compound (II) may be prepared from the hydroxy compound under standard conditions.

(c) Reaction (c) is performed under conditions analogous to those described in the following references which disclose how suitable and analogous starting materials may be obtained.

Reaction (c) is especially suitable for compounds in which HET is an electron deficient heteroaryl (such as, for example, thiadiazole or triazine).

Compounds of the formula Q—Z wherein Z is an isocyanate may be prepared by the skilled chemist, for example by analogous processes to those described in Walter A. Gregory et al in J. Med. Chem. 1990, 33, 2569–2578 and Chung-Ho Park et al in J. Med. Chem. 1992, 35, 1156–1165. Compounds of the formula Q—Z wherein Z is a urethane may be prepared by the skilled chemist, for example by analogous processes to those described in International Patent Application Publication Nos. WO 97/30995 and WO 97/37980.

A similar reaction to reaction (c) may be performed in which Q—Z wherein Z is a amine group is reacted with the epoxide (optionally in the presence of an organic base), and the product is reacted with, for example, phosgene to form the oxazolidinone ring. Such reactions and the preparation of starting materials in within the skill of the ordinary chemist with reference to the above-cited documents disclosing analogous reactions and preparations.

Epoxides of the formula (V) may be prepared from the corresponding compound of formula (VIII):

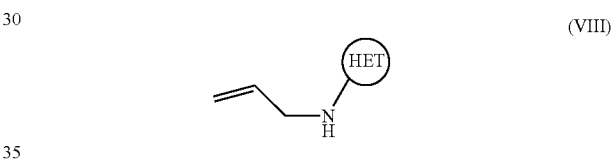
(VIII)

Certain such epoxide and alkene intermediates are novel and are provided as a further feature of the invention. For example, when T or $T^1$ is isoxazol-3-yl, 3-(2,3-oxiranepropylamino)isoxazole may be prepared from 3-allylaminoisoxazole. Asymmetric epoxidation may be used to give the desired optical isomer.

(d) The skilled man will appreciate that for the reaction of a compound of formula (II) wherein Y is an amino group with a compound of the formula (I HA), Lg—HET, certain, reactive heteroarlys HET react satisfactorily, such as triazines and pyridazine. A suitable value for Lg is chloro. The reaction is performed under standard conditions in an inert solvent and in the presence of a suitable base (such as triethylamine).

Compounds of the formula (II) wherein Y is amino may be obtained as described in the references cited herein (particularly in the section proceeding the discussion of protecting groups), for example from the corresponding compounds in which Y is hydroxy (via the azide).

The removal of any protecting groups, the formation of a pharmaceutically-acceptable salt and/or the formation of an in vivo hydrolysable ester are within the skill of an ordinary organic chemist using standard techniques. Furthermore, details on the these steps, for example the preparation of in-vivo hydrolysable ester prodrugs has been provided in the section above on such esters, and in certain of the following non-limiting Examples.

When an optically active form of a compound of the formula (I) is required, it may be obtained by carrying out one of the above procedures using an optically active starting material (formed, for example, by asymmetric induction of a suitable reaction step), or by resolution of a racemic form of the compound or intermediate using a standard procedure, or by chromatographic separation of diastereoisomers (when produced). Enzymatic techniques may also be useful for the preparation of optically active compounds and/or intermediates.

Similarly, when a pure regioisomer of a compound of the formula (I) is required, it may be obtained by carrying out one of the above procedures using a pure regioisomer as a starting material, or by resolution of a mixture of the regioisomers or intermediates using a standard procedure.

According to a further feature of the invention there is provided a compound of the formula (I), or a pharmaceutically-acceptable salt, or in-vivo hydrolysable ester thereof for use in a method of treatment of the human or animal body by therapy.

According to a further feature of the present invention there is provided a method for producing an antibacterial effect in a warm blooded animal, such as man, in need of such treatment, which comprises administering to said animal an effective amount of a compound of the present invention, or a pharmaceutically-acceptable salt, or in-vivo hydrolysable ester thereof.

The invention also provides a compound of the formula (I), or a pharmaceutically-acceptable salt, or in-vivo hydrolysable ester thereof, for use as a medicament; and the use of a compound of the formula (I) of the present invention, or a pharmaceutically-acceptable salt, or in-vivo hydrolysable ester thereof, in the manufacture of a medicament for use in the production of an antibacterial effect in a warm blooded animal, such as man.

In order to use a compound of the formula (I), an in-vivo hydrolysable ester or a pharmaceutically-acceptable salt thereof, including a pharmaceutically-acceptable salt of an in-vivo hydrolysable ester, (hereinafter in this section relating to pharmaceutical composition "a compound of this invention") for the therapeutic (including prophylactic) treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the formula (I), an in-vivo hydrolysable ester or a pharmaceutically-acceptable salt thereof, including a pharmaceutically-acceptable salt of an in-vivo hydrolysable ester, and a pharmaceutically-acceptable diluent or carrier.

The pharmaceutical compositions of this invention may be administered in standard manner for the disease condition that it is desired to treat, for example by oral, rectal or parenteral administration. For these purposes the compounds of this invention may be formulated by means known in the art into the form of, for example, tablets, capsules, aqueous or oily solutions or suspensions, (lipid) emulsions, dispersible powders, suppositories, ointments, creams, aerosols (or sprays), drops and sterile injectable aqueous or oily solutions or suspensions.

In addition to the compounds of the present invention the pharmaceutical composition of this invention may also contain or be co-administered (simultaneously, sequentially or separately) with one or more known drugs selected from other clinically useful antibacterial agents (for example, β-lactams or aminoglycosides) and/or other anti-infective agents (for example, an antifungal triazole or amphotericin). These may include carbapenems, for example meropenem or imipenem, to broaden the therapeutic effectiveness. Compounds of this invention may also contain or be co-administered with bactericidal/permeability-increasing protein (BPI) products or efflux pump inhibitors to improve activity against gram negative bacteria and bacteria resistant to antimicrobial agents.

A suitable pharmaceutical composition of this invention is one suitable for oral administration in unit dosage form, for example a tablet or capsule which contains between 1 mg and 1 g of a compound of this invention, preferably between 100 mg and 1 g of a compound. Especially preferred is a tablet or capsule which contains between 50 mg and 800 mg of a compound of this invention, particularly in the range 100 mg to 500 mg.

In another aspect a pharmaceutical composition of the invention is one suitable for intravenous, subcutaneous or intramuscular injection, for example an injection which contains between 0.1% w/v and 50% w/v (between 1 mg/ml and 500 mg/ml) of a compound of this invention.

Each patient may receive, for example, a daily intravenous, subcutaneous or intramuscular dose of 0.5 mgkg$^{-1}$ to 20 mgkg$^{-1}$ of a compound of this invention, the composition being administered 1 to 4 times per day. In another embodiment a daily dose of 5 mgkg$^{-1}$ to 20 mgkg$^{-1}$ of a compound of this invention is administered. The intravenous, subcutaneous and intramuscular dose may be given by means of a bolus injection. Alternatively the intravenous dose may be given by continuous infusion over a period of time. Alternatively each patient may receive a daily oral dose which may be approximately equivalent to the daily parenteral dose, the composition being administered 1 to 4 times per day.

A pharmaceutical composition to be dosed intravenously may contain advantageously (for example to enhance stability) a suitable bactericide, antioxidant or reducing agent, or a suitable sequestering agent.

In the above other, pharmaceutical composition, process, method, use and medicament manufacture features, the alternative and preferred embodiments of the compounds of the invention described herein also apply.

Antibacterial Activity

The pharmaceutically-acceptable compounds of the present invention are useful antibacterial agents having a good spectrum of activity in vitro against standard Gram-positive organisms, which are used to screen for activity against pathogenic bacteria. Notably, the pharmaceutically-acceptable compounds of the present invention show activity against enterococci, pneumococci and methicillin resistant strains of *S. aureus* and coagulase negative staphylococci. The antibacterial spectrum and potency of a particular compound may be determined in a standard test system.

The (antibacterial) properties of the compounds of the invention may also be demonstrated and assessed in-vivo in conventional tests, for example by oral and/or intravenous dosing of a compound to a warm-blooded mammal using standard techniques.

The following results were obtained on a standard in-vitro test system. The activity is described in terms of the minimum inhibitory concentration (MIC) detemined by the agar-dilution technique with an inoculum size of $10^4$ CFU/spot. Typically, compounds are active in the range 0.01 to 256 µg/ml.

Staphylococci were tested on agar, using an inoculum of $10^4$ CFU/spot and an incubation temperature of 37° C. for 24 hours—standard test conditions for the expression of methicillin resistance.

Streptococci and enterococci were tested on agar supplemented with 5% defibrinated horse blood, an inoculum of $10^4$ CFU/spot and an incubation temperature of 37° C. in an atmosphere of 5% carbon dioxide for 48 hours—blood is required for the growth of some of the test organisms.

For example, the following results were obtained for the compound of Example 2:

| Organism | MIC (µg/ml) |
| --- | --- |
| Staphylococcus aureus: | |
| Oxford | 0.5 |
| Novb. Res | 1 |
| MRQR | 1 |
| Coagulase Negative Staphylococci | |
| MS | 0.5 |
| MR | 1 |
| Streptococcus pyogenes | |
| C203 | 1 |
| Enterococcus faecalis | 2 |
| Bacillus subtilis | 0.5 |

Novb. Res = Novobiocin resistant
MRQR = methicillin resistant quinolone resistant
MR = methicillin resistant
MS = methicillin sensitive Certain intermediates and/or Reference Examples described hereinafter (especially those in which the —NH— link to HET is protected by a BOC group) may also possess useful activity, and are provided as a further feature of the invention.

The invention is now illustrated but not limited by the following Examples in which unless otherwise stated:—

(i) evaporations were carried out by rotary evaporation in vacuo and work-up procedures were carried out after removal of residual solids by filtration;

(ii) operations were carried out at ambient temperature, that is typically in the range 18–26° C. and in air unless otherwise stated, or unless the skilled person would otherwise work under an inert atmosphere;

(iii) column chromatography (by the flash procedure) was used to purify compounds and was performed on Merck Kieselgel silica (Art. 9385) unless otherwise stated;

(iv) yields are given for illustration only and are not necessarily the maximum attainable;

(v) the structure of the end-products of the formula (I) were generally confirmed by NMR and mass spectral techniques [proton magnetic resonance spectra were generally determined in DMSO-D6 unless otherwise stated using a Varian Gemini 2000 spectrometer operating at a field strength of 300 MHz, or a Bruker AM250 spectrometer operating at a field strength of 250 MHz; chemical shifts are reported in parts per million downfield from tetramethysilane as an internal standard (δ scale) and peak multiplicities are shown thus: s, singlet; d, doublet; AB or dd, doublet of doublets; t, triplet, m, multiplet; fast-atom bombardment (FAB) mass spectral data were generally obtained using a Platform spectrometer (supplied by Micromass) run in electrospray and, where appropriate, either positive ion data or negative ion data were collected];

(vi) intermediates were not generally fully characterised and purity was in general assessed by thin layer chromatographic, infra-red (IR), mass spectral (MS) or NMR analysis; and (vii) in which the following abbreviations may be used:—
® is a Trademark; DMF is N,N-dimethylformamide; DMA is N,N-dimethylacetamide; TLC is thin layer chromatography; HPLC is high pressure liquid chromatography; MPLC is medium pressure liquid chromatography; DMSO is dimethylsulfoxide; $CDCl_3$ is deuterated chloroform; MS is mass spectroscopy; ESP is electrospray; THF is tetrahydrofuran; TFA is trifluoroacetic acid; NMP is N-methylpyrrolidone; HOBT is 1-hydroxy-benzotriazole; EtOAc is ethyl acetate; MeOH is methanol; phosphoryl is $(HO)_2$—P(O)—O—; phosphiryl is $(HO)_2$—P—O—; EDC is 1-(3-dimethylaminopropyl)-3-ethylcarbodiimide (hydrochloride); PTSA is para-toluenesulfonic acid.

EXAMPLE 1

5(S)-Isoxazol-3-ylaminomethyl-3-(3-fluoro-4-(3,6-dihydro-(2H)=pyran-4-yl)phenyl)oxazolidin-2-one

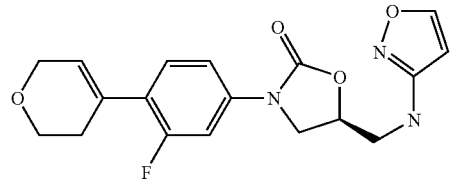

To a stirred solution of 3-(2,2,2-trichloroethyloxycarbonylamino)isoxazole (631 mg, 2.43 mmol) in dry N,N-dimethylformamide (10 ml), under a nitrogen atmosphere was added a suspension of sodium hydride (107 mg of a 60% dispersion in oil, 2.67 mmol) in hexane followed by 5(R)-methanesulfonyloxymethyl-3-(3-fluoro-4-(3,6-dihydro-(2H)-pyran-4-yl)phenyl)oxazolidin-2-one (see WO 97/09328; 226 mg, 0.61 mmol) in dry DMF (3 ml). Over a period of 24 hours further batches of sodium hydride totalling (428 mg of a 60% dispersion in oil, 10.7 mmol), were added and the reaction mixture heated to 50–60° C. for 24 h, after which time TLC indicated the formation of the desired product (Rf 0.34, 50% ethyl acetate/hexane). The majority of the N,N-dimethylformamide was evaporated under hi-vacuum and the product isolated by MPLC (50% THF/Hexane) and then triturated with ether to yield the title compound as a white amorphous solid (63.4 mg, 29%).

NMR: 2.42 (m, 2H), 3.45 (m, 2H), 3.81 (m, 3H), 4.15 (t, 1H), 4.21 (d, 2H), 4.90 (m, 1H), 6.01 (d, 1H), 6.09 (m, 1H), 6.53 (t, 1H), 7.31 (dd, 1H), 7.40 (t, 1H), 7.48 (dd, 1H), 8.39 (d, 1H); m/z: ES$^+$ (M+H)=360.

The 3-(2,2,2-trichloroethyloxycarbonylamino)isoxazole (Reference Example 1) starting material was prepared as follows:

To a stirred solution of 3-aminoisoxaxole (2.0 g, 23.8 mmol) and sodium hydrogencarbonate (5.0 g, 59.5 mmol) in acetone/water (45 ml, 2:1), at 0–5° C. was added dropwise 2,2,2-trichloroethyl chloroformate (5.55 g, 26.2 mmol, 3.6 ml) in acetone (15 ml). The reaction mixture was allowed to warm to room temperature and was stirred for 4 hours. It was then cooled back to 0–5° C. and a further portion of sodium hydrogencarbonate (5.0 g, 59.5 mmol), and 2,2,2-trichloroethyl chloroformate (5.55 g, 26.2 mmol, 3.6 ml) in acetone (10 ml) was added. The solution was allowed to warm to room temperature and was stirred for a further 3 hours. Thin layer chromatography after this time showed complete reaction (Rf=0.79, 5% MeOH/CH$_2$Cl$_2$). Water was added and the mixture extracted with ethyl acetate (4×), and the extracts were combined, washed with brine, dried over sodium sulfate, and concentrated by rotary evaporation to give a yellow oil (11.2 g). This was purified by MPLC (3% MeOH/CH$_2$Cl$_2$) and recrystallized with cyclohexane, to give the title compound as white fluffy crystals (4.91 g, 80%). NMR: 4.95 (s, 2H), 6.74 (d, 1H), 8.78 (d, 1H), 11.19 (s, 1H); m/z: ES$^+$ (M+H)=259.

EXAMPLE 2

5(S)-Isoxazol-3-ylaminomethyl-3-(3-fluoro-4-morpholinophenyl)-oxazolidin-2-one

To a stirred solution of 5(R)-[N-isoxazol-3-yl-N-(2,2,2-trichloroethyloxycarbonyl) aminomethyl]-3-(3-fluoro-4-morpholinophenyl)oxazolidin-2-one (140 mg, 0.26 mmol) in glacial acetic acid (6 ml) at room temperature under a nitrogen atmosphere, was added zinc dust (acid washed, 68 mg, 1.04 mmol). After 4 hours a further portion of zinc (68 mg, 1.04 mmol) was added and stirring was continued for a further 1.5 hours until reaction was complete. The reaction mixture was filtered and concentrated by rotary evaporation to give colourless crystals (347 mg) which were extracted with dichloromethane (2×), with sonication. The resulting suspension was filtered and chromatographed by MPLC (3% MeOH/CH$_2$Cl$_2$), and further MPLC (4080% ethyl acetate/hexane gradient). The title compound was isolated as an amorphous solid by trituration of the concentrated fractions with ether (23.4 mg, 25%).

NMR: 2.94 (t, 4H), 3.41 (t, 2H), 3.71 (m, 4H), 3.77 (t, 1H), 4.10 (t, 1H), 5.98 (s, 1H), 6.50 (t, 1H), 7.04 (t, 1 μl), 7.17 (d, 1H), 7.48 (dd, 1H), 8.37 (s, 1H). MS: ES+ (M+H) =363.

The 5(R)-[N-Isoxazol-3-yl-N-(2,2,2-trichloroethyloxycarbonyl)aminomethyl]-3-[(3-fluoro-4-morpholinophenyl) oxazolidin-2-one (Reference Example 2) starting material was prepared as follows:

To a stirred solution of 3-(2,2,2-trichloroethyloxycarbonylamino)isoxazole (260 mg, 1.0 mmol), 5(R)-hydroxymethyl-3-(3-fluoro-4-morpholinophenyl)oxazolidin-2-one (see WO 95/07271; 293 mg, 1 mmol) and tributylphosphine (303 mg, 1.5 mmol) in dry tetrahydrofuran (10 ml) at 0° C. under a nitrogen atmosphere, was added 1,1-(azodicarbonyl) dipiperidine (378.5 mg, 1.5 mmol) in dry tetrahydrofuran (3 ml). The reaction allowed to warm to room temperature and was stirred for 4 days by which time a white suspension had formed. The reaction mixture was filtered and the residue washed with tetrahydrofuran. The filtrate was concentrated by rotary evaporation to give a yellow oil (1.2 g) which was purified by MPLC (30% ethyl acetate/hexane, ICN Alumina N 32–63) and further MPLC (100% CH$_2$Cl$_2$, ICN Alumina N 32–63). Concentration of the fractions by rotary evaporation gave the title compound as a crisp white foam (296 mg, 55%).

NMR: 2.97 (t, 4H), 3.73 (t, 4H), 3.88 (m, 1H), 4.17 (m, 2H), 4.38 (m, 1H), 5.04 (m, 3H), 6.90 (s, 1H), 7.06 (t, 1H), 7.18 (dd, 1H), 7.46 (dd, 1H), 8.91 (d, 1H); m/z ES$^+$ (M+H)=537.

EXAMPLE 3

5(S)-Isoxazol-3-ylaminomethyl-3-(3-fluoro-4-(1-formyl-1,2,5,6 tetrahydropyrid-4-yl)phenyl)oxazolidin-2-one

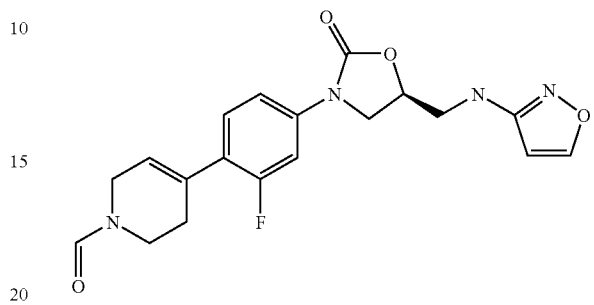

To a stirred solution of 5(R)-[N-isoxazol-3-yl-N-(2,2,2-trichloroethyloxycarbonyl)-aminomethyl]-3-[3-fluoro-4-(1-formyl-1,2,5,6-tetrahydropyrid-4-yl)phenyl] oxazolidin-2-one (110 mg, 0.2 mM) in acetic acid (3 ml) was added zinc dust (130 mg, 2.0 mM). The mixture was held in an ultrasonic bath for 10 min. and then stirred vigorously for 48 hours under a nitrogen atmosphere at ambient temperature. The mixture was filtered through celite and the filtrate was evaporated. The residue was taken into ~5% MeOH/CH$_2$Cl$_2$ (5 ml) with filtration of inorganic material and the title compound was isolated by MPLC (4% MEOH/CH$_2$Cl$_2$). It was obtained as a brittle glass on evaporation under high vacuum (22 mg, 28%).

NMR: 2.41(s, 2H), 3.45(m, 2H), 3.60(m, 2H), 3.84(t, 1H), 4.08(m, 2H), 4.19(t, 1H), 4.91(m, 1H), 6.00(m, 2H), 6.53(m, 1H), 7.36(m, 2H), 7.54(d, 2H), 8.11 & 8.19(2s, 1H), 8.37(s, 1H); m/z ES$^+$ (M+H)=387.

The 5(R)-[N-Isoxazol-3-yl-N-(2,2,2-trichloroethyloxyonyl)aminomethyl]-3-[3-fluoro-4-(1-formynl-1,2,5,6-tetrahydropyrid-4-yl)phenyl]oxazolidin-2-one (Reference Example 5) starting material was obtained as follows:

5(R)-[N-Isoxazol-3-yl-N-(2,2,2-trichloroethyloxycarbonyl)aminomethyl]-3-[3-fluoro-4-(1-benzyl-1,2,5,6-tetrahydropyrid-4-yl)phenyl]oxazolidin-2-one (Reference Example 3)

To a stirred solution of 3-(2,2,2-trichloroethyloxycarbonylamino)isoxazole (1.30 g, 5.0 mmol), 5(R)-hydroxymethyl-3-(3-fluoro-4-(1-benzyl-1,2,5,6-tetrahydropyrid-4-yl) phenyl)oxazolidin-2-one (WO 97/30995; 1.91 g, 5.0 mmol) and tributylphosphine (1.52 g, 7.5 mmol) in dry tetrahydrofuran (50 ml) under a nitrogen atmosphere at 0° C., was added 1,1'-(azodicarbonyl)dipiperidine (1.89 g, 7.5 mmol) in dry tetrahydrofuran (15 ml). The solution was stirred at 0° C. for 30 minutes before being allowed to come to room temperature and it was then stirred for 2 days. The mixture was filtered, concentrated by rotary evaporation and chromatographed by MPLC (30% ethyl acetate/hexane, ICN Alumina N 32–63), and triturated with ether to give the title compound as a white amorphous solid (1.62 g, 52%).

NMR: 2.41 (m, 2H), 2.60 (t, 2H), 3.15 (m, 2H), 3.90 (dd, 1H), 4.18 (m, 2H), 4.37 (dd, 1H), 5.04 (dd, 3H), 5.95 (broad s, 1H), 6.88 (s, 1H), 7.32 (m, 3H), 8.89 (s, 1H); m/z ES$^+$ (M+H)=623.

5(R)-[N-Isoxazol-3-yl-N-(2,2,2-trichloroethyloxycarbonyl)aminomethyl]-3-[3-fluoro-4-(1,2,5,6-tetrahydropyrid-4-yl)phehyl]oxazolidin-2-one (Reference Example 4)

To an ice-cooled stirred solution of 5(R)-[N-isoxazol-3-yl-N-(2,2,2-trichloroethyloxycarbonyl)aminomethyl]-3-[3-fluoro-4-(1-benzyl-1,2,5,6-tetrahydropyrid-4-yl)phenyl]oxazolidin-2-one (720 mg, 1.15 mmol) and N,N-diisopropylethylamine (44.8 mg, 0.34 mmol, 60 µl) in dichloromethane (40 ml) under a nitrogen atmosphere was added dropwise 1-chloroethyl chloroformate (214 mg, 1.5 mmol, 162 µl). The reaction mixture was allowed to warm to room temperature and after 30 minutes the reaction was complete. It was chromatographed by MPLC (40% ethyl acetate/hexane) to yield a clear oil (737 mg) which was dissolved in methanol and stirred at 60° C. for 20 minutes, before the solvent was removed by rotary evaporation to give the title compound as an amorphous solid (538 mg, 94%).

NMR: 2.71 (m, 2H), 3.35 (m, 2H), 3.80 (m, 2H), 4.00 (m, 1H), 4.27 (m, 2H), 4.45 (dd, 1H), 5.13 (m, 3H), 6.10 (m, 1H), 6.96 (s, 1H), 7.38–7.60 (m, 3H), 9.00 (s, 1H), 9.21 (broad s, 2H); m/z ES$^+$ (M+H)=533.

5(R)-N-isoxazol-3-yl-N-(2,2,2-trichloroethyloxycarbonyl)aminomethyl]-3-[3-fluoro-4-(1-formyl-1,2,5,6-tetrahydropyrid-4-yl)phenyl]oxazolidin-2-one (Reference Example 5)

To a suspension of 5(R)-[N-isoxazol-3-yl-N-(2,2,2-trichloroethyloxycarbonyl)aminomethyl]-3-[3-fluoro-4-(1,2,5,6-tetrahydropyrid-4-yl)phenyl]oxazolidin-2-one (100 mg, 0.175 mmol) in ethyl formate (5 ml), with stirring was added, triethylamine (20 mg, 271 µl, 0.2 mmol), and the mixture was heated to reflux overnight. Ethyl formate was added and the mixture washed with 2M hydrochloric acid and saturated brine, dried over sodium sulfate and concentrated by rotary evaporation to give the crude title compound as a yellow gum (115 mg, 117%). M/z ES$^+$ (M+H)=561.

EXAMPLE 4

5(S)-Isoxazol-3-ylaminomethyl-3-[3-fluoro-4-(1-acetoxyacetyl-1,2,5,6-tetrahydropyrid-4-yl)phenyl]oxazolidin-2-one To a stirred solution of 5(R)-[N-Isoxazol- 3-yl-N-(2,2,2-trichloroethyloxycarbonyl)aminomethyl]-3-[3-fluoro-4-(1-acetoxyacetyl-1,2,5,6-tetrahydropyrid-4-yl)phenyl]oxazolidin-2-one (1.14 g, 1.8 mM) in acetic acid (15 ml) was added zinc dust (1.17 g, 18 mM). The mixture was stood in an ultrasonic bath for 10 minutes then water (2 ml) was added and the mixture was stirred vigorously for 24 hrs under nitrogen at ambient temperature. The mixture was filtered through celite and the filtrate was evaporated. The title compound was isolated by MPLC (4% MEOH/CH$_2$Cl$_2$). It was obtained as a crystalline solid on trituration with ether (473 mg, 57%).

NMR: 2.10 (s, 3H), 2.42 (s, 2H), 3.45 (t, 2H), 3.58 (t, 1H), 3.67 (t, 1H), 3.85 (d of d, 1H), 4.09 (s, 2H), 4.18 (t, 1H), 4.86 (m, 3H), 6.00 (d, 2H), 6.52 (t, 1H), 7.29 (d of d, 1H), 7.38 (t, 1H), 7.50 (d, 1H), 8.38 (s, 1H); m/z ES$^+$ (M+H) 459.

The 5(R)-[N-Isoxazol-3-yl-N-(2,2,2-trichloroethyloxycarbonyl)aminomethyl]-3-[3-fluoro-4-(1-acetoxyacetyl-1,2,5,6-tetrahydropyrid-4-yl)phenyl]oxazolidin-2-one (Reference Example 6) starting material was prepared as follows:

To a ice-cooled, stirred solution of 5(R)-[N-Isoxazol-3-yl-N-(2,2,2-trichloroethyloxycarbonyl)aminomethyl]-3-[3-fluoro-4-(1,2,5,6-tetrahydropyrid-4-yl)phenyl]oxazolidin-2-one (102 mg, 0.18 mmol) and sodium bicarbonate (75 mg, 0.89 mmol) in acetone (10 ml)/water (5 ml), was added dropwise acetoxyacetyl chloride (49 mg, 0.36 mmol, 38.5%1). After 15 minutes, complete reaction had occurred by TLC (10% MeOH/CH$_2$Cl$_2$, UV visualisation, Rf=0.75). Water was then added and the aqueous phase extracted with ethyl acetate, and the resulting organic phase washed with water, 2M hydrochloric acid and saturated brine, dried over sodium sulfate and concentrated by rotary evaporation to give the title compound as a crude yellow gum (105 mg, 93%).

NMR: 2.10 (broad s, 3H), 2.42 (m, 2H), 3.62 (dt, 2H), 3.94 (m, 1H), 4.19 (m, 4H), 4.40 (dd, 1H), 4.84 (d, 2H), 5.05 (m, 3H), 6.01 (broad s, 1H), 6.91 (s, 1H), 7.31 (d, 1H), 7.43 (m, 2H), 8.91 (s, 1H); m/z: ES$^+$ (M+H)=633.

EXAMPLE 5

5(S)-Isoxazol-3-ylaminomethyl-3-[3-fluoro-4-(1-hydroxyacetyl-1,2,5,6-tetrahydropyrid-4-yl)plhenyl-loxazolidin-2-one A solution of 5(S)-Isoxazol-3-ylaminomethyl-3-[3-fluoro 4(1-acetoxyacetyl-1,2,5,6-tetrahydropyrid-4-yl)phenyl]oxazolidin-2-one (400 mg, 0.87 mM) in saturated methanolic ammonia (10 ml) was stirred for 18 hrs. at ambient temperature. The title compound crystallised on evaporating to a small volume and was triturated with ether (334 mg, 92%).

NMR: 2.45 (s, 2H), 3.46 (t, 2H), 3.69 (t, 1H), 3.84 (d of d, 1H), 4.12 (m, 5H), 4.55 (m, 1H), 4.90 (6 line, 1H), 6.00 (m, 2H), 6.54 (t, 1H), 7.31 (d of d, 1H), 7.37 (t, 1H), 7.51 (d, 1H), 8.38 (s, 1H); m/z ES$^+$ (M+H) 417.

EXAMPLE 6

5(S)-Isoxazol-3-ylaminomethyl-3-[3-fluoro-4-(1-(2 (S),3-dihydroxpropanoyl)-1,2,5,6-tetrahydropyrid-4-yl)phenylloxazolidin-2-one To a stirred solution of 5(R)-[N-isoxazol-3-yl-N-(2,2,2-trichloroethyloxycarbonyl)aminomethyl]-3-{3-fluoro-4-[N-(2,2-dimethyl-1,3-dioxolan-4(S)-ylcarbonyl)-1,2,5,6- tetrahydropyrid yl]phenyl}oxazolidin-2-one (200 mg, 0.3 mM) in acetic acid (3 ml) was added zinc dust (195 mg, 3.0 mM). The mixture was stood in an ultrasonic bath for 10 min. then stirred vigorously for 24 hours under a nitrogen atmosphere at ambient temperature. Water (0.5 ml) was added and stirring was continued for a further 24 hours. The reaction mixture was filtered through celite and evaporated. The residue was dissolved in tetrahydrofuran (ISml)/1.0M aq. HCl (10 ml) and was stirred at ambient temperature for 3 days. It was evaporated to dryness and the residue was chromatographed by MPLC (8% MeOH I CH$_2$Cl$_2$, gradient to 25%). The title compound was obtained as a white powder on trituration with ether/ethanol (68 mg, 50%).

NMR: δ 2.42(s, 2H, partially obscured), 3.43(m, 2H), 3.57(m, 1H), 3.79(m, 3H), 4.16(m, 2H), 4.27(m, 1H), 4.38 (m, 1H), 4.72(m, 1H), 4.91(m, 1H), 5.00(m, 1H), 6.00(m, 2H), 6.57(t, 1H), 7.30(d of d, 1H), 7.39(t, 1H), 7.50(d of d, 1H), 8.40(s, 1H); m/z ES+ (M+H)=447.

The 5(R)-N-isoxazol-3-yl-N-(2,2,2-trichloroethyloxycarbonyl)aminomethyl]-3-{3-fluoro-4-[N-(2,2-dimethyl-1,3-dioxolan-4(S)-ylcarbonyl)-1,2,5,6-tetrahydropyrid-4-yl]phenyl}oxazolidin-2-one Reference Example 7) starting material was prepared as follows:

To a stirred solution of 5(R)-[N-isoxazol-3-yl-N-(2,2,2-trichloroethyloxycarbonyl)-aminomethyl]- 3-[3-fluoro-4-(1,2,5,6-tetrahydropyrid yl)phenyl]oxazolidin-2-one (228 mg, 0.4 mM) in dry dichloromethane (5 ml) at 0–4° C., was added pyridine (158 mg, 2.0 mM) followed by dropwise addition of a solution of (S)-(+)-2,3,0-isopropylideneglycinoyl chloride (EP 0 413 401 A2; 200 mg, 1.2 mM) in dichloromethane (1 ml). The solution was stirred at 0–4° C. for 10 min. and then allowed to warm to ambient temperature. The reaction mixture was washed with water and brine, dried over sodium sulfate and evaporated to a gum. The title compound was isolated by MPLC (60% ethyl acetate/isohexane) and was obtained as a crisp foam on evaporation (158 mg, 60%).

NMR: 1.36(m, 6H), 2.42(s, 2H), 3.79(m, 2H), 3.92(m, 1H), 4.15(m, 6H), 4.40(d of d, 1H), 4.90(5 line, 1H), 5.05(4 line, 3H), 6.03(s, 1H), 6.90(s, 1H), 7.25–7.50(m, 3H), 8.91 (s, 1H); m/z: ES$^+$ (M+H)=661.

EXAMPLE 7

5(S)-Isoxazol-3-ylaminomethyl-3-(4-imidazol-1-yl-3-fluorophenyl)-oxazolidin-2-one 5(R)—(N-(2,2,2-Trichloroethyloxycarbonyl)-isoxazol-3-ylaminomethyl)-3-(4-imidazol-1-yl-3-fluorophenyl)oxazolidin-2-one (crude, 1.7 g, ~2.5 mM), was stirred in a mixture of acetic acid (40 ml) and water (18 ml) under nitrogen at ambient temperature. Zinc dust (824 mg, 12.5 mM) was added, the mixture stirred 20 minutes, a further portion (200 mg) of zinc added, and stirring continued for 1 hour. The mixture was filtered through celite, and the filter pad washed well with a mixture of acetic acid and water (5:1). The filtrates were evaporated, and the residue partitioned between hydrochloric acid (0.5M, 200 ml) and dichloromethane (150 ml). The aqueous phase was washed with dichloromethane (100 ml), then made basic with the minimum quantity of concentrated ammonia solution, re-extracted with dichloromethane (2×150 ml), dried (magnesium sulfate), and evaporated. Recrystallisation from isopropanol (40 ml) gave the desired product (470 mg).

NMR (DMSO-d$_6$) δ: 3.46 (t, 2H); 3.87 (dd, 1H); 4.21 (t, 1H); 4.92 (m, 1H); 6.01 (d, 1H); 6.53 (t, 1H); 7.12 (t, 1H); 7.46 (dd, 1H); 7.53 (d, 1H); 7.66 (t, 1H); 7.74 (dd, 1H); 7.98 (m, 1H); 8.39 (d, 1H). MS (ESP): 362 (MH$^+$) for $C_{16}H_{14}FN_5O_3$ The 5(R)-(N-(2,2,2-Trichloroethyloxycarbonyl)-isoxazol-3-ylaminoethyl)-3-(4-imidazol-1-yl-3-fluorophenyl)oxazolidin-2-one intermediate was prepared as follows:

3-(4-Imidazol-1-yl-3-fluorophenyl)-5(R)-hydroxymethyloxazolidin-2-one (693 mg, 2.5 mM, see WO 96-23788) and 3-(2,2,2-trichloroethyloxycarbonylamino)isoxazole (649 mg, 2.5 mM) were suspended by stirring in dry tetrahydrofuran (25 ml) under nitrogen in an ice-bath. Tributylphosphine (808 mg, 4 mM) was added followed by 1,1'-(azodicarbonyl)dipiperidine (945 mg, 3.75 nM) dissolved in tetrahydrofuran (10 ml) over 10 minutes. The mixture was then stirred 18 hours, allowing the temperature to rise to ambient, then filtered, and the filter cake washed with tetrahydrofuran. The combined filtrates were evaporated and the residue purified by chromatography on a 20 g silica Mega Bond Elut® column, eluting with a gradient increasing in polarity from 0 to 5% methanol in dichloromethane. Relevant fractions were combined, evaporated, and the residue triturated with diethyl ether to give the desired product (1.36 g), contaminated with tributylphosphine oxide.

NMR (DMSO-d$_6$) δ3.95 (dd, 1H); 4.16 (dd, 1H); 4.26 (t, 1H); 4.41 (dd, 1H); 4.99 (dd, 1H); 5.08 (dd overlapping m, 2H); 6.89 (d, 1H); 7.10 (t, 1H); 7.44 (dd, 1H); 7.52 (d, 1H); 7.66 (t, 1H); 7.71 (dd, 1H); 7.98 (m, 1H); 8.90 (d, 1H). MS (ESP): 518 (MH$^+$) for $C_{19}H_{15}Cl_3FN_5O_5$

EXAMPLE 8

5(S)-Isoxazol-3-ylaminomethyl-3-(4-(4-Hydroxymethylimidazol-1-yl)-3-fluorophenyl)oxazolidin-2-one 3-(4-(4-Hydroxymethylimidazol-1-yl)-3-fluorophenyl)-5(R)-(N-(t-butoxycarbonyl)isoxazol-3-ylaminomethyl)oxazolidin-2-one (360 mg, 0.76 mM) was dissolved in dichloromethane (10 ml) and treated with trifluoroacetic acid (10 ml). After stirring for 30 minutes solvent was evaporated, the residue repeatedly evaporated to dryness with dichloromethane (3×10 ml), and the resulting gum dissolved in water (10 ml). The solution was made basic with concentrated aqueous ammonia, and the resulting precipitate filtered, washed with water and dried to give title product (190 mg).

MS (ESP): 374 (MH$^+$) for $C_{17}H_{16}FN_5O_4$

NMR (DMSO-d$_6$) δ: 3.45 (t, 2H); 3.85 (dd, 1H); 4.19 (t, 1H); 4.39 (d, 2H); 4.88 (t, 1H); 4.95 (m, 1H); 5.99 (d, 1H); 6.53 (t, 1H); 7.31 (d, 1H); 7.43 (dd, 1H); 7.62 (t, 1H); 7.72 (dd, 1H); 7.90 (d, 1H); 8.36 (d, 1H).

The 3-(4-(4-Hydroxymethylimidazol-1-yl)-3-fluorophenyl)-5(R)-(N-(t-butoxycarbonyl)-isoxazol-3-ylaminomethyl)oxazolidin-2-one intermediate was prepared as follows:

3-(4-(4-t-Butyldimethylsilyloxymethylimidazol-1-yl)-3-fluorophenyl)-5(R)-hydroxy-methyloxazolidin-2-one (842 mg, 2 mM, see WO 97-31917) and 3-(t-butoxycarbonylamino)isoxazole (405 mg, 2.2 mM) were suspended by stirring in dry tetrahydrofuran (15 ml) under nitrogen in an ice-bath. Tributylphosphine (444 mg, 2.2 mM) followed by 1,1'-(azo-dicarbonyl)dipiperidine (555 mg, 2.2 mM) dissolved in tetrahydrofuran (10 ml) were added. The mixture was then stirred 18 hours, allowing the temperature to rise to ambient, then filtered, and the filter cake washed with tetrahydrofuran. The combined filtrates were evaporated and the residue purified by chromatography on a 10 g reversed phase C18 column, eluting with a gradient from 10 to 50% acetonitrile in water containing 0.1% trifluoroacetic acid. Relevant fractions were combined, evaporated, and the residue rechromatographed on a 10 g silica Mega Bond Elut® column, eluting with a gradient increasing in polarity from 0 to 20% methanol in dichloromethane. Relevant fractions were combined and evaporated to give the desired product (104 mg). MS (ESP): 474 (MH$^+$) for $C_{22}H_{24}FN_5O_6$ NMR (DMSO-d$_6$) δ: 1.49 (s, 9H); 3.92 (m, 1H); 4.00 (m, 1H); 4.27 (m, 2H); 4.50 (s, 2H); 5.05 (m, 1H); 6.85 (d, 1H); 7.53 (t, 1H); 7.66 (d, 1H); 7.76 (overlapping m, 2H); 8.67 (d, 1H); 8.80 (d, 1H). (H of OH missing-exchanged).

EXAMPLE 9

5(S)Isoxazol-3-ylaminomethyl-3-(4-(2-methylimidazol-1-yl)-3-fluorophenyl)oxazolidin-2-one Using essentially the technique of Example 8, but starting from 3-(4-(2-methylimidazol-1-yl)-3-fluorophenyl)-5(R)—(N-(t-butoxycarbonyl)isoxazol-3-ylaminomethyl)oxazolidin-2-one (510 mg, 1.12 mM), and isolating finally by extraction into dichloromethane gave title product (358 mg).

NMR (DMSO-$d_6$) δ: 2.16 (s, 3H); 3.46 (t, 2H); 3.87 (dd, 1H); 4.22 (t, 1H); 4.93 (m, 1H); 6.01 (d, 1H); 6.53 (t, 1H); 6.93 (d, 1H); 7.21 (d, 1H); 7.46 (dd, 1H); 7.55 (t, 1H); 7.75 (dd, 1H); 8.39 (d, 1H). MS (ESP): 358 (MH$^+$) for $C_{17}H_{16}FN_5O_3$ The intermediates for this compound were prepared as follows:

3-Fluoro-4(2-methylimidazol-1-yl)nitrobenzene

2-Methylimidazole (9.02 g, 0.11 M) and N,N-diisopropylethylamine (32.2 g, 0.25 M) were dissolved in acetonitrile (160 ml), and 3,4-difluoronitrobenzene (15.9 g, 0.1 M) added. The mixture was stirred and heated to reflux under nitrogen for 24 hours. Solvent was evaporated, the residue dissolved in ethyl acetate (300 ml), washed with water (150 ml), brine (150 ml), and dried (magnesium sulfate). The residue was recrystallised from a mixture of ethyl acetate (25 ml) and cyclohexane (150 ml) with the addition of charcoal to give the title compound (11.5 g), mp 106–107°.

NMR (DMSO-$d_6$) δ: 2.25 (s, 3H); 7.00 (d, 1H); 7.35 (t, 1H); 7.87 (t, 1H); 8.23 (dd, 1H); 8.43 (dd, 1H). MS (ESP): 222 (MH$^+$) for $C_{10}H_8FN_3O_2$

5-Amino-2-(2-methylimidazol-1-yl)fluorobenzene

3-Fluoro-4-(2-methylimidazol-1-yl)nitrobenzene (40 g, 0.181 M) was dissolved in a mixture of methanol (200 ml) and tetrahydrofuran (800 ml), cooled to 0° under nitrogen, and treated with ammonium formate (57 g, 0.905 M) followed by palladium on charcoal (10%, 2 g). The mixture was stirred at ambient temperature for 18 hours, filtered through celite, celite washed with methanol (100 ml), and filtrate evaporated to dryness. The residue was partitioned between ethyl acetate (800 ml) and 10% aqueous sodium bicarbonate (250 ml). The organic layer was separated, washed with brine (250 ml), dried (magnesium sulfate) and evaporated to give title compound (34.6 g).

NMR (DMSO-$d_6$) δ: 2.08 (s, 3H); 5.68 (s, 2H); 6.45 (overlapping m, 2H); 6.84 (d, 1H); 7.03 (overlapping m, 2H). MS (ESP): 192 (MH$^+$) for $C_{10}H_{10}FN_3$

5-Benzyloxycarbonylamino-2-(2-methylimidazol-1-yl)fluorobenzene

5-Amino-2-(2-methylimidazol-1-yl)fluorobenzene (34.25 g, 0.179 M) was dissolved in dry dichloromethane (600 ml) under nitrogen, and cooled to −5°. Pyridine (17.7 g, 0.224 M) was added, followed by benzyl chloroformate (33.7 g, 0.197 M) over 20 minutes. The mixture was stirred and the temperature allowed to rise to ambient over 16 hours. Aqueous sodium bicarbonate (5%, 250 ml) was added, the organic layer separated, the aqueous layer re-extracted with dichloromethane (2×300 ml), and combined extracts dried (magnesium sulfate). After filtration and evaporation, the residue was recrystallised from toluene (400 ml) to give title product (54.5 g).

NMR (DMSO-$d_6$) δ: 2.13 (s, 3H); 5.18 (s, 2H); 6.89 (s, 1H); 7.17 (s, 1H); 7.41 (overlapping m, 7H); 7.73 (dd, 1H); 10.21 (br, 1H). MS (ESP): 326 (MH$^+$) for $C_{18}H_{16}FN_3O_2$

3-(3-Fluoro-4-(2-methylimidazol-1-yl)phenyl)-5(R)-hydroxymethyloxazolidin-2-one 5-Benzyloxycarbonylamino-2-(2-methylimidazol-1-yl) fluorobenzene (54 g, 0.166 M) was dissolved in a mixture of dry tetrahydrofuran (600 ml) and 1,3-dimethyl-2,4,5,6-tetrahydro-2(1H)-pyrimidinone (100 ml) under nitrogen, cooled to −70°, and treated with a solution of n-butyllithium (1.6 M in isohexane, 114 ml), over 30 minutes. After stirring for 30 minutes at −70°, a solution of (R)glycidylbutyrate (26.35 g, 0.183 M) in dry tetrahydrofuran (50 ml) was added over 15 minutes. Stirring was continued for 16 hours allowing the temperature to rise to ambient. The mixture was treated with aqueous sodium bicarbonate (5%, 500 ml) and ethyl acetate (800 ml), the organic layer separated, and the aqueous extracted with further ethyl acetate (3×750 ml). The combined extracts were dried (magnesium sulfate) and evaporated, and the resulting oil triturated with diethyl ether. The resulting solid was recrystallisd from isopropanol to give the title compound (21.5 g).

NMR (DMSO-$d_6$) δ: 2.16 (s, 3H); 3.56 (dt, 1H); 3.69 (dt, 1H); 3.88 (dd, 1H); 4.15 (t, 1H); 4.74 (m, 1H); 5.24 (t, 1H); 6.92 (s, 1H); 7.20 (s, 1H); 7.48 (dd, 1H); 7.53 (t, 1H); 7.74 (dd, 1H). MS (ESP): 292 (MH$^+$) for $C_{14}H_{14}FN_3O_3$

3-(4-(2-methylimidazol-1-yl)-3-fluorophenyl)-5(R)-(N-(t-butoxycarbonyl)isoxazol-3-yl-aminomethyl)oxazolidin-2-one 3-(2-Methylimidazol-1-yl-3-fluorophenyl)-5(R)-hydroxymethyloxazolidin-2-one (582 mg, 2 mM), 3-(t-butoxycarbonylamino)isoxazole (552 mg, 3 mM), and triphenylphosphine (786 mg, 3 mM) were dissolved by stirring in dry N,N-dimethylformamide (10 ml) under nitrogen in an ice-bath. Diisopropylazodicarboxylate (606 mg, 3 mM) was added dropwise, and the mixture stirred 2 hours, allowing the temperature to rise to ambient. The mixture was diluted with ethyl acetate (100 ml), washed with water (100 ml), 2% aqueous sodium bicarbonate (100 ml), and brine (100 ml). After drying (magnesium sulfate), the residue was purified by chromatography on a 20 g silica Mega Bond Elut® column, eluting with a gradient increasing in polarity from 0 to 5% methanol in dichloromethane. Relevant fractions were combined to give the desired product (590 mg).

NMR (DMSO-$d_6$) δ: 1.47 (s, 9H); 2.14 (s, 3H); 3.91 (dd, 1H); 4.00 (dd, 1H); 4.25 (dd, 1H); 4.29 (t, 1H); 5.02 (m, 1H); 6.85 (d, 1H); 6.92 (d, 1H); 7.20 (d, 1H); 7.47 (dd, 1H); 7.55 (t, 1H); 7.71 (dd, 1H); 8.79 (d, 1H). MS (ESP): 458 (MH$^+$) for $C_{22}H_{24}FN_5O_5$

EXAMPLE 10

5(S)-Isoxazol-3-ylaminomethyl-3-(4-(4-methylimidazol-1-yl)-3-fluorophenyl)oxazolidin-2-one Using essentially the technique of Example 9, but starting from 3-(4-(4-methylimidazol-1-yl)-3-fluorophenyl)-5(R)-(N-(t-butoxycarbonyl)isoxazol-3-ylaminomethyl)oxazolidin-2-one (190 mg, 0.41 mM), and purifying the material from the dichloromethane extraction by chromatography on a 20 g silica Mega Bond Elut® column, eluting with a gradient increasing in polarity from 0 to 10% methanol in dichloromethane. Relevant fractions were combined to give title product (128 mg).

NMR (DMSO-d$_6$) δ: 2.15 (s, 3H); 3.45 (t, 2H); 3.86 (dd, 1H); 4.21 (t, 1H); 4.91 (m, 1H); 5.99 (d, 1H); 6.56 (t, 1H); 7.21 (d, 1H); 7.43 (dd, 1H); 7.63 (t, 1H); 7.74 (dd, 1H); 7.86 (d, 1H); 8.39 (d, 1H). MS (ESP): 358 (MH$^+$) for C$_{17}$H$_{16}$FN$_5$O$_3$ The intermediates for this compound were prepared as follows:

3-Fluoro-4-(4-methylimidazol-1-yl)nitrobenzene

4-Methylimidazole (45.1 g, 0.55 M) and N,N-diisopropylethylamine (161 g, 1.25 M) were dissolved in acetonitrile (800 ml), and 3,4-difluoronitrobenzene (79.5 g, 0.5 M) added. The mixture was stirred and heated to reflux under nitrogen for 24 hours. Solvent was evaporated, the residue dissolved in ethyl acetate (800 ml), washed with water (400 ml), brine (200 ml), and dried (magnesium sulfate). The residue was dissolved in toluene (250 ml), treated with charcoal, filtered, and diluted with hot cyclohexane (75 ml) to crystallise 3-fluoro-4-(4-methylimidazol-1-yl)nitrobenzene (64.7 g).

NMR (DMSO-d$_6$) δ: 2.18 (s, 3H); 7.29 (s, 1H); 7.92 (t, 1H); 8.07 (s, 1H); 8.18 (dd, 1H); 8.38 (dd, 1H). MS (ESP): 222 (MH$^+$) for C$_{11}$H$_8$FN$_3$O$_2$ 5-Amino-2-(4-methylimidazol-1-yl)fluorobenzene 3-Fluoro-4-(4-methylimidazol-1-yl)nitrobenzene (64.7 g, 0.293 M) was dissolved in a mixture of methanol (200 ml) and tetrahydrofuran (800 ml), cooled to 0° under nitrogen, and treated with ammonium formate (99.3 g, 1.46 M) followed by palladium on charcoal (10%, 2.5 g). The mixture was stirred at ambient temperature for 48 hours, filtered through celite, celite washed with methanol (200 ml), and filtrate evaporated to dryness. The residue was partitioned between ethyl acetate (800 ml) and 10% aqueous sodium bicarbonate (250 ml). The organic layer was separated, washed with brine (250 ml), dried (magnesium sulfate) and evaporated to give title compound (50.6 g).

NMR (DMSO-d$_6$) δ: 2.12 (s, 3H); 5.60 (br s, 2H); 6.42 (dd, 1H); 6.47 (dd, 1H); 6.98 (s, 1H); 7.11 (t, 1H); 7.60 (s, 1H). MS (ESP): 192 (MH$^+$) for C$_{10}$H$_{10}$FN$_3$ 5-Benzyloxycarbonylamino-2-(4-methylimidazol-1-yl)fluorobenzene 5-Amino-2-(4-methylimidazol-1-yl)fluorobenzene (50.6 g, 0.265 M) was dissolved in dry dichloromethane (800 ml) under nitrogen, and cooled to −5°. Pyridine (26.1 g, 0.33 M) was added, followed by benzyl chloroformate (49.9 g, 0.292 M) over 30 minutes. The mixture was stirred and the temperature allowed to rise to ambient over 16 hours. Aqueous sodium bicarbonate (5%, 350 ml) was added, the organic layer separated, and the aqueous layer re-extracted with dichloromethane (2×200 ml), and combined organics dried (magnesium sulfate). After filtration and evaporation, the residue was recrystallised from toluene (300 ml) to give title product (80 g).

NMR (DMSO-d$_6$) δ: 2.15 (s, 3H); 5.16 (s, 2H); 7.13 (s, 1H); 7.31 (dd, 1H); 7.41 (m, 5H); 7.48 (t, 1H); 7.57 (dd, 1H); 7.78 (s, 1H); 10.15 (br s, 1H). MS (ESP): 326 (MH$^+$) for C$_{18}$H$_{16}$N$_3$O$_2$ 3-(3-Fluoro-4-(4-methylimidazol-1-yl)phenyl)-5(R)-hydroxymethyloxazolidin-2-one 5-Benzyloxycarbonylamino-2-(4-methylimidazol-1-yl) fluorobenzene (54 g, 0.166 M) was dissolved in a mixture of dry tetrahydrofuran (600 ml) and 1,3-dimethyl-2,4,5,6-tetrahydro-2(1H)-pyrimidinone (100 ml) under nitrogen, cooled to −70°, and treated with a solution of n-butyllithium (1.6 M in isohexane, 114 ml), over 30 minutes. After stirring for 30 minutes at 25–70°, a solution of (R)-glycidylbutyrate (26.35 g, 0.183 M) in dry tetrahydrofuran (50 ml) was added over 15 minutes. Stirring was continued for 16 hours allowing the temperature to rise to ambient. The mixture was treated with aqueous sodium bicarbonate (5%, 500 ml) and ethyl acetate (800 ml), and undissolved solid was removed and washed well with diethyl ether to give title product (16.3 g).

The aqueous layer was further extracted with ethyl acetate (2×750 ml), the combined extracts dried (magnesium sulfate) and evaporated, and the residue triturated with diethyl ether. The resulting solid was recrystallisd from ethanol to give more product (10.9 g).

NMR (DMSO-d$_6$) δ: 2.13 (s, 3H); 3.56 (dd, 1H); 3.68 (dd, 1H); 3.86 (dd, 1H); 4.11 (t, 1H); 4.73 (m, 1H); 5.21 (br, 1H); 7.18 (s, 1H); 7.45 (dd, 1H); 7.60 (t, 1H); 7.73 (dd, 1H); 7.83 (s, 1H). MS (ESP): 292 (MH$^+$) for C$_{14}$H$_{14}$FN$_3$O$_3$ 3-(3-fluoro-4-(4-methylimidazol-1-yl)phenyl)-5(R)-methanesulfonyloxymethyloxazolidin-2-one 3-(3-Fluoro-4-(4-methylimidazol-1-yl)phenyl)-5(R)-hydroxymethyloxazolidin-2-one (11.8 g, 40.5 mM) was stirred in a mixture of pyridine (200 ml) and triethylamine (4.86 g, 48.2 mM) under nitrogen in an ice-bath. Methanesulfonyl chloride (5.16 g, 45 mM) was added dropwise, and the mixture stirrd for 2 hours, allowing the temperature to rise to ambient. Solvent was evaporated, and the residue stirred vigorously with a mixture of aqueous sodium bicarbonate (5%, 200 ml) and isohexane (200 ml). The precipitate was filtered, washed with water then isohexane, and dried. The residue was recrystallised from hot acetone (200 ml) by dilution with isohexane (300 ml) to give the title product (11.7 g), mp 151–153°.

NMR (DMSO-d$_6$); δ: 2.16 (s, 3H); 3.27 (s, 3H); 3.88 (dd, 1H); 4.24 (t, 1H); 4.47 (dd, 1H); 4.54 (dd, 1H); 5.04 (m, 1H); 7.20 (d, 1H); 7.45 (dd, 1H); 7.63 (t, 1H); 7.73 (dd, 1H); 7.85 (t, 1H). MS (EI): 369 (M$^+$) for C$_{15}$H$_{16}$FN$_3$O$_5$S 3-(4-(4-methylimidazol-1-yl]-3-fluorophenyl)-5(R)-(N-(t-butoxycarbonyl)isoxazol-3-yl-aminomethyl) oxazolidin-2-one Sodium hydride (50% in oil, 72 mg, 1.5 mM) was stirred in N,N-dimethylformamide (3 ml) under nitrogen, and 3-(t-butoxycarbonylamino)isoxazole (276 mg, 1.5 mM), dissolved in N,N-dimethylformamide (4 ml) added. After stirring for 10 minutes, 3-(4-methylimidazol-1-yl-3-fluorophenyl)-5(R)-methanesulfonyloxymethyloxazolidin-2-one (369 mg, 1 mM) was added, the mixture warmed to 35° for 1.5 hours. The mixture was diluted with aqueous sodium bicarbonate (30 ml), extracted with ethyl acetate (3×20 ml), and the extract washed with water (2×20 ml), and brine (20 ml). After drying (magnesium sulfate), the residue was purified by chromatography on a 20 g silica Mega Bond Elut® column, eluting with a gradient increasing in polarity from 0 to 50% acetone in dichloromethane. Relevant fractions were combined to give the desired product (228 mg).

NMR (DMSO-d$_6$) δ: 1.49 (s, 9H); 2.17 (s, 3H); 3.90 (dd, 1H); 4.01 (m, 1H); 4.25 (t, 1H); 4.28 (dd, 1H); 5.04 (m, 1H); 6.86 (d, 1H); 7.22 (d, 1H); 7.46 (dd, 1H); 7.63 (t, 1H); 7.72 (dd, 1H); 7.86 (d, 1H); 8.81 (d, 1H). MS (ESP): 458 (MH$^+$) for $C_{22}H_{24}FN_5O_5$

EXAMPLE 11

5(S)-Isoxazol-3-ylaminomethyl-3-(4-(3(S)-(t-butoxycarbonyl)aminopyrrolidin-1-yl)-3-fluorophenyl)oxazolidin-2-one The title compound was prepared using essentially the method of Example 7, starting from 3-(4-(3(S)-(t-butoxycarbonyl)aminopyrrolidin-1-yl)-3-fluorophenyl)-5(R)-N-(2,2,2-trichloroethyloxycarbonyl)isoxazol-3-ylamininomethyl)oxazolidin-2-one (320 mg, 0.5 mM). The residue after filtration and evaporation was partitioned between water (10 ml) and ethyl acetate (10 ml), and the organic phase washed with water (2×10 ml), aqueous sodium bicarbonate (10 ml), dried (magnesium sulfate), and evaporated. Recrystallisation from isopropanol (40 ml) gave the desired product (173 mg).

NMR (DMSO-d$_6$) δ: 1.37 (s, 9H); 1.80 (hextet, 1H); 2.07 (hextet, 1H); 3.10 (m, 1H); 3.24 (m overlapped by H$_2$O, ~1H); 3.42 (overlapping m, 3H); 3.48 (m, 1H); 3.74 (dd, 1H); 4.06 (overlapping m, 2H); 4.81 (m, 1H); 5.98 (d, 1H); 6.50 (t, 1H); 6.71 (t, 1H); 7.07 (dd, 1H); 7.12 (br, 1H); 7.37 (dd, 1H); 8.37 (d, 1H).

MS (ESP): 462 (MH$^+$) for $C_{22}H_{28}FN_5O_5$

The intermediates for this compound were prepared as follows:

3-Fluoro-4-(3(S)-(t-butoxycarbonyl)aminopyrrolidin-1-yl)nitrobenzene 3,4-Difluoronitrobenzene (17.1 g, 0.108 M) was dissolved in acetonitrile (300 ml), and treated with N,N-diisopropylethylamine (34.8 g, 0.27 M) and 3(S)-(t-butoxycarbonyl)-aminopyrrolidine (20 g, 0.108 M). The mixture was stirred and heated to reflux for 18 hours. Solvent was evaporated, and the residue dissolved in ethyl acetate (600 ml). The organic layer was washed with water (150 ml), aqueous sodium dihydrogen phosphate (5% in water, 150 ml), aqueous sodium bicarbonate (100 ml), brine (100 ml) and dried (magnesium sulfate). Evaporation gave the desired product as a yellow solid (33.5 g), of sufficient quality for use without purification.

NMR (DMSO-d$_6$) δ: 1.36 (s, 9H); 1.87 (m, 1H); 2.08 (m, 1H); 3.36 (m, 1H); 3.54 (m, 1H); 3.62 (m, 1H); 3.73 (m, 1H); 4.09 (m, 1H); 6.72 (t, 1H); 7.19 (d, 1H); 7.88 (overlapping m, 2H). MS (ESP): 326 (MH$^+$) for $C_{15}H_{20}FN_3O_4$ 5-Amino-2-(3(S)-(t-butoxycarbonyl)aminopyrrolidin-1 yl)fluorobenzene 3-Fluoro-4-(3(S)-(t-butoxycarbonyl)aminopyrrolidin-1-yl)nitrobenzene (33.5 g, 0.103 M) was dissolved in ethyl acetate (500 ml) treated with palladium catalyst (10% on carbon, 5 g) and hydrogenated at atmospheric pressure until the theoretical uptake of gas. After filtration through celite and evaporation, the required product was obtained as a red gum of sufficient quality for use without purification (30.4 g).

NMR (DMSO-d$_6$) δ: 1.35 (s, 9H); 1.71 (m, 1H); 2.06 (m, 1H); 2.87 (dd, 1H); 3.05 (m, 1H); 3.11 (m, 1H); 3.26 (m overlapping H$_2$O, ~1H); 3.97 (m, 1H); 4.68 (s, 2H); 6.25 (dd, 1H); 6.31 (dd, 1H); 6.51 (t, 1H); 7.03 (d, 1H). MS (ESP): 296 (MH$^+$) for $C_{15}H_{22}FN_3O_2$ 5-Ethoxycarbonylamino-2-(3(S)-(t-butoxycarbonyl)aminopyrrolidin 1-yl)fluorobenzene 5-Amino-2-(3(S)-(t-butoxycarbonyl)aminopyrrolidin-1-yl)fluorobenzene (30.4 g, 0.103 M) was dissolved in dry pyridine (150 ml) and cooled under nitrogen with stirring to 0°. Ethyl chloroformate (12.3, 0.113 M) was added dropwise, and the mixture stirred 1 hour at the same temperature. Ice-water (250 ml) was added, and stirring continued for 1 hour. The resulting precipitate was collected, washed thoroughly with water, and air dried. The residue was treated with toluene, azeotroped to half volume, then treated with isohexane (500 ml), to precipitate the desired product (35.3 g).

NMR (DMSO-d$_6$) δ: 1.21 (t, 3H); 1.37 (s, 9H); 1.77 (m, 1H); 2.06 (m, 1H); 3.04 (m, 1H); 3.20 (dd, 1H); 3.30 (m overlapping H$_{20}$, 1H); 3.42 (m, 1H); 4.02 (br, 1H); 4.08 (q, 2H); 6.63 (t, 1H); 7.02 (d, 1H); 7.08 (br, 1H); 7.22 (d, 1H); 9.38 (s, 1H). MS (ESP): 368 (MH$^+$) for $C_{18}H_{26}FN_3O_4$ 3-(3-Fluoro-4-(3(S)-(t-butoxycarbonyl)aminopyrrolidin-1-yl)-5(R)-hydroxymethyloxazolidin-2-one 5-Ethoxycarbonylamino-2-(3(S)-(t-butoxycarbonyl)aminopyrrolidin-1-yl)fluorobenzene (35.2 g, 0.096 M) was dissolved in dry tetrahydrofuran (400 ml) under nitrogen, cooled to −70°, and treated dropwise over 20 minutes with a solution of lithium t-butoxide, prepared from t-butanol (9.3 g, 123 mM) in dry tetrahydrofuran (70 ml) and n-butyl lithium (66 ml, 1.6 M in hexane). After stirring for 20 minutes, (R)-glycidylbutyrate (15.2 g, 0.102 M) in tetrahydrofuran (20 ml) was added over 10 minutes, and the temperature allowed to rise to ambient over 16 hours. The mixture was treated with methanol (10 ml), stirred at ambient temperature for 10 minutes, then treated with a mixture of 5% aqueous sodium bicarbonate (250 ml) and ethyl acetate (500 ml). The precipitate was collected and washed well with ethyl acetate and water to give the desired product (19.5 g). The filtrate was separated into an organic layer, which was dried (magnesium sulfate) and evaporated. The residue was refluxed briefly with ethyl acetate (100 ml), cooled, and filtered to give further product (16.6 g)

NMR (DMSO-d$_6$) δ: 1.37 (s, 9H); 1.79 (m, 1H); 2.07 (m, 1H); 3.08 (m, 1H); 3.24 (m overlapping H$_2$O, ~1H); 3.36 (m, 1H); 3.48 (m, 1H); 3.53 (d, 1H); 3.63 (d, 1H); 3.74 (dd, 1H); 3.99 (t, 1H); 4.04 (m, 1H); 4.63 (m, 1H); 5.15 (s, 1H); 6.71 (t, 1H); 7.08 (dd over-lapping br, 2H); 7.39 (dd, 1H). MS (ESP): 396 (MH$^+$) for $C_{19}H_{26}FN_3O_5$ 3-(4-(3-(t-Butoxycarbonyl)aminopyrrolidin-1-yl)-3-fluorophenyl)-5(R)-(N-(2,2,2-trichloroethyloxycarbonyl)isoxazol-3-ylaminomethyl)oxazolidin-2-one The title compound was prepared using essentially the method of Example 7, starting from 3-(3-fluoro-4-(3(S)-(t-butoxycarbonyl)aminopyrrolidin-1-yl)-5(R)-hydroxymethyloxazolidin-2-one (2.0 g, 5.06 mM). The crude material was purified by chromatography on a 90 g Biotage silica column, eluting with a gradient increasing in polarity from 0 to 5% ethyl acetate in dichloromethane. Relevant fractions were combined and evaporated to give the desired product (2.92 g).

NMR (DMSO-d$_6$) δ: 1.38 (s, 9H); 1.81 (hextet, 1H); 2.08 (hextet, 1H); 3.11 (m, 1H); 3.25 (m overlapping H$_2$O, ~1H);

3.37 (m, 1H); 3.48 (m, 1H); 3.82 (dd, 1H); 4.03 (m, 1H); 4.13 (overlapping m, 2H); 4.35 (dd, 1H); 4.98 (d overlapping m, 2H); 5.08 (d, 1H); 6.71 (t, 1H); 6.88 (d, 1H); 7.08 (dd overlapping br, 2H); 7.34 (dd, 1H); 8.89 (d, 1H). MS (ESP): 636 (MH$^+$) for $C_{25}H_{29}Cl_3FN_5O_7$

EXAMPLE 12

5(S)-Isoxazol-3-ylaminomethyl-3-(4-(3(S)-acetamidopyrrolidin-1-yl)-3-fluorophenyl)oxazolidin-2-one The title compound was prepared using essentially the method of Example 11, starting from 3-(4-(3(S)-acetamidopyrrolidin-1-yl)-3-fluorophenyl)-5(R)—(N-(2,2,2-trichloroethyloxycarbonyl)isoxazol-3-ylaminomethyl)oxazolidin-2-one (250 mg, 0.432 mM). The residue after the extractive work-up was purified by chromatography on a 10 g silica Mega Bond Elut® column, eluting with a gradient increasing in polarity from 0 to 10% methanol in dichloromethane. Relevant fractions were combined and evaporated to give the desired product (104 mg).

NMR (DMSO-d$_6$) δ: 1.78 (s overlapping m, 4H); 2.11 (hextet, 1H); 3.09 (m, 1H); 3.24 (m overlapped by H$_2$O, ~1H); 3.40 (t overlapping m, 3H); 3.47 (m, 1H); 3.72 (dd, 1H); 4.06 (t, 1H); 4.26 (hextet, 1H); 4.81 (m, 1H); 5.97 (d, 1H); 6.49 (t, 1H); 6.72 (t, 1H); 7.08 (dd, 1H); 7.39 (dd, 1H); 8.08 (d, 1H); 8.37 (d, 1H). MS (ESP): 404 (MH$^+$) for $C_{19}H_{22}FN_5O_4$ The intermediates for this compound were prepared as follows:

3-(4-(3(S)-Aminopyrrolidin-1-yl)-3-fluorophenyl)-5 (R)-(N-(2,2,2-trichloro-ethyloxycarbonyl)isoxazol-3-ylaminomethyl)oxazolidin-2-one 3-(4-(3(S)-(t-Butoxycarbonyl)aminopyrrolidin-1-yl)-3-fluorophenyl)-5(R)-(N-(2,2,2-trichloroethyloxycarbonyl) isoxazol-3-ylaminomethyl)oxazolidin-2-one (1.03 g, 1.62 mM) was dissolved in dichloromethane (5 ml) under nitrogen and treated with a solution of hydrogen chloride in ethanol (3.8 M, 25 ml). After stirring 5 hours at ambient temperature, solvent was removed, and the residue evaporated repeatedly with portions of dichloromethane to give the hydrochloride salt of the desired product as a white foam (962 mg).

NMR (DMSO-d$_6$) δ: 2.02 (hextet, 1H); 2.25 (hextet, 1H); 3.26 (dd, 1H); 3.42 (m overlapped by solvent, 1H); 3.53 (m, 2H); 3.84 (dd overlapping m, 2H); 4.15 (m, 2H); 4.35 (dd, 1H); 4.97 (d, 1H); 5.02 (m, 1H); 5.08 (d, 1H); 6.77 (t, 1H); 6.88 (d, 1H); 7.12 (dd, 1H); 7.39 (dd, 1H); 8.48 (br, 3H); 8.91 (d, 1H). (+1 proton for HCL salt). MS (ESP): 536 (MH$^+$) for $C_{20}H_{21}Cl_3FN_5O_5$ 3-(4-(3(S)-Acetamidopyrrolidin-1-yl)-3-fluorophenyl)-5(R)-(N-(2,2,2-trichloro-ethyloxycarbonyl)isoxazol-3-ylaminomethyl)oxazolidin-2-one 3-(4-(3(S)-Aminopyrrolidin-1-yl)-3-fluorophenyl)-5(R)-(N-(2,2,2-trichloroethyl-oxycarbonyl)isoxazol-3-ylaminomethyl)oxazolidin-2-one hydrochloride salt (400 mg, 0.74 mM) was dissolved in water (5 ml) and treated with aqueous sodium bicarbonate solution (5 ml) and dichloromethane (10 ml) in an ice-bath. Acetic anhydride (216 mg, 2 mM) was added, the mixture stirred 18 hours, allowing the temperature to rise to ambient, followed by addition of a further portion of acetic anhydride (216 mg), and a further period of 10 hours stirring. The organic phase was separated, washed with aqueous sodium dihydrogen phosphate (2%, 2×15 ml), brine (10 ml), and dried (magnesium sulfate). Evaporation gave the desired product (338 mg).

NMR (DMSO-d$_6$) δ: 1.79 (s overlapping m, 4H); 2.11 (hextet, 1H); 3.11 (m, 1H); 3.26 (m overlapped by H$_2$O, ~1H); 3.40 (dd, 1H); 3.49 (m, 1H); 3.82 (dd, 1H); 4.13 (t overlapping dd, 2H); 4.27 (dd, 1H); 4.35 (dd, 1H); 4.97 (d, 1H); 5.01 (m, 1H); 5.07 (d, 1H); 6.73 (t, 1H); 6.88 (d, 1H); 7.08 (dd, 1H); 7.35 (dd, 1H); 8.08 (d, 1H); 8.89 (d, 1H). MS (ESP): 578 (MH$^+$) for $C_{22}H_{23}Cl_3FN_5O_6$

EXAMPLE 13

5(S)-Isoxazol-3-ylaminomethyl-3-(4-(3(S)-methanesulfonamido-pyrrolidin-1-yl)-3-fluorophenyl)oxazolidin-2-one The title compound was prepared using essentially the method of Example 11, starting from 3-(4-(3(S)-methanesulfonamido-pyrrolidin-1-yl)-3-fluorophenyl)-5(R)-(N-(2,2,2-trichloroethyloxycarbonyl)isoxazol-3-ylaminomethyl)oxazolidin-2-one (250 mg, 0.407 mM). The residue after the extractive work-up was purified by chromatography on a 10 g silica Mega Bond Elut® column, eluting with a gradient increasing in polarity from 0 to 7% methanol in dichloromethane. Relevant fractions were combined and evaporated to give the desired product (94 mg).

NMR (DMSO-d$_6$) δ: 1.86 (hextet, 1H); 2.19 (hextet, 1H); 2.94 (s, 3H); 3.20 (m, 1H); 3.27 (m overlapped by H$_2$O, ~1H); 3.34 (m, 1H); 3.40 (t, 2H); 3.54 (t, 1H); 3.72 (dd, 1H); 3.97 (m, 1H); 4.06 (m, 1H); 4.81 (m, 1H); 5.98 (d, 1H); 6.48 (t, 1H); 6.72 (t, 1H); 7.08 (dd, 1H); 7.35 (s, 1H); 7.37 (dd, 1H); 8.36 (d, 1H). MS (ESP): 440 (MH$^+$) for $C_{18}H_{22}FN_5O_5S$ The 3-(4-(3(S)-Methanesulfonamidopyrrlidin-1-yl)-3-fluorophenyl)-5(R)-(N-(2,2,2-trichloroethyloxycarbonyl) isoxazol-3-ylaminomethyl)oxazolidin-2-one intermediate was prepared as follows:

Using essentially the method for the intermediate of Example 12, starting from 3-(4-(3(S)-aminopyrrolidin-1-yl)-3-fluorophenyl)-5(R)-(N-(2,2,2-trichloroethyloxycarbonyl)isoxazol-3-ylaminomethyl)oxazolidin-2-one hydrochloride salt (400 mg, 0.74 mM) and methanesulfonyl chloride gave the desired product (361 mg).

NMR (DMSO-d$_6$) δ: 1.87 (hextet, 1H); 2.19 (hextet, 1H); 2.97 (s, 3H); 3.20 (m, 1H); 3.30 (m, 1H); 3.37 (m, 1H); 3.54 (m overlapped by H$_{20}$, 1H); 3.83 (dd, 1H); 3.97 (dd, 1H); 4.13 (dd overlapping m, 2H); 4.36 (dd, 1H); 4.97 (d, 1H); 5.02 (m, 1H); 5.07 (d, 1H); 6.74 (t, 1H); 6.88 (d, 1H); 7.09 (dd, 1H); 7.36 (dd overlapping br, 2H); 8.89 (d, 1H). MS (ESP): 578 (MH$^+$) for $C_{21}H_{23}Cl_3FN_5O_7S$

EXAMPLE 14

3-(4-(3(S)-Methoxycarbonylaminopyrrolidin-1-yl)-3-fluorophenyl)-5(S)-(isoxazol-3-ylaminomethyl)oxazolidin-2-one The title compound was prepared using essentially the method of Example 11, starting from 3-(4-(3(S)-methoxycarbonylaminopyrrolidin-1-yl)-3-fluorophenyl)-5(R)-(N-(2,2,2-trichloroethyloxycarbonyl)isoxazol-3-ylaminomethyl) oxazolidin-2-one (250 mg, 0.407 mM). The residue after the extractive work-up was purified by chromatography on a 10 g silica Mega Bond Elut® column, eluting with a gradient increasing in polarity from 0 to 100% ethyl acetate in dichloromethane. Relevant fractions were combined and evaporated to give the desired product (91 mg).

NMR (DMSO-d$_6$) δ: 1.82 (hextet, 1H); 2.10 (hextet, 1H); 3.13 (m, 1H); 3.26 (m overlapped by H$_2$O, ~1H); 3.39 (m, 3H); 3.48 (t, 1H); 3.52 (s, 3H); 3.73 (dd, 1H); 4.07 (t, 1H); 4.10 (m, 1H); 4.82 (m, 1H); 5.98 (d, 1H); 6.48 (t, 1H); 6.71 (t, 1H); 7.08 (dd, 1H); 7.37 (dd, 1H); 7.42 (s, 1H); 8.35 (d, 1H).

MS (ESP): 420 (MH$^+$) for C$_{19}$H$_{22}$FN$_5$O$_5$

The 3-(4-(3(S)-Methoxycarbonylaminopyrrolidin-1-yl)-3-fluorophenyl)-5(R)-(N-(2,2,2-trichloroethyloxycarbonyl)isoxazol-3-ylaminomethyl)oxazolidin-2-one intermediate was prepared as follows:

Using essentially the method for the intermediate of Example 12, starting from 3-(4-(3(S)-aminopyrrolidin-1-yl)-3-fluorophenyl)-5(R)-(N-(2,2,2-trichloroethyloxycarbonyl)isoxazol-3-ylaminomethyl)oxazolidin-2-one hydrochloride salt (360 mg, 0.63 mM) and methyl chloroformate gave the desired product (280 mg).

NMR (DMSO-d$_6$) δ: 1.84 (hextet, 1H); 2.13 (hextet, 1H); 3.15 (m, 1H); 3.35 (m overlapped by H$_2$O, ~2H); 3.55 (s overlapping m, 4); 3.84 (dd, 1H); 4.13 (overlapping m, 3H); 4.36 (dd, 1H); 4.98 (d, 1H); 5.04 (m, 1H); 5.08 (d, 1H); 6.73 (t, 1H); 6.89 (d, 1H); 7.08 (dd, 1H); 7.35 (dd, 1H); 7.43 (br, 1H); 8.93 (d, 1H). MS (ESP): 594 (MH$^+$) for C$_{22}$H$_{23}$Cl$_3$FN$_5$O$_7$

EXAMPLE 15

3-(4=(3(S)-Acetoxyacetamidopyrrolidin-1-yl)-3-fluorophenyl)-5(S)-(isoxazol-3-ylaminomethyl)oxazolidin-2-one The title compound was prepared using essentially the method of Example 11, starting from 3-(4-(3(S)-acetoxyacetamidopyrrolidin-1-yl)-3-fluorophenyl)-5(R)-(N-(2,2,2-trichloroethyloxycarbonyl)isoxazol-3-ylaminomethyl)oxazolidin-2-one (390 mg, 0.62 mM). The residue after the extractive work-up was purified by chromatography on a 10 g silica Mega Bond Elut® column, eluting with a gradient increasing in polarity from 0 to 100% ethyl acetate in dichloromethane. Relevant fractions were combined and evaporated to give the desired product (100 mg).

NMR (DMSO-d$_6$) δ: 1.83 (hextet, 1H); 2.06 (s, 3H); 2.14 (hextet, 1H); 3.13 (m, 1H); 3.24 (m overlapped by H$_2$O, ~2H); 3.40 (t, 2H); 3.49 (m, 1H); 3.73 (dd, 1H); 4.06 (t, 1H); 4.32 (m, 1H); 4.42 (s, 2H); 4.81 (m, 1H); 5.97 (d, 1H); 6.49 (t, 1H); 6.73 (t, 1H); 7.08 (dd, 1H); 7.39 (dd, 1H); 8.23 (d, 1H); 8.36 (d, 1H). MS (ESP): 462 (MH$^+$) for C$_{21}$H$_{24}$FN$_5$O$_6$ The 3-(4-(3(S)-Acetoxyacetamidopyrrolidin-1-yl)-3-fluorophenyl)-5(R)-(N-(2,2,2-trichloro-ethyloxycarbonyl)isoxazol-3-ylaminomethyl)oxazolidin-2-one intermediate was prepared as follows:

3-(4-(3(S)-Aminopyrrolidin-1-yl)-3-fluorophenyl)-5(R)-(N-(2,2,2-trichloroethyl-oxycarbonyl)isoxazol-3-ylaminomethyl)oxazolidin-2-one hydrochloride salt (400 mg, 0.698 mM) was suspended in dichloromethane (10 ml) under nitrogen at 0°. Triethylamine (282 mg, 2.79 mM) was added, the solution treated dropwise with acetoxyacetyl chloride (145 mg, 1.05 mM), and then stirred for 1 hour at ambient temperature. The mixture was diluted with dichloromethane (10 ml), washed with aqueous sodium dihydrogen phosphate (10%, 10 ml), aqueous sodium bicarbonate (10 ml) and water (10 ml), and dried (magnesium sulfate). Trituration of the residue after evaporation with diethyl ether/isohexane (1:1, 10 ml) gave the desired product (440 mg).

NMR (DMSO-d$_6$) δ: 1.83 (hextet, 1H); 2.06 (s, 3H); 2.13 (hextet, 1H); 3.14 (m, 1H); 3.27 (m overlapped by H$_2$O, ~1H); 3.40 (m, 1H); 3.50 (m, 1H); 3.82 (dd, 1H); 4.13 (overlapping m, 2H); 4.33 (overlapping m, 2H); 4.52 (s, 2H); 4.97 (d, 1H); 5.03 (m, 1H); 5.07 (d, 1H); 6.74 (t, 1H); 6.88 (d, 1H); 7.09 (dd, 1H); 7.35 (dd, 1H); 8.25 (d, 1H); 8.89 (d, 1H). MS (ESP): 636 (MH$^+$) for C$_{24}$H$_{25}$Cl$_3$FN$_5$O$_8$

EXAMPLE 16

3-(4-(3(S)-Hydroxyacetamidopyrrolidin-1-yl)-3-fluorophenyl)-5(S)-(isoxazol-3-ylaminomethyl)oxazolidin-2-one 3-(4-(3(S)-Acetoxyacetamidopyrrolidin-1-yl)-3-fluorophenyl)-5(S)-(3-isoxazolylamino-methyl)oxazolidin-2-one (1051 mg, 0.23 mM) and potassium carbonate (300 mg, 2.2 mM) were stirred at ambient temperature under nitrogen in methanol (20 ml) for 20 minutes. The mixture was evaporated to dryness and triturated with water (10 ml) to gave the desired product (77 mg).

NMR (DMSO-d$_6$) δ: 1.83 (hextet, 1H); 2.14 (hextet, 1H); 3.20 (m, 1H); 3.29 (m overlapped by H$_{2O}$, 1H); 3.42 (t overlapping m, 3H); 3.49 (m, 1H); 3.75 (dd, 1H); 3.82 (s, 2H); 4.07 (t, 1H); 4.37 (m, 1H); 4.83 (m, 1H); 5.37 (br, 1H); 6.00 (d, 1H); 6.51 (t, 1H); 6.75 (t, 1H); 7.10 (dd, 1H); 7.41 (dd, 1H); 7.85 (d, 1H); 8.37 (d, 1H).

MS (ESP): 420 (MH$^+$) for C$_{19}$H$_{22}$FN$_5$O$_5$

EXAMPLE 17

3-(4-(3(S)-(2(S),3-Dihydroxypropanoyl)pyrrolidin-1-yl)-3-fluorophenyl)-5(S)-(isoxazol-3-ylaminomethyl)oxazolidin-2-one The title compound was prepared using essentially the method of Example 7, starting from 3-(4-(3(S)-(2,2-dimethyl-1,3-dioxolan-4(S)-ylcarbonamido)pyrrolidin-1-yl)-3-fluorophenyl)-5(R)-(N-(2,2,2-trichloroethyloxycarbonyl)isoxazol-3-ylaminomethyl)oxazolidin-2-one (380 mg, 0.572 mM). The residue after filtration and evaporation was dissolved in tetrahydrofuran (6 ml), treated with 2 M aqueous hydrochloric acid (4 ml), and stirred at ambient temperature for 20 hours. Excess anhydrous potassium carbonate was added, the solution filtered, evaporated, and the residue purified by chromatography on a 10 g silica Mega Bond Elut® column, eluting with a gradient increasing in polarity from 0 to 20% methanol in dichloromethane. Relevant fractions were combined and evaporated to give the desired product (130 mg).

NMR (DMSO-d$_6$) δ: 1.91 (hextet, 1H); 2.13 (hextet, 1H); 3.20–3.50 (overlapping m, ~7H); 3.57 (dd, 1H); 3.74 (dd, 1H); 3.87 (t, 1H); 4.08 (t, 1H); 4.35 (m, 1H); 4.83 (m, 1H); 6.00 (d, 1H); 6.50 (t, 1H); 6.73 (t, H); 7.11 (dd, 1H); 7.40 (dd, 1H); 7.80 (d, 1H); 8.38 (d, 1H). (2×OH exchanging, not seen). MS (ESP): 450 (MH$^+$) for C$_{20}$H$_{24}$FN$_5$O$_6$ The 3-(4-(3(S)-(2,2-dimethyl-1,3-dioxolan-4(S)-ylcarbonamido)pyrrolidin-1-yl)-3-fluorophenyl)-5(R)-(N-(2,2,2-trichloroethyloxycarbonyl)isoxazol-3-ylaminomethyl)oxazolidin-2-one intermediate was prepared as follows:

3-(4-(3(S)-Aminopyrrolidin-1-yl)-3-fluorophenyl)-5(R)-(N-(2,2,2-trichloroethyl-oxycarbonyl)isoxazol-3-ylaminomethyl)oxazolidin-2-one hydrochloride salt (400 mg, 0.698 mM) in pyridine (5 ml) was treated dropwise with a solution of 2,2-dimethyl-1,3-dioxolan-4(S)-ylcarbonyl chloride (200 mg, 1.2 mM) in dichloromethane (2 ml), and the mixture stirred 3 hours at ambient temperature. The mixture was diluted with ethyl acetate (15 ml) and water (15 ml), the organic layer separated, washed with aqueous sodium bicarbonate (10 ml) and brine (10 ml), and evaporated, then azeotroped with toluene (20 ml). The residue was purified by chromatography on a 10 g silica Mega Bond Elut® column, eluting with a gradient increasing in polarity from 0 to 100% ethyl acetate in dichloromethane. Relevant fractions were combined and evaporated to give the desired product (435 mg).

NMR (DMSO-$d_6$) δ: 1.30 (s, 3H); 1.37 (s, 3H); 1.89 (hextet, 1H); 2.13 Sextet, 1H); 3.20 (m, 1H); 3.24 (m overlapped by $H_2O$, ~1H); 3.39 (m, 1H); 3.48 (m, 1H); 3.82 (dd, 1H); 3.91 (dd, 1H); 4.12 (overlapping m, 3H); 4.33 (t overlapping m, 2H); 4.42 (dd, 2H); 4.97 (d, 1H); 5.02 (m, 1H); 5.06 (d, 1H); 6.75 (t, 1H); 6.87 (d, 1H); 7.08 (dd, 1H); 7.34 (dd, 1H); 7.94 (d, 1H); 8.89 (d, 1H). MS (ESP): 664 (MH$^+$) for $C_{26}H_{29}Cl_3FN_5O_8$

EXAMPLE 18

3-(4-(3(S)-(2-Methoxyethoxycarbonylamino)pyrrolidin-1-yl)-3-fluorophenyl)-5(S)-(isoxazol-3-ylaminomethyl)oxazolidin-2-one 3-(4-(3(S)-(2-Methoxyethoxycarbonylamino)pyrrolidin-1-yl)-3-fluorophenyl)-5(R)-(N-(2,2,2-trichloroethyloxycarbonyl)isoxazol-3-ylaminomethyl)oxazolidin-2-one (400 mg, 0.5 mM) was stirred in a mixture of acetic acid (10 ml) and water (2 ml). Zinc dust (203 mg, 3.1 mM) was added, and the mixture stirred 30 minutes at ambient temperature. The mixture was filtered through celite, and the residue after evaporation partitioned between ethyl acetate (10 ml) and aqueous sodium bicarbonate (15 ml). The organic phase was washed with sodium bicarbonate (2×15 ml), water (15 ml), dried (magnesium sulfate), and evaporated. The crude product was purified by chromatography on a 10 g Biotage silica column, eluting with a gradient from dichloromethane to ethyl acetate. Relevant fractions were combined to give the desired product (141 mg).

NMR (DMSO-$d_6$) δ: 1.83 (hextet, 1H); 2.09 (hextet, 1H); 3.13 (m, 1H); 3.26 (s, 3H); 3.40, 3.47 (t overlapping m, 7H); 3.73 (dd, 1H); 4.04 (overlapping m, 4H); 4.82 (m, 1H); 6.01 (d, 1H); 6.52 (t, 1H); 6.72 (t, 1H); 7.08 (dd, 1H); 7.39 (dd, 1H); 7.52 (d, 1H); 8.37 (d, 1H). MS (ESP): 464 (MH$^+$) for $C_{21}H_{26}FN_5O_6$ The 3-(4-(3(R)-(2-Methoxyethoxycarbonylamino)pyrrolidin-1-yl)-3-fluorophenyl)-5(R)-(N-(2,2,2-trichloroethyloxycarbonyl)isoxazol-3-ylaminomethyl)oxazolidin-2-one intermediate was prepared as follows:

Using essentially the method for the intermediate of Example 12, starting from 3-(4(3(S)-aminopyrrolidin-1-yl)-3-fluorophenyl)-5(R)-(N-2,2,2-trichloroethyloxycarbonyl) isoxazol-3-ylaminomethyl)oxazolidin-2-one hydrochloride salt (419 mg, 0.73 mM) and 2-methoxyethyl chloroformate (450 mg, 3.27 mM) gave the title compound (442 mg).

NMR (DMSO-$d_6$) δ: 1.82 (hextet, 1H); 2.09 (hextet, 1H); 3.13 (m, 1H); 3.23 (s, 3H); 3.27 (m, 1H); 3.39 (m, 1H); 3.46 (t overlapping m, 3H); 3.81 (dd overlapping m, 2H); 4.05 (m, 2H); 4.13 (m, 2H); 4.32 (m, 1H); 4.97 (d, 1H); 5.02 (m, 1H); 5.08 (d, 1H); 6.71 (t, 1H); 6.88 (d, 1H); 7.08 (dd, 1H); 7.34 (dd, 1H); 7.52 (d, 1H); 8.89 (d, 1H). MS (ESP): 638 (MH$^+$) for $C_{14}H_{27}FN_5O_8Cl_3$

EXAMPLE 19

3-(4-(3(R)-Methoxycarbonylaminopyrrolidin-1-yl)-3-fluorophenyl)-5(S)-(isoxazol-3-ylaminomethyl)oxazolidin-2-one The title compound was prepared using essentially the method of Example 11, starting from 3-(4-(3(R)-methoxycarbonylaminopyrrolidin-1-yl)-3-fluorophenyl)-5(R)-(N-(2,2,2-trichloroethyloxycarbonyl)isoxazol-3-ylaminomethyl)oxazolidin-2-one (1.38 g, 2.32 mM). The residue after the extractive work-up was purified by chromatography on a 20 g silica Mega Bond Elut® column, eluting with a gradient increasing in polarity from 0 to 100% ethyl acetate in dichloromethane. Relevant fractions were combined and evaporated to give the desired product (490 mg).

NMR (DMSO-$d_6$) δ: 1.81 (hextet, 1H); 2.11 (hextet, 1H); 3.10 (m, 1H); ); 3.24 (m overlapped by $H_2O$, ~1H); 3.42 (t overlapping m, 3H); 3.50 (s overlapping m, 4H); 3.73 (dd, 1H); 4.07 (t overlapping m, 2H); 4.81 (m, 1H); 5.98 (d, 1H); 6.49 (t, 1H); 6.72 (t, 1H); 7.08 (dd, 1H); 7.37 (dd, 1H); 7.43 (s, 1H); 8.37 (d, 1H). MS (ESP): 420 (MH$^+$) for $C_{19}H_{22}FN_5O_5$ The intermediates for this compound were prepared as follows:

3-Fluoro-4-(3(R)-(t-butoxycarbonyl)aminopyrrolidin-1-yl)nitrobenzene 3,4-Difluoronitrobenzene (16.03 g, 0.101 M) was dissolved in acetonitrile (300 ml), and treated with N,N-diisopropylethylamine (32.63 g, 0.253 M) and 3(R)-(t-butoxycarbonyl)-aminopyrrolidine (20.65 g, 0.111 M). The mixture was stirred and heated to reflux for 18 hours. Solvent was evaporated, and the residue treated with ethyl acetate (300 ml) and water (200 ml). The organic layer was washed with water (150 ml), citric acid solution (10% in water, 2×150 ml), and dried (magnesium sulfate). Evaporation gave the desired product as a yellow solid (32.7 g), of sufficient quality for use without purification.

NMR (CDCl$_3$) δ: 1.43 (s, 9H); 1.85 (m, 1H); 2.25 (m, 1H); 3.44 (dt, 1H); 3.65 (overlapping m, 2H); 3.84 (din, 1H); 4.34 (br m, 1H); 4.69 (br, 1H); 6.53 (t, 1H); 7.87 (dd, 1H); 7.92 (dd, 1H). MS (ESP): 326 (MH$^+$) for $C_{15}H_{20}FN_3O_4$ 5-Amino-2-(3(R)-(t-butoxycarbonyl)aminopyrrolidin-1-yl)fluorobenzene 3-Fluoro-4-(3(R)-(t-butoxycarbonyl)aminopyrrolidin-1-yl)nitrobenzene (32.7 g, 0.101 M) was dissolved in ethyl acetate (500 ml) treated with palladium catalyst (10% on carbon, 7.5 g) and hydrogenated at atmospheric pressure until the theoretical uptake of gas. After filtration through celite and evaporation, the required product was obtained as a red gum of sufficient quality for use without purification (29.85 g).

NMR (CDCl$_3$) δ: 1.44 (s, 9H); 1.82 (m, 1H); 2.27 (m, 1H); 3.11 (m, 2H); 3.37 (m, 2H); 3.43 (br, 2H); 4.27 (br m, 1H); 4.82 (br, 1H); 6.38 (dd, 1H); 6.44 (dd, 1H); 6.57 (t, 1H). MS (ESP): 296 (MH$^+$) for $C_{15}H_{22}FN_3O_2$ 5-Ethoxycarbonylamino-2-(3(R)-(t-butoxycarbonyl) aminopyrrolidin-1-yl)fluorobenzene 5-Amino-2-(3(R)-(t-butoxycarbonyl)aminopyrrolidin-1-yl)fluorobenzene (27.33 g, 0.093 M) was dissolved in dry pyridine (150 ml) and cooled under nitrogen with stirring to 0°. Ethyl chloroformate (11.01, 0.102 M) was added dropwise, and the mixture stirred 30 minutes at the same temperature. Ice-water (250 ml) was added, and stirring continued for 1 hour. The resulting precipitate was collected, washed thoroughly with water, and dried, to give the desired product of sufficient quality for use without purification (33.6 g).

NMR (DMSO-$d_6$) δ: 1.21 (t, 3H); 1.36 (s, 9H); 1.90 (m, 1H); 2.05 (m, 1H); 3.04 (m, 1H); 3.20 (m, 1H); 3.32 (m, 1H); 3.40 (m, 1H); 4.02 (br, 1H); 4.05 (q, 2H); 6.62 (t, 1H); 7.02 (d, 1H); 7.08 (d, 1H); 7.22 (d, 1H); 9.38 (br, 1H). MS (ESP): 368 (MH$^+$) for $C_{18}H_{26}FN_3O_4$ 3-(3-Fluoro-4(3(R)-(t-butoxycarbonyl)aminopyrrolidin-1-yl)-5(R)-hydroxymethyloxazolidin-2-one 5-Ethoxycarbonylamino-2-(3(R)-(t-butoxycarbonyl)aminopyrrolidin-1-yl)fluorobenzene (33.6 g, 0.092 M) was dissolved in dry tetrahydrofuran (300 ml) under nitrogen, cooled to −70°, and treated dropwise over 30 minutes with a solution of lithium t-butoxide (1 M in tetrahydrofuran, 100.7 ml), keeping the temperature below −65°. After stirring for 5 minutes, (R)-glycidylbutyrate (14.52 g, 0.101 M) was added, and stirring continued at −65° for 1 hour, before allowing the temperature to rise to ambient over 16 hours. The mixture was treated with methanol (50 ml), stirred at ambient temperature for 1 hour, and the precipitate collected and washed well with tetrahydrofuran to give the desired product (21.8 g)

NMR (DMSO-$d_6$) δ: 1.36 (s, 9H); 1.80 (m, 1H); 2.07 (m, 1H); 3.09 (m, 1H); 3.26 (t, 1H); 3.35 (m, 1H); 3.49 (m, 2H); 3.62 (m, 1H); 3.73 (dd, 1H); 3.98 (t, 1H); 4.04 (m, 1H); 4.63 (m, 1H); 5.15 (t, 1H); 6.70 (t, 1H); 7.09 (dd overlapping br, 2H); 7.39 (dd, 1H). MS (ESP): 396 (MH$^+$) for $C_{19}H_{26}FN_3O_5$ 3-(4-(3(R)-(t-Butoxycarbonyl)aminopyrrolidin-1-yl-3-fluorophenyl-5(R-(N-(2,2,2-trichloroethyloxycarbonyl)isoxazol-3-ylaminomethyl)oxazolidin-2-one The basic method for the intermediate of Example 7, starting from 3-(4-(3(R)-(t-butoxycarbonyl)aminopyrrolidin-1-yl)-3-fluorophenyl)-5(R)-hydroxymethyloxazolidin-2-one (2.0 g, 5.06 mM), was used. The crude product was purified by chromatography on a 90 g Biotage silica column, eluting with a gradient increasing in polarity from 0 to 5% ethyl acetate in dichloromethane. Relevant fractions were combined to give the desired product (1.56 g).

NMR (DMSO-$d_6$) δ: 1.37 (s, 9H); 1.81 (hextet, 1H); 2.08 (hextet, 1H); 3.09 (m, 1H); 3.25 (m overlapped by solvent, ~1H); 3.38 (dd, 1H); 3.48 (t, 1H); 3.82 (dd, 1H); 4.04 (m, 1H); 4.14 (m, 2H); 4.35 (dd, 1H); 4.97 (d, 1H); 5.01 (m, 1H); 5.07 (d, 1H); 6.71 (t, 1H); 6.88 (d, 1H); 7.08 (dd, 1H); 7.11 (br, 1H); 7.34 (dd, 1H); 8.89 (d, 1H). MS (ESP): 636(MH$^+$) for $C_{25}H_{29}Cl_3FN_5O_7$ 3-(4-(3(R)-Aminopyrrolidin-1-yl)-3-fluorophenyl)-5(R)-(N-(2,2,2-trichloroethyl-oxycarbonyl)isoxazol-3-ylaminomethyl)oxazolidin-2-one Using essentially the method for the intermediate of Example 12, starting from 3-(4-(3(R)-(t-butoxycarbonyl)aminopyrrolidin-1-yl)-3-fluorophenyl)-5(R-(N-(2,2,2-trichloroethyloxycarbonyl)isoxazol-3-ylaminomethyl)oxazolidin-2-one (2.18 g, 3.42 mM) gave the hydrochloride salt of the desired product as a white foam (1.79 g).

NMR (DMSO-$d_6$) δ: 2.02 (hextet, 1H); 2.26 (hextet, 1H); 3.25 (dd, 1H); 3.42 (m overlapped by solvent, ~1H); 3.53 (m, 2H); 3.83 (dd overlapping m, 2H); 4.15 (m, 2H); 4.35 (dd, 1H); 4.98 (d, 1H); 5.02 (m, 1H); 5.07 (d, 1H); 6.79 (t, 1H); 6.87 (d, 1H); 7.12 (dd, 1H); 7.39 (dd, 1H); 8.38 (br, 3H); 8.89 (d, 1H) (+1 proton for HCl salt). MS (ESP): 536 (MH$^+$) for $C_{20}H_{21}Cl_3FN_5O_5$ 3-(4-(3(R)-Methoxycarbonylaminopyrrolidin-1-yl)-3-fluorophenyl)-5(R)-(N-(2,2,2-trichloro-ethyloxycarbonyl)isoxazol-3-ylaminomethyl)oxazolidin-2-one Using essentially the method for the intermediate of Example 12, starting from 3-(4-(3(R)-aminopyrrolidin-1-yl)-3-fluorophenyl)-5(R)-(N-(2,2,2-trichloroethyloxycarbonyl)isoxazol-3-ylaminomethyl)oxazolidin-2-one hydrochloride salt (1.61 g, 2.81 mM) and methyl chloroformate gave the desired product (1.61 g).

NMR (DMSO-$_6$) δ: 1.82 (hextet, 1H); 2.11 (hextet, 1H); 3.13 (m, 1H); 3.28 (dd, 1H); 3.39 (dd, 1H); 3.52 (s overlapping m, 4H); 3.82 (dd, 1H); 4.14 (overlapping m, 3H); 4.36 (dd, 1H); 4.97 (d, 1H); 5.03 (m, 1H); 5.08 (d, 1H); 6.72 (t, 1H); 6.89 (d, 1H); 7.08 (dd, 1H); 7.35 (dd, 1H); 7.41 (br, 1H); 8.89 (d, 1H). MS (ESP): 594 (MH$^+$) for $C_{22}H_{23}Cl_3FN_5O_7$

EXAMPLE 20

3-(4-(1-(2(S),3-Dihydroxypropanoyl)-1,2,5,6-tetrahydropyrid-4-yl)-3,5-difluorophenyl)-5(S)-(3-methylisoxazol-5-ylaminomethyl)oxazolidin-2-one 3-(4-(1-(2,2-Dimethyl-1,3-dioxolan-4(S)-ylcarbonyl)-1,2,5,6-tetrahydropyrid-4-yl)-3,5-difluorophenyl)-5(R)(N-(t-butoxycarbonyl)-3-methylisoxazol-5-ylaminomethyl)oxazolidin-2-one (400 mg, 0.65 mM) was dissolved in dichloromethane (6 ml) and treated with trifluoroacetic acid (6 ml) at 0°. After stirring for 30 minutes at ambient temperature, water (1.2 ml) was added, and stirring continued for 1 hour. Solvent was removed, the residue dissolved in methanol (20 ml), and treated with aqueous ammonia to bring the pH to 7–8; solvent was removed, and the residue chromatographed on a 10 g silica Mega Bond Elut® column, eluting with a gradient increasing in polarity from 0 to 5% methanol in dichloromethane. Relevant fractions were combined and evaporated to give the desired product (181 mg).

NMR (DMSO-$d_6$) δ: 2.02 (s, 3H); 2.29 (m, 1H); 2.35 (m, 1H); 3.41 (t, 2H); 3.47 (m, 1H); 3.54 (m, 1H); 3.71 (m, 1H); 3.75 (dd, 1H); 4.04 (dd, 1H); 4.08 (m, 1H); 4.13 (t, 1H); 4.24 (m, 1H); 4.36 (t, 1H); 4.66 (t, 1H); 4.82 (m, 1H); 4.95 (t, 1H); 4.99 (s, 1H); 5.85 (s, 1H); 7.30 (d, 2H); 7.36 (t, 1H). MS (ESP): 479 (MH$^+$) for $C_{22}H_{24}F_2N_4O_6$ The intermediates for this compound were prepared as follows:

3-(4-(1-Benzyl-1,2,5,6-tetrahydropyrid-4-yl)-3,5-difluorophenyl)-5(R)-acetoxy-methyloxazolidin-2-one 3-(4-(1-Benzyl-1,2,5,6-tetrahydropyrid-4-yl)-3,5-difluorophenyl)-5(R)-hydroxy-methyloxazolidin-2-one (20 g, 50 mM, see WO 97-30995) was suspended by stirring in dry dichloromethane (400 ml) under nitrogen at 0°, and treated with triethylamine (5.5 g, 54.4 mM) and 4-dimethylaminopyridine (0.3 g, 2.7 mM). Acetic anhydride (5.3 g, 52 mM) was added dropwise to give a solution, which was stirred for 1 hour, allowing the temperature to rise to ambient. The mixture was shaken with 5% aqueous sodium bicarbonate (200 ml) until carbon dioxide evolution ceased. The organic phase was separated, dried (magnesium sulfate) and evaporated, then azeotroped with toluene (2×50 ml) to give semi-crystalline product of suffient purity for the next stage (24 g).

NMR (DMSO-$d_6$) δ: 2.03 (s, 3H); 2.30 (br, 2H); 2.61 (t, 2H); 3.04 (m, 2H); 3.58 (s, 2H); 3.82 (dd, 1H); 4.14 (t, 1H); 4.23 (dd, 1H); 4.30 (dd, 1H); 4.95 (m, 1H); 5.78 (s, 1H); 7.30 (s overlapping m, 7H). MS (ESP): 443 (MH$^+$) for $C_{24}H_{24}F_2N_2O_4$

3-(4-(1,2,5,6-Tetrahydropyrid-4-yl)-3,5-difluorophenyl)-5(R)-acetoxymethyloxazolidin-2-one Hydrochloride salt 3-(4-(1-Benzyl-1,2,5,6-tetrahydropyrid-4-yl)-3,5-difluorophenyl)-5(R)-acetoxy-methyloxazolidin-2-one (22.1 g, 50 mM) was stirred in dry dichloromethane (400 ml) under nitrogen at 0°, and treated dropwise with 1-chloroethyl chloroformate (8.58 g, 60 mM). After stirring 1 hour the reaction mixture was purified by rapid vacuum sinter chromatography on 300 g of silica prewashed with dichloromethane, eluting with a gradient increasing in polarity from 0 to 20% ethyl acetate in dichloromethane. Relevant fractions were combined to give the intermediate chloroethyl carbamate as a gum (20 g). The intermediate was immediately treated with methanol (400 ml) to give a solid, which slowly dissolved on stirring at ambient temperature for 18 hours. Evaporation of solvent to a small volume and filtration gave the title product as an off-white solid (14.7 g).

NMR (DMSO-$d_6$) δ: 2.03 (s, 3H); 2.53 (br, 2H); 3.26 (t, 2H); 3.73 (br, 2H); 3.84 (dd, 1H); 4.16 (t, 1H); 4.24 (dd, 1H); 4.30 (dd, 1H); 4.95 (m, 1H); 5.88 (s, 1H); 7.37 (d, 2H); 9.39 (s, 2H); (+1H for $NH_2^+$).

3-(4(1-(2,2-Dimethyl-1,3-dioxolan-4(S)-ylcarbonyl)-1,2,5,6-tetrahydropyrid-4-yl)-3,5-difluorophenyl)-5(R)-acetoxymethyloxazolidin-2-one 3-(4-(1,2,5,6-tetrahydropyridyl)-3,5-difluorophenyl)-5(R)-acetoxymethyloxazolidin-2-one hydrochloride (14.5 g, 37.3 mM) was suspended in dry dichloromethane (300 ml) under nitrogen at 0°, and treated with pyridine (9.78 g, 0.12 M). A solution of 2,2-dimethyl-1,3-dioxolan-4(S)-ylcarbonyl chloride (9.59 g, 75.6 mM) in dichloromethane (100 ml) was added dropwise, and stirring continued for 3 hours, allowing the temperature to rise to ambient. Aqueous sodium bicarbonate (5%, 300 ml) was added, and stirring continued for 30 minutes. The organic phase was separated, dried (magnesium sulfate), filtered, and evaporated to dryness after the addition of toluene (20 ml). The solid residue was triturated with a mixture of diethyl ether (250 ml) and isohexane (150 ml), and solid filtered to give the title compound (17.5 g).

NMR (DMSO-$d_6$) δ: 1.30 (2× s, 6H); 2.02 (s, 3H); 2.28 (br, 1H); 2.39 (br, 1H); 3.67 (t overlapping m, 2H); 3.83 (dd, 1H); 4.00–4.32 (overlapping m, 7H); 4.90 (overlapping m, 2H); 5.86 (s, 1H); 7.34 (d, 2H). MS (ESP): 481 (MH$^+$) for $C_{23}H_{26}F_2N_2O_7$

3-(4-(1-(2,2-Dimethyl-1,3-dioxolan-4(S)-ylcarbonyl)-1,2,5,6-tetrahydropyrid-4-yl)-3,5-difluorophenyl)-5(R)-hydroxymethyloxazolidin-2-one 3-(4-(1-(2,2-Dimethyl-1,3-dioxolan-4(S)-ylcarbonyl)-1,2,5,6-tetrahydropyrid-4-yl)-3,5-difluorophenyl)-5(R)-acetoxymethyloxazolidin-2-one (8.64 g, 18 mM) was suspended in methanol (350 ml) and stirred at ambient temperature under nitrogen. Potassium carbonate (3.73 g, 27 mM) was added, and the mixture stirred for 20 minutes only, then neutralised immediately by the addition of acetic acid (2 ml). Saturated aqueous sodium bicarbonate (50 ml) was added, the methanol evaporated, and the residue diluted with water (100 ml) before extraction of the organics into dichloromethane (250 ml+100 ml). The extract was washed with brine (100 ml), dried (magnesium sulfate), evaporated and crude product purified by chromatography on a 300 g silica vacuum sinter column, eluting with a gradient from 0% to 20% methanol in dichloromethane. Relevant fractions were combined to give the desired product (7.3 g).

NMR (DMSO-$d_6$) δ: 1.29 (s, 3H); 1.32 (s, 3H); 2.29 (br, 1H); 2.38 (br, 1H); 3.48–3.76 (complex m, 4H); 3.82 (dd, 1H); 4.05 (complex m, 4H); 4.21 (dd, 1H); 4.72 (m, 1H); 4.90 (dd, 1H); 5.22 (t, 1H); 5.86 (s, 1H); 7.35 (d, 2H). MS (ESP): 439 (MH$^+$) for $C_{21}H_{24}F_2N_2O_6$

3-(4-(1-(2,2-dimethyl-1,3-dioxolan-4(S)-ylcarbonyl)-1,2,5,6-tetrahydropyrid-4-yl)-3,5-difluorophenyl)-5(R)-methanesulfonyloxymethyloxazolidin-2-one 3-(4-(1-(2,2-Dimethyl-1,3-dioxolan-4(S)-ylcarbonyl)-1,2,5,6-tetrahydropyrid-4-yl)-3,5-difluorophenyl)-5(R)-hydroxymethyloxazolidin-2-one (2.19 g, 5 mM) was dissolved in dry dichloromethane (40 ml) under nitrogen at 0°, and treated with triethylamine (0.81 g, 8 mM). Methanesulfonyl chloride (0.687 g, 6 mM) was added, and stirring continued for 2 hours, allowing the temperature to rise to ambient. Aqueous sodium bicarbonate (5%, 20 ml) was added, and stirring continued for 10 minutes. The organic phase was separated, dried (magnesium sulfate), filtered, and evaporated to dryness. The resulting gum was triturated with diethyl ether (50 ml) and solid filtered to give the title compound (2.4 g).

NMR (DMSO-$d_6$) δ: 1.30 (s, 3H); 1.33 (s, 3H); 2.30 (br, 1H); 2.39 (br, 1H); 3.26 (s, 3H); 3.67 (t overlapping m, 2H); 3.82 (dd, 1H); 4.01–4.31 (complex overlapping m, 5H); 4.45 (dd, 1H); 4.51 (dd, 1H); 4.90 (dd, 1H); 5.03 (m, 1H); 5.87 (s, 1H); 7.35 (d, 2H). MS (ESP): 517 (MH$^+$) for $C_{22}H_{26}F_2N_2O_8S$

3-(4-(1-(2,2-Dimethyl-1,3-dioxolan-4(S)-ylcarbonyl)-1,2,5,6-tetrahydropyrid-4-yl)-3,5-difluorophenyl)-5(R)-(N-(t-butoxycarbonyl)-3-methylisoxazol-5-ylaminomethyl)oxazolidin-2-one Sodium hydride (60% in oil, 72 mg, 1.8 mM) was suspended in dry N,N-dimethylformamide (3 ml), cooled to 0° under nitrogen, and a solution of 5-(t-butoxycarbonylamino)-3-methylisoxazole (356 mg, 1.8 mM) in N,N-dimethylformamide (3 ml) added. After stirring for 10 minutes, a solution of 3-(4(1-(2,2-dimethyl-1,3-dioxolan-4(S)-ylcarbonyl)-1,2,5,6-tetrahydropyrid-4-yl)-3,5-difluorophenyl)-5(R)-methanesulfonyloxymethyloxazolidin-2-one (516 mg, 1.5 mM) in N,N-dimethylformamide (3 ml) was added, and the mixture heated to 40° for 5 hours. After cooling, the mixture was poured into water (50 ml), extracted with dichloromethane (4×20 ml). The organic phase was dried (magnesium sulfate), evaporated and crude product purified by chromatography on a 10 g silica Mega Bond Elut® column, eluting with a gradient from 50% to 75% ethyl acetate in isohexane. Relevant fractions were combined to give the desired product (420 mg).

NMR (DMSO-d$_6$) δ: 1.30 (s, 3H); 1.32 (s, 3H); 1.46 (s, 9H); 2.18 (s, 3H); 2.30 (m, 1H); 2.41 (m, 1H); 3.67 (t, 1H); 3.74 (m, 1H); 3.81 (dd, 1H); 4.00 (overlapping m, 3H); 4.06 (dd, 1H); 4.18 (m, 3H); 4.89 (m, 2H); 5.87 (s, 1H); 6.04 (s, 1H); 7.31 (d, 2H). MS (ESP): 619 (MH$^+$) for C$_{30}$H$_{36}$F$_2$N$_4$O$_8$ 5-(t-Butoxycarbonylamino)-3-methylisoxazole 5-Amino-3-methylisoxazole (4.91 g, 0.05 M) was dissolved in dry dichloromethane (80 ml), and 4-dimethylaminopyridine (100 mg) and di-t-butyl dicarbonate (21.85 g, 0.1 M) added. The mixture was stirred at ambient temperature for 48 hours, then evaporated to dryness. The residue was purified by chromatography on a 90 g Biotage silica column, eluting with a gradient increasing in polarity from 0 to 5% diethyl ether in dichloromethane. Relevant fractions were combined and evaporated to give the desired product (0.67 g).

NMR (DMSO-d$_6$) δ: 1.46 (s, 9H); 2.12 (s, 3H); 5.81 (s, 1H); 10.85 (br, 1H). M (ESP): 199 (MH$^+$) for C$_9$H$_{14}$N$_2$O$_3$

EXAMPLE 21

3-(4-(1-(2(S),3-Dihydroxypropanoyl)-1,2,5,6-tetrahydropyrid-4-yl)-3,5-difluorophenyl)-5(S)-(1,2,4-thiadiazol-5-ylaminomethyl)oxazolidin-2-one Using essentially the conditions of Example 20, but starting from 3-(4-(1-(2,2-dimethyl-1,3-dioxolan-4(S)-ylcarbonyl)-1,2,5,6-tetrahydropyrid-4-yl)-3,5-difluorophenyl)-5(R)-(N-(t-butoxycarbonyl)-1,2,4-thiadiazol-5-ylaminomethyl)oxazolidin-2-one (200 mg, 0.32 mM) gave the title product (91 mg).

NMR (DMSO-d$_6$) δ: 2.31 (m, 1H); 2.37 (m, 1H); 3.47 (m, 1H); 3.55 (m, 1H); 3.71 (m, 4H); 3.79 (dd, 1H); 4.10 (m, 1H); 4.16 (t, 1H); 4.26 (m, 1H); 4.35 (t, 1H); 4.66 (t, 1H); 4.93 (m, 2H); 5.85 (s, 1H); 7.31 (d, 2H); 7.92 (s, 1H); 8.72 (br, 1H). MS (ESP): 482 (MH$^+$) for C$_{20}$H$_{21}$F$_2$N$_5$O$_5$S The intermediates for this compound were prepared as follows:

3-(4-(1-(2,2-Dimethyl-1,3-dioxolan-4(S)-ylcarbonyl-1,2,5,6-tetrahydropyrid-4-yl)-3,5-difluorophenyl)-5(R)-(N-(t-butoxycarbonyl)-1,2,4-thiadiazol-5-ylaminomethyl)oxazolidin-2-one Using essentially the technique of the relevant intermediate for Example 20, but using 5-(t-butoxycarbonylamino)-1,2,4-thiadiazole (330 mg, 1.5 mM) as the amino component, gave the title product (221 mg).

NMR (DMSO-d$_6$) δ: 1.30 (s, 3H); 1.33 (s, 3H); 1.53 (s, 9H); 2.31 (m, 1H); 2.39 (m, 1H); 3.67 (t, 1H); 3.75 (m, 1H); 3.94 (dd, 1H); 4.08 (t overlapping m, 2H); 4.23 (t overlapping m, 3H); 4.30 (dd, 1H); 4.46 (dd, 1H); 4.96 (dd, 1H); 5.07 (m, 1H); 5.87 (s, 1H); 7.33 (d, 2H); 8.43 (s, 1H). MS (ESP): 622 (MH$^+$) for C$_{28}$H$_{33}$F$_2$N$_5$O$_7$S 5-(t-butoxycarbonylamino)-1,2,4-thiadiazole 5-Amino-1,2,4-thiadiazole hydrochloride (1.38 g, 0.01 M) was suspended by stirring in dry dichloromethane (50 ml), triethylamine (1.21 g, 0.012 M) added, and the mixture stirred at ambient temperature for 20 minutes to give a solution. Di-t-butyl dicarbonate (4.8 g, 0.022 M) was added and the mixture tirred at ambient temperature for 18 hours, then evaporated to dryness. The residue was purified by chromatography on a 20 g silica Mega Bond Elut® column, eluting with a gradient from 0% to 10% diethyl ether in dichloromethane. Relevant fractions were combined to give the desired product (1.05 g). NMR (DMSO-d$_6$) δ: 1.50 (s, 9H); 8.33 (s, 1H); 12.31 (br, 1H). MS (ESP): 202 (MH$^+$) for C$_7$H$_{11}$N$_3$O$_2$S

EXAMPLE 22

3-(4-(1-(2(S),3-Dihydroxypropanoyl)-1,2,5,6-tetrahydropyrid-4-yl)-3,5-difluorophenyl)-5(S)-pyrazin-2-ylaminomethyloxazolidin-2-one 3-(4-(1-(2,2-Dimethyl-1,3-dioxolan-4(S)-ylcarbonyl)-1,2,5,6-tetrahydropyrid-4-yl)-3,5-difluorophenyl)-5(R)-(N-(t-butoxycarbonyl)pyrazin-2-ylaminomethyl)oxazolidin-2-one (400 mg, 0.65 mM) was dissolved in dichloromethane (4 ml) and treated with trifluoroacetic acid (4 ml) at ambient temperature. After stirring for 30 minutes at ambient temperature, water (0.8 ml) was added, and stirring continued for 2 hours. Solvent was removed, the residue dissolved in methanol (20 ml), and treated with aqueous ammonia to bring the pH to 8; solvent was removed, and the residue chromatographed on a 10 g silica Mega Bond Elut® column, eluting with a gradient increasing in polarity from 5 to 10% methanol in dichloromethane. Relevant fractions were combined and evaporated to give the desired product (315 mg).

NMR (DMSO-d$_6$) δ: 2.28 (br, 1H); 2.37 (br, 1H); 3.46 (m, 1H); 3.54 (m, 1H); 3.64 (t, 2H); 3.71 (m, 1H); 3.81 (dd, 1H); 4.10 (overlapping m, 4H); 4.36 (m, 1H); 4.71 (t, 1H); 4.89 (m, 1H); 5.01 (t, 1H); 5.85 (s, 1H); 7.32 (d, 2H); 7.43 (t, 1H); 7.70 (d, 1H); 7.94 (d, 1H); 7.99 (s, 1H). MS (ESP): 476 (MH$^+$) for C$_{22}$H$_{23}$F$_2$N$_5$O$_5$ The intermediates for this compound were prepared as follows:

3-(4-(1-(2,2-Dimethyl-1,3-dioxolan-4(S)-ylcarbonyl)-1,2,5,6-tetrahydropyrid-4-yl)-3,5-difluorophenyl)-5(R)-methansulfonyloxymethyloxazolidin-2-ylaminomethyl)oxazolidin-2-one Sodium hydride (50% in oil, 72 mg, 1.5 mM) was suspended in dry N,N-dimethylformamide (3 ml) under nitrogen, and a solution of t-butoxycarbonylaminopyrazine (293 mg, 1.5 mM) in N,N-dimethylformamide (3 ml) added. After stirring for 10 minutes, a solution of 3-(4-(1-(2,2-dimethyl-1,3-dioxolan-4(S)-ylcarbonyl)-1,2,5,6-tetrahydropyrid-4-yl)-3,5-difluorophenyl)-5(R)-methanesulfonyloxymethyloxazolidin-2-one (516 mg, 1.5 mM, Example 20) in N,N-dimethylformamide (3 ml) was added, and the mixture heated to 40° for 2.5 hours. After cooling, the mixture was diluted with aqueous sodium bicarbonate (5%, 30 ml), extracted with ethyl acetate (2×30 ml). The organic phase was washed with water (10 ml) and brine (10 ml), dried (magnesium sulfate), evaporated and crude product purified by chromatography on a 10 g silica Mega Bond Elut® column, eluting with a gradient from 0% to 60% ethyl acetate in dichloromethane. Relevant fractions were combined to give the desired product (450 mg).

NMR (DMSO-d$_6$) δ: 1.30 (s, 3H); 1.33 (s, 3H); 1.45 (s, 9H); 2.28 (br, 1H); 2.39 (br, 1H); 3.67 (t, 1H); 3.75 (m, 1H); 3.87 (dd, 1H); 4.02–4.25 (overlapping m, 6H); 4.32 (dd, 1H); 4.90 (dd, 1H); 5.01 (m, 1H); 5.87 (s, 1H); 7.33 (d, 2H);

8.37 (d, 1H); 8.44 (d, 1H); 8.91 (s, 1H). MS (ESP): 616 (MH$^+$) for $C_{30}H_{35}F_2N_5O_7$ t-Butoxycarbonylaminopyrazine Aminopyrazine (3 g, 31.6 mM) was dissolved in dry dichloromethane (100 ml), and 4-dimethylaminopyridine (200 mg) and di-t-butyl dicarbonate (14 g, 64.2 mM) added. The mixture was stirred at ambient temperature for 18 hours, then evaporated to dryness. The residue was purified by chromatography on a 50 g Isolute silica column, eluting with dichloromethane. Relevant fractions were combined and evaporated to give di-(t-butoxycarbonyl)aminopyrazine (2.4 g). NMR (DMSO-d$_6$) δ: 1.36 (s, 18H); 8.55 (d, 1H); 8.58 (d, 1H); 8.73 (s, 1H). MS (ESP): 296 (MH$^+$) for $C_{14}H_{21}N_3O_4$ Di-(t-butoxycarbonyl)aminopyrazine (2.1 g, 7.1 mM) in methanol (50 ml) under nitrogen, was treated with aqueous sodium hydroxide (2.5 M, 2.84 ml, 7.1 mM), and stirred at ambient temperature for 2 hours. The mixture was neutralised by the addition of water (25 ml) and solid carbon dioxide, then methanol evaporated. The residual aqueous solution was extracted with dichloromethane (2×20 ml), the extracts washed with brine (20 ml) and evaporated. The resulting solid was triturated with isohexane (50 ml) to give the title product as a white solid (1.03 g).

NMR (DMSO-d$_6$) δ: 1.47 (s, 9H); 8.25 (d, 1H); 8.30 (d, 1H); 9.03 (s, 1H); 10.14 (s, 1H). MS (ESP): 196 (MH$^+$) for $C_9H_{13}N_3O_2$

EXAMPLE 23

3-(4-(1-(2(S),3-Dihydroxpropanoyl)-1,2,5,6-tetrahydropyrid-4-yl)-3,5-difluorophenyl)-5(S)pyrimidin-2-ylaminomethyloxazolidin-2-one Using essentially the technique of Example 22, but starting from 3-(4-(1-(2,2-dimethyl-1,3-dioxolan-4(S)-ylcarbonyl)-1,2,5,6-tetrahydropyrid-4-yl)-3,5-difluorophenyl)-5(R)-(N-(t-butoxycarbonyl)pyrimidin-2-ylaminomethyl)oxazolidin-2-one (400 mg, 0.65 mM), gave the title product (284 mg) after chromatography.

NMR (DMSO-d$_6$) δ: 2.29 (br, 1H); 2.38 (br, 1H); 3.47 (m, 1H); 3.54 (m, 1H); 3.61 (m, 3H); 3.72 (m, 1H); 3.85 (dd, 1H); 4.13 (t overlapping m, 3H); 4.36 (m, 1H); 4.70 (t, 1H); 4.88 (m, 1H); 4.99 (t, 1H); 5.85 (s, 1H); 6.61 (t, 1H); 7.32 (d, 2H); 7.44 (t, 1H); 8.28 (d, 2H). MS (ESP): 476 (MH$^+$) for $C_{22}H_{23}F_2N_5O_5$ The intermediates for this compound were prepared as follows:

3-(4-(1-(2,2-Dimethyl-1,3-dioxolan-4(S)-ylcarbonyl)-1,2,5,6-tetrahydropyrid-4-yl)-3,5-difluorolphenyl)-5(R)-(N-(t-butoxycarbonyl)pyrimidin-2-ylaminomethyl)oxazolidin-2-one Essentially the technique for the appropriate intermediate of Example 22 was used, but substituting 2-(t-butoxycarbonylamino)pyrimidine (293 mg, 1.5 mM) for the pyrazine analogue. To complete the reaction, heating at 80° for 1 hour was necessary, and the chromatography was carried out with a gradient from 0% to 50% ethyl acetate in dichloromethane containing 2% triethylamine. Relevant fractions were combined to give the desired product (427 mg).

NMR (DMSO-d$_6$) δ: 1.32 (s, 3H); 1.34 (s, 3H); 1.41 (s, 9H); 2.30 (br, 1H); 2.38 (br, 1H); 3.67 (t, 1H); 3.75 (m, 1H); 3.87 (dd, 1H); 4.00–4.33 (overlapping m, 7H); 4.90 (dd, 1H); 5.01 (m, 1H); 5.87 (s, 1H); 7.27 (t, 1H); 7.31 (d, 2H); 8.73 (d, 2H).

MS (ESP): 616 (MH$^+$) for $C_{30}H_{35}F_2N_5O_7$ 2-(t-Butoxycarbonylamino)pyrimidine Essentially the technique for the appropriate intermediate of Example 22 was used, but substituting 2-aminopyrimidine (3 g, 31.6 mM) for aminopyrazine. The reaction was stirred for 72 hours and the chromatography used a gradient from 0 to 10% diethyl ether in dichloro-methane; the product was finally triturated with isohexane (10 ml) to give 2-di-(t-butoxycarbonyl)amino)pyrimidine (5.7 g). NMR (DMSO-d$_6$) δ: 1.37 (s, 18H); 7.48 (t, 1H); 8.66 (d, 2H). MS (ESP): 296 (MH$^+$) for $C_{14}H_{21}N_3O_4$ 2-(Di-(t-butoxycarbonyl)amino)pyrimidine (5.2 g, 17.6 mM) was hydrolysed by essentially the technique for the appropriate intermediate of Example 22 to give the title product as a white solid (3.2 g). NMR (DMSO-d$_6$) δ: 1.43 (s, 9H); 7.08 (t, 1H); 8.57 (d, 2H); 9.91 (s, 1H). MS (ESP): 196 (MH$^+$) for $C_9H_{13}N_3O_2$

EXAMPLE 24

3-(4-(1-(2(S),3-Dihydroxypropanoyl)-1,2,5,6-tetrahydropyrid-4-yl)-3,5-difluorophenyl)-5(S)-pyridazin-3-ylaminomethyloxazolidin-2-one Using essentially the technique of Example 22, but starting from 3-(4-(1-(2,2-dimethyl-1,3-dioxolan-4(S)-ylcarbonyl)-1,2,5,6-tetrahydropyrid-4-yl)-3,5-difluorophenyl)-5(R)-(N-(t-butoxycarbonyl)pyridazin-3-ylaminomethyl)oxazolidin-2-one (300 mg, 0.49 mM), gave the title product (217 mg) after chromatography.

NMR (DMSO-d$_6$) δ: 2.29 (br, 1H); 2.39 (br, 1H); 3.47 (m, 1H); 3.55 (m, 1H); 3.74 (t overlapping m, 4H); 3.83 (dd, 1H); 4.16 (t overlapping m, 3H); 4.35 (m, 1H); 4.66 (m, 10H); 4.94 (m, 2H); 5.85 (s, 1H); 6.85 (d, 1H); 7.15 (t, 1H); 7.22 (dd, 1H); 7.30 (d, 2H); 8.44 (d, 1H). MS (ESP): 476 (MH$^+$) for $C_{22}H_{23}F_2N_5O_5$ The intermediates for this compound were prepared as follows:

3-(4-(1-(2,2-Dimethyl-1,3-dioxolan-4(S)-ylcarbonyl)-1,2,5,6-tetrahydropyrid-4-yl)-3,5-difluorophenyl-5(R)-(N-(t-butoxycarbonyl)pyridazin-3-ylaminomethyl)oxazolidin-2-one Essentially the technique for the appropriate intermediate of Example 22 was used, but substituting 3-(t-butoxycarbonylamino)pyridazine (293 mg, 1.5 mM) for the pyrazine analogue. The reaction was carried out by heating at 45° for 4 hour, and the chromatography was carried out with a gradient from 0% to 100% ethyl acetate in dichloromethane. Relevant fractions were combined to give the desired product (315 mg).

NMR (DMSO-d$_6$) δ: 1.17 (s, 3H); 1.20 (s, 3H); 1.33 (s, 9H); 2.16 (br, 1H); 2.25 (br, 1H); 3.55 (t, 1H); 3.62 (t, 1H); 3.76 (dd, 1H); 3.84–4.17 (overlapping m, 6H); 4.30 (dd, 1H); 4.77 (dd, 1H); 4.96 (m, 1H); 5.84 (s, 1H); 7.19 (d, 2H); 7.55 (dd, 1H); 7.78 (d, 1H); 8.89 (d, 1H). MS (ESP): 616 (MH$^+$) for $C_{30}H_{35}F_2N_5O_7$ 3-(t-Butoxycarbonylamino)pyridazine Essentially the technique for the appropriate intermediate of Example 22 was used, but substituting 3-aminopyridazine (1.3 g, 13.6 mM) for aminopyrazine. The reaction was stirred for 18 hours and the chromatography used a gradient from 0 to 20% diethyl ether in dichloro-methane to give 3-(di-(t-butoxycarbonyl)amino)pyridazine (1.2 g).

NMR (DMSO-d$_6$) δ: 1.37 (s, 18H); 7.82 (d, 2H); 9.18 (t, 1H). MS (ESP): 296 (MH$^+$) for C$_{14}$H$_{21}$N$_3$O$_4$ 2-(Di-(t-butoxycarbonyl)amino)pyrimidine (5.2 g, 17.6 MM) was hydrolysed by essentially the technique for the appropriate intermediate of Example 22 to give the title product as a white solid (690 mg). NMR (DMSO-d$_6$) δ: 1.47 (s, 9H); 7.60 (dd, 1H); 8.04 (d, 1H); 8.87 (d, 1H); 10.41 (s, 1H). MS (ESP): 196 (MH$^+$) for C$_9$H$_{13}$N$_3$O$_2$

EXAMPLE 25

3-(4-(1-Acetoxyacetyl-1,2,5,6-tetrahydropyrid-4-yl)-3,5-difluorophenyl)-5(S)-(1,2,5-thiadiazol-3-ylaminomethyl)oxazolidin-2-one Trifluoroacetic acid (5 ml) was added dropwise to a stirred solution of 3-(4-(1-acetoxyacetyl-1,2,5,6-tetrahydropyrid-4-yl)-3,5-difluorophenyl)-5(R)-(N-(t-butoxycarbonyl)-1,2,5-thiadiazol-3-ylaminomethyl)oxazolidin-2-one (426 mg, 0.718 mM) in dichloromethane (10 ml) and the mixture kept for one hour. The solution was washed with water, saturated sodium bicarbonate solution and brine and dried (sodium sulfate). Solvent was evaporated and the residue purified on a silica Mega Bond Elut® column, eluting with dichloromethane, and then 1.5% methanol/dichloromethane to give an oil which solidified on trituration with cold diethyl ether to give the title product (254 mg, 72%)

NMR (DMSO-d$_6$) δ: 2.08 (s, 3H); 2.31 (m, 1H); 2.40 (m, 1H); 3.53 (t, 1H); 3.63 (m, 3H); 3.82 (dd, 1H); 4.07 (m, 2H); 4.17 (t, 1H); 4.82 (d, 2H); 4.95 (m, 1H); 5.85 (m, 1H); 7.32 (d, 2H); 7.71 (t, 1H); 8.41 (s, 1H). MS (ESP): 495 (MH$^+$) for C$_{21}$H$_{21}$F$_2$N$_5$O$_5$S The intermediates for this compound were prepared as follows:

3-(4-(1-Benzyl-1,2,5,6-tetrahydropyrid-4-yl3,5-difluorophenyl)-5(R)-(N-(t-butoxycarbonyl) 1,2,5-thiadiazol-3-ylaminomethyl)oxazolidin-2-one 1,1'-(Azodicarbonyl)dipiperidine (680 mg, 2.7 mM) was added portionwise to a stirred solution of 3-t-butyloxycarbonylamino-1,2,5-thiadazole (543 mg, 2.7 mM, see WO 93-13091), 3-(4-(1-benzyl-1,2,5,6-tetrahydropyrid-4-yl)-3,5 difluorophenyl)-5(R)-hydroxy-methyloxazolidin-2-one (720 mg, 1.8 mM; prepared by analogy with 3-fluoro compound—see WO 97-30995) and tributylphosphine (540 mg, 2.7 mM) in dry tetrahydrofuran (25 ml) at 0° under nitrogen. The mixture was stirred at 0° for 30 minutes and then at ambient temperature for 3 hours. The mixture was filtered and the filtrate evaporated. The residue was purified, firstly on a silica Mega Bond Elut® column, eluting with a gradient increasing in polarity from 0 to 30% ethyl acetate in isohexane and then on an Isolute SCX ion exchange column, washing with a gradient increasing in polarity from 0 to 10% methanol in dichloromethane and then eluting with dichloromethane/methanol/0.88SG ammonia 87:10:3 to give the title product as a solid (669 mg, 64%).

NMR (DMSO-d$_6$) δ: 1.49 (s, 9H); 2.30 (brs, 2H); 2.61 (t, 2H); 3.04 (m, 2H); 3.58 (s, 2H); 3.88 (dd, 1H); 4.13 (dd, 1H); 4.20 (dd, 1H); 4.35 (dd, 1H); 5.02 (m, 1H); 5.79 (brs, 1H); 7.20–7.33 (m, 7H); 8.96 (s, 1H). MS (ESP): 584 (MH$^+$) for C$_{29}$H$_{31}$F$_2$N$_5$O$_4$S 3-(4-(1,2,5,6-Tetrahydropyrid-4-yl)-3,5-difluorophenyl)-5(R)-(N-(t-butoxycarbonyl)-1,2,5-thiadiazol-3-ylaminomethyl)oxazolidin-2-one Hydrochloride Using the method described for the appropriate intermediate of Example 20, apart from routine changes in the eluant used for chromatography, hydrolysing the intermediate carbamate by refluxing 1 hour in methanol, and starting from 3-(4-(1-benzyl-1,2,5,6-tetrahydropyrid-4-yl)-3,5-difluorophenyl)-5(R)-(N-(t-butoxycarbonyl)-1,2,5-thiadiazol-3-ylaminomethyl)oxazolidin-2-one (650 mg, 1.11 mM), gave the title compound (493 mg, 84%).

NMR (DMSO-d$_6$) δ: 1.54 (s, 9H); 2.52 (m overlapped by DMSO, 2H); 3.28 (m overlapped by H$_2$O, 2H); 3.76 (s, 2H); 3.91 (dd, 1H); 4.12–4.25 (m, 2H); 4.40 (dd, 1H); 5.09 (m, 1H); 5.91 (s, 1H); 7.40 (d, 2H); 9.00 (s, 1H); 9.25 (brs, 2H); (+1H for HCl salt). MS (ESP): 494 (MH$^+$) for C$_{22}$H$_{25}$F$_2$N$_5$O$_4$S 3-(4-(1-Acetoxyacetyl-1,2,5,6-tetrahydropyrid-4-yl)-3,5-difluourophenyl)-5(R)-(N-(t-butoxy-carbonyl)-1,2,5,6-thiadiazol-3-ylaminomethyl)oxazolidin-2-one 3-(4-(1,2,5,6-Tetrahydropyrid 4-yl)-3,5-difluorophenyl)$_5$(R)-(N-(t-butoxycarbonyl)-1,2,5-thiadiazol-3-ylaminomethyl)oxazolidin-2-one hydrochloride (485 mg, 0.916 mM) was suspended in a mixture of acetone (10 ml) and water (5 ml), and sodium bicarbonate (770 mg, 9.2 mM) added. The mixture was cooled in an ice-bath and treated dropwise with acetoxy-acetyl chloride (495 mg, 3.63 mM), and then stirred for 7 hours, allowing the temperature to rise to ambient. Further portions of sodium bicarbonate (770 mg) and acetoxyacetyl chloride (495 mg) were added, and stirring continued for 18 hours. The mixture was diluted with water (20 ml) and extracted with ethyl acetate (3×25 ml), and the combined organics washed with water (2×15 ml), aqueous hydrochloric acid (1M, 15 ml), brine (15 ml) and dried (sodium sulfate) to give the desired product (434 mg, 80%).

NMR (400 MHz. DMSO-d$_6$) δ: 1.50 (s, 9H); 2.10 (s, 3H); 2.31 (m, 1H); 2.42 (m, 1H); 3.57 (t, 1H); 3.66 (t, 1H); 3.90 (dd, 1H); 4.04–4.22 (m, 4H); 4.39 (dd, 1H); 4.85 (d, 2H); 5.08 (m, 1H); 5.88 (s, 1H); 7.35 (d, 2H); 9.00 (s, 1H). MS (ESP): 594 (MH$^+$) for C$_{26}$H$_{29}$F$_2$N$_5$O$_7$S

EXAMPLE 26

3-(4-(1-Hydroxyacetyl-1,2,5,6-tetrahydropyrid-4-yl)-3,5-difluorophenyl)-5(S)-(1,2,5-thiadiazol-3-ylaminomethyl)oxazolidin-2-one A saturated solution of ammonia in methanol (7 ml) was added to a suspension of 3(4-(1-acetoxyacetyl-1,2,5,6-tetrahydropyrid-4-yl)-3,5-difluorophenyl)-5(S)-(1,2,5-thiadiazol-3-ylaminomethyl)oxazolidin-2-one (228 mg, 0.462 mM, Example 25) in methanol (7 ml) and the mixture was stirred for 20 hours. A small amount of insoluble material was filtered off and the filtrate evaporated to a small volume and cooled. The precipitate was filtered and washed with cold methanol and diethyl ether to give the title product (150 mg, 72%). NMR (400 MHz. DMSO-d$_6$) δ: 2.23 (m, 1H); 2.30 (m, 1H); 3.46 (t, 1H); 3.62 (m, 3H); 3.79 (dd, 1H); 3.97–4.12 (m, 5H); 4.52 (dt, 1H); 4.90 (m, 1H); 5.80 (m, 1H); 7.32 (d, 2H); 7.63 (t, 1H); 7.97 (s, 1H). MS (ESP): 452 (MH$^+$) for C$_{19}$H$_{19}$F$_2$N$_5$O$_4$S

EXAMPLE 27

3-(4-(1-(2(S),3-Dihydroxypropanoyl)-1,2,5,6-tetrahydropyrid-4-yl)-3-fluorophenyl)-5(S)-(1,2,5-thiadiazol-3-ylaminomethyl)oxazolidin-2-one A solution of 3-(4(1-(2,2-dimethyl-1,3-dioxolan-4(S)-ylcarbonyl)-1,2,5,6-tetrahydropyrid-4-yl)-3-fluorophenyl)-5(R)-(N-(t-butoxycarbonyl)-1,2,5-thiadiazol-3-ylamino-methyl)oxazolidin-2-one (580 mg, 0.96 mM) in trifluoroacetic acid (2 ml) was warmed at 60° for 2 minutes and then kept at ambient temperature for 10 minutes. A solution of trifluoroacetic acid in water (10 ml, 1:1) was added and the mixture kept for 30 minutes. More trifluoroacetic acid (2 ml) was added and after a further 90 minutes, excess aqueous ammonia was added and the mixture extracted three times with ethyl acetate. The combined extracts were washed with water, sodium bicarbonate solution and brine and dried (sodium sulfate). Solvent was evaporated and the residue purified on a silica Mega Bond Elut® column, eluting with dichloromethane and then 4% methanol in dichloromethane to give an oil which solidified on trituration with diethyl ether to give the title product (203 mg, 46%).

NMR (400 MHz. DMSO-$d_6$/CD$_3$COOD) δ: 2.41 (m overlapping DMSO, 2H); 3.45 (m, 1H); 3.54 (m, 1H); 3.48 (overlapping m, 4H); 3.82 (dd, 1H); 4.08–4.25 (m, 3H); 4.39 (m, 1H); 4.92 (m, 1H); 6.01 (s, 1H); 7.27 (dd, 1H); 7.32 (t, 1H); 7.45 (dd, 1H); 8.01 (s, 1H); 2× OH, 1× NH missing, exchanged. MS (ESP): 464 (MH$^+$) for $C_{20}H_{22}FN_5O_5S$ The intermediate was prepared as follows:

Using the methods of the sequence described for the intermediates for Example 25 but staring from 3-(4-(1-benzyl-1,2,5,6-tetrahydropyrid-4-yl)-3-fluorophenyl)-5(R)-hydroxymethyl-oxazolidin-2-one (1.5 g, 3.93 mM, see WO 97-30995) gave the title product (1.77 g, 80%).

NMR (DMSO-$d_6$) δ: 1.50 (s, 9H); 2.42 (brs, 2H); 2.61 (t, 2H); 3.05 (m, 2H); 3.56 (s, 2H); 3.87 (dd, 1H); 4.14 (dd, 1H); 4.21 (dd, 1H); 4.36 (dd, 1H); 5.02 (m, 1H); 5.95 (s, 1H); 7.21–7.46 (overlapping m, 8H); 8.95 (s, 1H). MS (ESP): 566 (MH$^+$) for $C_{29}H_{32}FN_5O_4S$

3-(4-(1,2,5,6-Tetrahydropyrid-4-yl)-3-fluorophenyl)-5(R)-(N-(t-butoxycarbonyl)-1,2,5-thiadiazol-3-ylaminomethyl)oxazolidin-2-one Hydrochloride Using the methods of the sequence described for the intermediates for Example 25 but starting from 3-(4-(1-benzyl-1,2,5,6-tetrahydropyrid-4-yl)-3-fluorophenyl)-5(R)-(N-(t-butoxy-carbonyl)-1,2,5-thiadiazol-3-ylaminomethyl)oxazolidin-2-one (1.72 g, 3.04 mM) gave the title product (1.1 g, 71%).

NMR (DMSO-$d_6$) δ: 1.51 (s, 9H); 2.64 (m, 2H); 3.28 (m overlapped by H$_2$O, 2H); 3.75 (s, 2H); 3.91 (dd, 1H); 4.23 (overlapping m, 2H); 4.39 (dd, 1H); 5.06 (m, 1H); 6.04 (s, 1H); 7.36 (dd, 1H); 7.45 (t, 1H); 7.51 (dd, 1H); 9.00 (s, 1H); 9.22 (brs, 2H); (+1H for HCl salt). MS (ESP): 476 (MH$^+$) for $C_{22}H_2FN_5O_4S$

3-(4(1-(2,2-Dimethyl-1,3-dioxolan-4(S)-ylcarbonyl)-1,2,5,6-tetrahydropyrid-4-yl)-3-fluorophenyl)-5(R)—N-(t-butoxycarbonyl)-1,2,5-thiadiazol-3-yl aminomethyl)oxazolidin-2-one Using the method described for the appropriate intermediate of Example 17, apart from routine changes in the eluant used for chromatography, and starting from 3-(4-(1,2,5,6-tetrahydropyrid 4-yl)-3-fluorophenyl)-5(R)-(N-(t-butoxycarbonyl) 1,2,5-thiadiazol-3-ylaminomethyl)oxazolidin-2-one hydrochloride (512 mg, 1 mM), gave the title product (597 mg, 99%).

NMR (400 MHz, DMSO-$d_6$) δ: 1.35 (6H, s); 1.50 (s, 9H); 3.59–3.80 (m, 2H); 3.90 (m, 2H); 4.05–4.22 (m, 7H); 4.40 (dd, 1H); 4.91 (m, 1H); 5.06 (m, 1H); 6.00 (s, 1H); 7.33 (dd, 1H); 7.40 (t, 1H); 7.48 (dd, 1H); 9.00 (s, 1H). MS (ESP): 604 (MH$^+$) for $C_{28}H_{34}FN_5O_7S$

EXAMPLE 28

3(4-(1-Acetoxyacetyl-1,2,5,6-tetrahydropyridyl)-3-fluorophenyl)-5(S)-(1,2,5-thiadiazol-3-ylaminomethyl)oxazolidin-2-one Trifluoroacetic acid (2 ml) was added to a solution of 3-(4-(1-acetoxyacetyl-1,2,5,6-tetrahydropyrid-4-yl)-3-fluorophenyl)-5(R)-(N-(t-butoxycarbonyl)-1,2,5-thiadiazol-3-ylaminomethyl)oxazolidin-2-one (467 mg, 0.812 mM) in dichloromethane (10 ml) and the solution kept for one hour. Solvent was evaporated and the residue redissolved in dichloromethane. The solution was washed with water, sodium bicarbonate solution and brine and dried (sodium sulfate). Solvent was evaporated and the residue purified on a silica Mega Bond Elut® column, eluting with dichloromethane and then 1.5% methanol in dichloromethane to give an oil which solidified on trituration with diethyl ether to give the title product (227 mg, 59%).

NMR (400 MHz. DMSO-$d_6$) δ: 2.14 (s, 3H); 2.51 (m overlapping DMSO, 2H); 3.64 (m, 1H); 3.72 (m, 3H); 3.90 (t, 1H); 4.13 (m, 2H); 4.22 (t, 1H); 4.89 (m, 2H); 5.00 (m, 1H); 6.10 (brs, 1H); 7.37 (m, 1H); 7.43 (m, 1H); 7.58 (dd, 1H); 7.79 (t, 1H); 8.10 (s, 1H). MS (ESP): 476 (MH$^+$) for $C_{21}H_{22}FN_3O_5S$ The 3-(4-(1-Acetoxyacetyl-1,2,5,6-tetrahydropyrid-4-yl)-3-fluorophenyl)-5(R)-(N-(t-butoxy-carbonyl)-1,2,5-thiadiazol-3-ylaminomethyl)oxazolidin-2-one intermediate was prepared as follows:

Using the method described for the appropriate intermediate of Example 25, but starting from 3-(4-(1,2,5,6-tetrahydropyrid-4-yl)-3-fluorophenyl)$_5$(R)-(N-(t-butoxycarbonyl)-1,2,5-thiadiazol-3-ylaminomethyl)oxazolidin-2-one hydrochloride (512 mg, 1 mM, see Example 27), gave the title product (472 mg, 82%).

NMR (400 MHz, DMSO-$d_6$) δ: 1.38 (s, 9H); 1.97 (s, 3H); 2.39 (brs, 2H); 3.45 (t, 1H); 3.53 (m, 1H); 3.92–4.14 (m, 6H); 4.26 (dd, 1H); 4.71 (d, 2H); 4.92 (m, 1H); 5.88 (brs, 1H); 7.20 (dd, 1H); 7.28 (m, 1H); 7.38 (dd, 1H); 8.85 (s, 1H). MS (ESP): 577 (MH$^+$) for $C_{26}H_{31}FN_5O_7S$

EXAMPLE 29

3-(4-(1-Hydroxyacetyl-1,2,5,6-tetrahydropyrid-4-yl)-3-fluorophenyl)-5(S) (1,2,5-thiadiazol-3-ylaminomethyl)oxazolidin-2-one Using the method described in Example 26 but starting from 3-(4-(1-acetoxyacetyl-1,2,5,6-tetrahydropyrid-4-yl)-3-fluorophenyl)-5(S)-(1,2,5-thiadiazol-3-ylaminomethyl)oxazolidin-2-one (199 mg, 0.42 mM, see Example 28), gave the title product (112 mg, 62%).

NMR (400 MHz. DMSO-$d_6$) δ: 2.58 (m overlapping DMSO, 2H); 3.60 (t, 1H); 3.75 (m, 3H); 3.91 (dd, 1H); 4.10–4.28 (overlapping m, 5H); 4.61 (dt, 1H); 4.96 (m, 1H); 6.09 (m, 1H); 7.36 (dd, 1H); 7.45 (t, 1H); 7.56 (dd, 1H); 7.79 (t, 1H); 8.10 (s, 1H). MS (ESP): 434 (MH$^+$) for $C_{19}H_{20}FN_5O_4S$

EXAMPLE 30

3-[(4-(1-(Z(S),3-Dihydroxypropanoyl)-1,2,5,6-tetrahydropyrid-4-yl-3,5-difluorophenyl)-5(S)(1,2,5-thiadiazol-3-ylaminomethyl)oxazolidin-2-one Using the method described in Example 27, apart from routine changes in the eluant used for chromatography, and starting from 3-(4-(1-(2,2-dimethyl-1,3-dioxolan-4(S)-ylcarbonyl)-1,2,5,6-tetrahydropyrid-4-yl)-3,5-difluorophenyl)-5(R)-(N-(t-butoxycarbonyl)-1,2,5-thia-diazol-3-ylaminomethyl)oxazolidin-2-one (650 mg, 1.05 mM), gave the title compound (265 mg, 53%).

NMR (DMSO-$d_6$) δ: 2.29 (m, 1H); 2.38 (m, 1H); 3.47 (m, 1H); 3.55 (dd, 1H); 3.64 (t overlapping m, 4H); 3.81 (dd, 1H); 4.07 (m, 1H); 4.16 (t, 1H); 4.24 (m, 1H); 4.36 (m, 1H); 4.68 (br, 1H); 4.92 (m, 2H); 5.85 (s, 1H); 7.30 (d, 2H); 7.70 (t, 1H); 8.03 (s, 1H). MS (ESP): 482 (MH$^+$) for $C_{20}H_{21}F_2N_5O_5S$ The 3-(4-(1-(2,2-Dimethyl-1,3-dioxolan-4(S)-ylcarbonyl)-1,2,5,6-tetrahydropyrid-4-yl)-3,5-difluorophenyl)-5(R)-(N-(t-butoxycarbonyl)-1,2,5-thiadiazol-3-ylaminomethyl)oxazolidin-2 one intermediate was prepared as follows:

Using the method described for the appropriate intermediate of Example 17, apart from routine changes in the eluant used for chromatography, and starting from 3-(4-(1,2,5,6-tetrahydropyrid-4-yl)-3,5-difluorophenyl)-5(R)-(N-(t-butoxycarbonyl)-1,2,5-thiadiazol-3-ylaminomethyl)oxazolidin-2-one hydrochloride (800 mg, 1.51 mM, see Example 25), gave the title product (669 mg, 71%).

NMR (DMSO-$d_6$) δ: 1.29 (s, 3H); 1.32 (s, 3H); 1.52 (s, 9H); 2.30 (m, 1H); 2.40 (m, 1H); 3.68 (m, 2H); 3.90 (dd, 1H); 4.04–4.28 (m, 4H); 4.37 (m, 1H); 4.90 (m, 1H); 5.06 (m, 1H); 5.72 (m, 2H); 5.88 (m, 1H); 7.31 (d, 2H); 8.96 (s, 1H). MS (ESP): 622 (MH$^+$) for $C_{28}H_{33}F_2N_5O_7S$

EXAMPLE 31

3-(4-(1-(2(S),3-Dihydroxypropanoyl)-1,2,5,6-tetrahydropyridyl)-4-yl)-3,5-difluorophenyl)-5(S)-(1,3,4-thiadiazol-2-ylaminomethyl)oxazolidin-2-one Using the method described in Example 27, apart from routine changes in the eluant used for chromatography, and starting from 3-(4-(1-(2,2-dimethyl-1,3-dioxolan-4(S)-ylcarbonyl)-1,2,5,6-tetrahydropyrid-4-yl)-3,5-difluorophenyl)-5(R)-(N-(t-butoxycarbonyl)-1,3,4-thia-diazol-2-ylaminomethyl)oxazolidin-2-one (190 mg, 0.30 mM), gave the title compound (75 mg, 51%).

NMR (400 MHz. DMSO-$d_6$) δ: 2.33 (m, 1H); 2.41 (m, 1H); 3.48 (m, 1H); 3.55 (m, 1H); 3.72 (overlapping m, 4H); 3.83 (dd, 1H); 4.12 (m, 1H); 4.09 (t, 1H); 4.27 (m, 1H); 4.37 (m, 1H); 4.69 (m, 1H); 4.97 (m, 2H); 5.87 (s, 1H); 7.34 (d, 2H); 8.11 (t, 1H); 8.67 (s, 1H). MS (ESP): 482 (MH$^+$) for $C_{20}H_{21}F_2N_5O_5S$ The intermediates for this compound were prepared as follows:

3-(4-(1-Benzyl-1,2,5,6-tetrahydropyridyl-4-yl)-3,5-difluorophenyl)-5(R)-(N-(t-butoxycarbonyl-1,3,4-thiadiazol-2-ylaminomethyl)oxazolidin-2-one Using the method described for the appropriate intermediate of Example 25, apart from routine changes in the eluant used for chromatography, and starting from 3-(4-(1-benzyl-1,2,5,6-tetrahydropyrid-4-yl)-3,5-difluorophenyl)-5 (R)-hydroxymethyloxazolidin-2-one (3 g, 7.5 mM) and 2-t-butyloxycarbonylamino-1,3,4-thiadazole (1.96 g, 9.75 mM) gave the title compound (1.58 g, 36%).

NMR (DMSO-$d_6$) δ: 1.50 (s, 9H); 2.31 (brs, 2H); 2.61 (t, 2H); 3.04 (m, 2H); 3.58 (s, 2H); 3.91 (dd, 1H); 4.22 (t, 1H); 4.32 (dd, 1H); 4.49 (dd, 1H); 5.09 (m, 1H); 5.79 (brs, 1H); 7.23–7.37 (overlapping m, 7H); 9.23 (s, 1H). MS (ESP): 584 (MH$^+$) for $C_{29}H_{31}F_2N_5O_4S$

2-t-Butyloxycarbonylamino-1,3,4-thiadazole

2-Amino-1,3,4-thiadiazole (5 g, 49.4 mM) was dissolved in dry pyridine (100 ml), and 4-dimethylaminopyridine (100 mg) and di-t-butyl dicarbonate (21.6 g, 98.9 mM) added. The mixture was stirred at ambient temperature for 36 hours, then evaporated to dryness, finally azeotroping with a toluene. The residual oil, a mixture of mono and di-(t-butoxycarbonyl) compounds, was dissolved in methanol (100 ml), treated with aqueous sodium hydroxide (2 M, 25 ml, 50 mM), and stirred at ambient temperature for 2 hours. The mixture was acidified by the addition of citric acid (10% w/v, 80 ml), added to water (500 ml), and methanol removed by evaporation. The resulting precipitate was filtered to give the title product as an off-white solid (6.69 g, 67%).

NMR (DMSO-$d_6$) δ: 1.57 (s, 9H); 8.87 (s, 1H); 10.67 (brSs, 1H). MS SP): 202 (MH$^+$) for $C_7H_{11}N_3O_2S$

3-(4-(1,2,5,6-Tetrahydropyridyl-4-yl)-3,5-difluorophenyl)-5(R)-(N-(t-butoxycarbonyl)-1,3,4-thiadiazol-2-ylaminomethyl)oxazolidin-2-one Hydrochloride Using the method described for the appropriate intermediate of Example 25, apart from routine changes in the eluant used for chromatography, and starting from 3-(4-(1-benzyl-1,2,5,6-tetrahydropyrid-4-yl)-3,5-difluorophenyl-5 (R-(N-(t-butoxycarbonyl)-1,3,4-thiadiazol-2-ylaminomethyl)oxazolidin-2-one (1.54 g, 2.64 mM), gave the title compound (845 mg, 60%).

NMR (DMSO-$d_6$) δ: 1.50 (s, 9H); 2.53 (m, 2H); 3.25 (m overlapped by $H_2O$, 2H); 3.73 (s, 2H); 3.94 (t, 1H); 4.32 (dd, 1H); 4.49 (dd, 1H); 5.10 (m, 1H); 5.89 (s, 1H); 7.35 (d, 2H); 9.21 (s, 1H); 9.32 (brs, 2H); (+1H for HCl salt). MS (ESP): 494 (MH$^+$) for $C_{22}H F_2N_5O_4S$

3-(4-(1-(2,2-Dimethyl-1,3-dioxolan-4(S)-ylcarbonyl)-1,2,5,6-tetrahydroprid-4-yl)-3,5-difluorophenyl)-5(R)-(N-(t-butoxycarbonyl)-1,3,4-thiadiazol-2-ylaminomethyl)oxazolidin-2-one Using the method described for the appropriate intermediate of Example 17, but starting from 3-(4-(1,2,5,6-tetrahydropyrid-4-yl)-3,5-difluorophenyl)-5(R)-(N-(t-butoxycarbonyl)-1,3,4-thiadiazol-2-ylaminomethyl)oxazolidin-2-one hydrochloride (400 mg, 0.755 mM) gave the title compound as an oil (205 mg, 44%).

MS (ESP): 622 (MH$^+$) for $C_2H_{33}F_2N_5O_7S$

EXAMPLE 32

3-(4-(1-Acetoxyacetyl-1,2,5,6-tetrahydropyrid-4-yl)-3,5-difluorophenyl)-5(S)-(1,3,4-thiadiazol-2-ylaminomethyl)oxazolidin-2-one Using the method of Example 28, apart from routine changes in the eluant used for chromatography, and starting from 3-(4-(1-acetoxyacetyl-1,2,5,6-tetrahydropyrid-4-yl)-3, 5-difluorophenyl)-5(R)-(N-(t-butoxycarbonyl)-1,3,4-thiadiazol-2-ylaminomethyl)oxazolidin-2-one (120 mg, 0.20 mM), gave the title product (21 mg, 21%).

NMR (400 MHz. DMSO-d§ δ: 2.10 (s, 3H); 2.34 (brs, 1H); 2.43 (brs, 1H); 3.60 (t, 1H); 3.67 (dd, 1H); 3.73 (dd, 2H); 3.85 (dd, 1H); 4.10 (m, 2H); 4.21 (t, 1H); 4.85 (d, 2H); 4.98 (m, 1H); 5.88 (d, 1H); 7.34 (d, 2H); 8.10 (t, 1H); 8.68 (s, 1H).

MS (ESP): 494 (MH$^+$) for $C_{21}H_{21}F_2N_5O_5S$

The 3-(4-(1-Acetoxyacetyl-1,2,5,6-tetrahydropyrid-4-yl)-3,5-difluorophenyl)-5(R)-(N-(t-butoxycarbonyl)-1,3,4-thiadiazol-2-ylaminomethyl)oxazolidin-2-one intermediate was prepared as follows:

Using the method described for the appropriate intermediate of Example 25, but starting from 3-(4-(1,2,5,6-tetrahydropyrid-4-yl)-3-fluorophenyl)-5(R)-(N-(t-butoxycarbonyl)-1,3,4-thiadiazol-2-ylaminomethyl)oxazolidin-2-one hydrochloride (400 mg, 0.755 mM, see Example 31), gave the title product (135 mg, 30%).

MS (ESP): 594 (MH$^+$) for $C_{26}H_{29}F_2N_5O_7S$

EXAMPLE 33

5(S)Isoxazol-3-ylaminomethyl-3-(3,5-difluoro-4-(1-acetoxyacetyl-1,2,5,6-tetrahydropyrid-4-yl)phenyl) oxazolidin-2-one Reference Example 11, (3.21 g, 5.57 mmol) was dissolved in a solution of trifluoroacetic acid (10 ml) and dichloromethane (10 ml), stirring at ambient temperature for 10 minutes. The solvents were removed by rotary evaporation and the residues azeotroped with toluene (2×), triturated and washed with diethyl ether, and dried to give the title compound as a cream amorphous solid (2.65 g, 100%).

NMR (300 Mz, DMSO-d6), δ/ppm: 2.08 (s, 3H), 2.31 (m, 1H), 2.42 (m, 1H), 3.44 (t, 2H, partially obscured), 3.57 (t, 1H, partially obscured), 3.65(t, 1H, partially obscured), 3.82 (dd, 1H), 4.13 (m, 3H), 4.81 (s, 1H), 4.85 (s, 1H), 4.90 (m, 1H), 5.89 (m, 1H), 6.00 (d, 1H), 6.55 (t, 1H), 7.35 (m, 2H), 8.41 (d, 1H).

The starting material was prepared as follows:

REFERENCE EXAMPLE 8

3-(tert-butyloxycarbonylamino)-isoxazole

To a stirred solution of 3-aminoisoxazole (5.00 g, 59.5 mmol) and 4-(dimethylamino) pyridine (500 mg) in pyridine (100 ml) was added portionwise di-tert-butyl dicarbonate (25.97 g, 119 mmol) and stirred for 18 hours. The solvent was removed by rotary evaporation giving an oil that was dissolved in methanol (100 ml) and treated with NaOH solution (2.5M, 24 ml, 60 mmol), stirred for 2 hours, acidified with citric acid solution (10% w/v, 80 ml), and added to water (500 ml), giving the title compound as a tan coloured solid after filtration and drying (8.89 g, 81%).

NMR (300 Mz, DMSO-d6), δ/ppm: 1.46 (s, 9H), 6.72 (d, 1H), 8.71 (d, 1H), 10.35 (s, broad, 1H). MS: ES+ (M+H) =129 (loss of butylene).

REFERENCE EXAMPLE 9A 3,5-Difluoro-4-(1-benzyl-4-hydroxyhexahydropyrid-4-yl)aniline nBuLi (1.32M in hexanes, 350 ml, 0.462 mol) was added dropwise over 20 minutes to a solution of N,N-(1,2-bis (dimethylsilyl)ethane)-3,5-difluoroaniline, (108.4 g, 0.40 mol, J. Org. Chem., 60, 5255–5261 (1995)) in 800 ml dry ThF at −70° C. under argon. After stirring for a further 4 hours at −70° C., N-benzyl-4-piperidone (87.8 g, 0.46 mol) in 270 ml dry THF was added dropwise over 40 minutes at the same temperature and the reaction allowed to stir to ambient temperature overnight. Solvent was removed in vacuo and the resultant product treated with ice and conc.HCl and extracted with ether. The aqueous acidic phase was then treated with 40% NaOH with cooling, extracted with ether (and worked up by washing with water, with brine and drying with an anhydrous drying agent such as magnesium sulfate or sodium sulfate before evaporation—this work up procedure is referred to as work up in the usual manner hereinafter) to give 144.7 g of a sludge. Analysis by TLC using 10% MeOH/dichloromethane on silica indicated that the desired alcohol was present as approximately 90% of the product, and the crude product was used without further purification. MS: ESP+ (M+H)=319.

REFERENCE EXAMPLE 9B 3,5-Difluoro-4-(1-benzyl-1,2,5,6-tetrahydropyrid-4-yl)aniline The crude product from Reference Example 9A (144.7 g) was suspended in 400 ml conc.HCl and heated at reflux with stirring for 18 hours. TLC showed all starting material had reacted, and after cooling in ice the reaction mixture was taken to pH 11 with conc. $NH_3$ (aq) and extracted three times with dichloromethane. Usual work-up gave 119.5 g of a viscous oil. TLC indicated a purity of ca. 80% and the crude product was used without further purification. MS: ESP+ (M+H)=301.

REFERENCE EXAMPLE 9C

N-Benzyloxycarbonyl-3,5-difluoro-4(1-benzyl-1,2,5, 6-tetrahydropyrid-4-yl)aniline The crude aniline from Reference Example 9B (3.2 g, 10.7 mmol) in 10 ml of acetone was added in one portion to a stirred solution of sodium dihydrogen phosphate (3.0 g) in 30 ml water. The resulting mixture was cooled to 5–10C and a solution of benzylchloroformate (2.18 g, 1.8 ml, 12.8 mmol) in 10 ml of acetone was added dropwise. The mixture was stirred for a further hour at ice-bath temperature and then at ambient temperature for 2 hours. The mixture was diluted with 80 ml water, basified with conc.$NH_3$(aq) and extracted with EtOAc. Usual work-up gave a viscous oil which was purified by flash chromatography (Merck 9385 silica, EtOAc/isohexane (3:7 eluant) and triturated with isohexane to give a solid (1.53 g 33%).

MS: ESP+ (M+H)=434.

REFERENCE EXAMPLE 9D

5(R-Hydroxymethyl-3-(4-(1-benzyl-1,2,5,6-tetrahydropyrid-4-yl)-3,5-difluorophenyl)oxazolidin-2-one The benzylurethane from Reference Example 9C (5.54 g, 12.76 mmol) in 50 ml dry THF was cooled to −70° C. under nitrogen and 8.80 ml of 1.6M nBuLi in hexanes (14.08 mmol) added dropwise at the same temperature. After 20 minutes at the same temperature a solution of (R)-glycidyl butyrate (2.00 g, 13.88 mmol in 5 ml THF) was added dropwise and the mixture stirred for 30 minutes at −70° C., and then stirred to ambient temperature overnight. After quenching with 100 ml 10% ammonium chloride, the mixture was extracted with EtOAc and usual work-up to give an oily solid, which was purified by flash chromatography (Merck C60 silica, 5% MeOH/dichloromethane eluant) to give a crystalline solid (4.40 g, 86%). MS: ESP+ (M+H) =401.

$^1$H-NMR (250 MHz, DMSO-d6): δ=2.32 (m, 2H), 2.63 (t, 2H), 3.05 (m, 2H), 3.50–3.72 (m, 4H), 3.82 (dd, 1H), 4.06 (t, 1H), 4.73 (m, 1H), 5.18 (t, 1H), 5.78 (m, 1H).

REFERENCE EXAMPLE 9

5(R)-(N-isoxazol-3-yl-N-tertbutoxycarbonyl)aminomethyl)-3-(3,5-difluoro-4(1-benzyl-1,2,5,6-tetrahydropyrid-4-yl)phenyl)oxazolidin-2-one To a stirred solution of 5(R)-hydroxymethyl-3-(3,5-difluoro-4-(1-benzyl-1,2,5,6-tetrahydropyrid-4-yl)phenyl)oxazolidin-2-one (Reference Example 9D; 6.01 g, 15 mmol), 3-(tert-butyloxycarbonylamino)-isoxazole (3.04 g, 16.5 mmol; Reference Example 8) and tri-n-butyl phosphine (4.55 g, 22.5 mmol, 5.55 ml) in dry THF (250 ml), under N2, cooled to 0° C., was added portionwise 1,1'-(azodicarbonyl)-di-piperidine (5.68 g, 22.5 mmol). The reaction was stirred at 0° C. for 30 mins, allowed to come to ambient temperature and stirred for a further 4 hours, with the formation of a white precipitate. The mixture was filtered, concentrated by rotary evaporation to an oil which was purified by MPLC (Merck 9385 silica, 50% EtOAc/Hexane), concentrating the pure fractions to give the title compound as a white brittle foam (7.74 g, 91%).

NMR (300 Mz, DMSO-d6), δ/ppm: δ 2.33 (m, 2H), 3.41 (t, 2H), 3.53 (m, 1H), 3.66 (m, 1H), 3.79 (dd, 1H), 4.10 (m, 5H), 4.57 (m, 1H), 4.89 (m, 1H), 5.83 (m, 1H), 5.98 (d, 1H), 6.50 (t, 1H), 7.33 (d, 2H), 8.38 (d, 1H). MS: ES+ (M+H) =567.

REFERENCE EXAMPLE 10

5(R)-(N-isoxazol-3-yl-N-tertbutoxycarbonyl)aminomethyl)-3-(3,5-difluoro-4-(1,2,5,6-tetrahydropyrid-4-yl)phenyl)oxazolidin-2-one, hydrochloride To a stirred solution, cooled to 0–4° C., of Reference Example 9, (5.00 g, 8.82 mmol) in dichloromethane (50 ml), under N2, was added N,N-diisopropylethylamine(462 μl, 2.65 mmol) and 1-chloroethyl chloroformate (1.64 g, 11.5 mmol, 1.24 ml) and allowed to stir for 10 minutes. The mixture was chromatographed by MPLC (Merck 9385 silica, 40% EtOAc/Hexane) and pure fractions were concentrated by rotary evaporation and taken into MeOH and heated to 60° C., with stirring, for 30 mins. Removal of the solvent and trituration with diethylether gave the title compound as a white amorphous powder (3.66 g, 81%). MS: ES+ (M+H)=477.

REFERENCE EXAMPLE 11

5(R)-(N-isoxazol-3-yl-N-tertbutoxycarbonyl)aminomethyl)-3-(3,5-difluoro-4-(1-acetoxyacetyl-1,2,5,6-tetrahydropyrid-4-yl)phenyl)oxazolidin-2-one To a suspension of Reference Example 10, (3.00 g, 5.85 mmol) and sodium hydrogen carbonate (2.46 g, 29.3 mmol) in acetone (100 ml)/water (50 ml), stirred at 0° C., under N$_2$, was added dropwise a solution of acetoxyacetyl chloride (879 mg, 6.44 mmol, 6921 μl) in acetone (5 ml). The reaction was stirred at 0° C. for 30 min and at ambient temperature for a further 90 min, then water was added and the mixture extracted with EtOAc (2×) and the organic extracts washed with water and saturated brine, dried (sodium sulfate) and concentrated by rotary evaporation to give the title compound as a crisp white foam (3.29 g, 98%).

NMR (300 Mz, DMSO-d6), δ/ppm: 1.48 (s, 9H), 2.08 (s, 3H), 2.30 (m, 1H), 2.42 (m, 1H), 3.60 (dt, 2H), 3.86 (dd, 1H), 3.97 (dd, 1H), 4.10 (m, 2H), 4.22 (m, 2H), 4.82 (s, 1H), 4.87 (s, 1H), 5.03 (m, 1H), 5.89 (m, 1H), 6.89 (d, 1H), 7.33 (m, 2H), 8.81 (d, 1H).

EXAMPLE 34

5(S)-Isoxazol-3-ylaminomethyl-3-(3,5-difluoro-4-(1-hydroxyacetyl-1,2,5,6 tetrahydropyrid-4-yl)phenyl)oxazolidin-2-one Example 33, (2.0 g, 4.2 mmol) was suspended in saturated methanolic ammonia (25 ml), with stirring, heating to 50° C., for 10 min to completely dissolve the solid cooled to room temperature and allowed to stand for 18 hours with the formation of some yellow precipitate which was further precipitated with diethyl ether and filtered to give the title compound as a yellow amorphous powder (1.82 g, 100%).

NMR (300 Mz, DMSO-d6), δ/ppm: 2.32 (m, 2H), 3.43 (t, 2H), 3.53 (t, 1H), 3.67 (m, 1H), 3.79 (dd, 1H), 4.10 (m, 5H), 4.57 (m, 1H), 4.88 (m, 1H), 5.85 (m, 1H), 5.98 (d, 1H), 6.50 (t, 1H), 7.30 (m, 2H), 8.37 (d, 1H). MS: ES+ (M+H)=435.

EXAMPLE 35

5(S)-Isoxazol-3-ylaminomethyl-3-(3,5-difluoro-4-(1-(2(S),3-dihydroxypropanoyl)-1,2,5,6-tetrahydropyrid-4-yl)phenyl)oxazolidin-2-one Reference Example 12, (420 mg, 0.69 mmol) was dissolved in trifluoroacetic acid (5 ml) and for stirred for 10 mins. THF(5 ml)/water(5 ml) was then added and stirring continued for a further 30 minutes. Water was then added and the reaction extracted with ethyl acetate (2×) and the extracts washed with water, saturated sodium hydrogen carbonate solution (2×) and saturated brine, then dried (sodium sulfate) and concentrated by rotary evaporation to give the title compound as a white solid (160 mg, 50%).

NMR (300 Mz, DMSO-d6), δ/ppm: 2.23–2.42 (m, 2H), 3.40–3.60 (m, 4H), 3.72 (dd, 1H), 3.80 (dd, 2H), 4.13 (m, 3H), 4.37 (m, 1H), 4.67 (m, 1H), 4.89 (m, 1H), 4.96 (m, 1H), 5.85 (m, 1H), 5.98 (d, 1H), 6.51 (t, 1H), 7.32 (m, 2H), 8.37 (d, 1H).

MS: ES+ (M+H)=465.

The starting material was prepared as follows:

REFERENCE EXAMPLE 12

5(R)-(N-isoxazol-3-yl-N-tertbutoxycarbonyl)aminomethyl)-3-(3,5-difluoro-4(1-(2,2-dimethyl-1,3-dioxolan-4(S)-ylcarbonyl]-1,2,5,6-tetrahydropyrid-4-yl)phenyl)oxazolidin-2-one To a stirred solution of Reference Example 10, (650 mg, 1.27 mmol) and pyridine(514 μl, 6.35 mmol) in dichloromethane (25 ml), cooled to 0° C., under N2, was added dropwise (S)-(+)-2,3-0-isopropylideneglycinoyl chloride (EP 0 413401 A2) (418 mg, 2.54 mmol). The reaction was stirred for 30 min at 0° C. then 1 hour at ambient temperature and the organic phase was washed with water (10 ml), concentrated by rotary evaporation and the title compound was obtained by crystallisation with methanol as a white powder (500 mg, 65%).

NMR (300 Mz, DMSO-d6), δ/ppm: 1.30 (s, 3H), 1.32 (s, 3H), 1.48 (s, 9H), 2.31 (m, 1H), δ 2.42 (m, 1H), 3.67 (t, 1H), 3.75 (t, 1H), 3.87 (dd, 1H), 3.96 (dd, 1H), 4.01–4.32 (m, 6H), 4.90 (m, 1H), 5.01 (m, 1H), 5.90 (m, 1H), 6.88 (d, 1H), 7.35 (m, 2H), 8.82 (d, 1H). MS: ES+ (M+H)=605.

There are no Examples 36 or 37.

EXAMPLE 38

5(S)-Isoxazol-3-ylaminomethyl-3-(3,5-difluoro-4-(3,6-dihydro-(2H)-pyran-4-yl)phenyl)oxazolidin-2-one To a stirred solution of Reference Example 13, (273 mg, 0.49 mmol) in AcOH (4.5 ml)/water (0.5 ml), under N2, was added zinc dust (160 mg, 2.45 mmol). The reaction was stirred for 16 h, the mixture filtered through celite, washing the filter pad with AcOH (0.5 ml). The solvent was removed from the filtrate by rotary evaporation and the gum obtained was dissolved in dichloromethane(20 ml) and washed with water(10 ml), saturated sodium hydrogen carbonate solution (10 ml) and brine (10 ml). The organic layer was dried (sodium sulfate), evaporated and the title compound obtained as a pale yellow solid (140 mg, 76%) upon trituration with diethyl ether and drying.

NMR (300 Mz, DMSO-d6), δ/ppm: δ 2.30 (m, 1H), 3.45 (m, 1H), 3.81 (m, 3H), 4.18 (m, 3H), 4.90 (m, 1H), 5.91 (br s, 1H), 6.00 (d, 1H), 6.53 (m, 1H), 7.34 (m, 2H), 8.40 (d, 1H).

The starting material was prepared as follows:

REFERENCE EXAMPLE 13

5(R)-(N-isoxazol-3-yl-N-tertbutoxycarbonyl)aminomethyl)-3-(3,5-difluoro-4-(3,6-dihydro-(2H)-pyran-4-yl)phenyloxazolidin-2-one To a stirred solution of 3-(TROC-amino)-isoxazole (Reference Example 1; 310 mg, 1.20 mmol), S(R)-hydroxymethyl-3-(3,5-difluoro-4-(3,6-dihydro-(2H)-pyran-4-yl)phenyl)oxazolidin-2-one (see WO97/30995 Reference Example 14; 250 mg, 0.80 mmol) and tri-n-butyl phosphine (242 mg, 1.20 nmol) in dry THF (10 ml), under N2, cooled to 0° C., was added a solution of 1,1'-(azodicarbonyl)-di-piperidine (303 mg, 1.20 mmol) in dry THF (1.5 ml). The reaction was stirred at room temperature for 2 h, the solvent removed by evaporation. The residue was dissolved in dichloromethane, cooled for 30 mins and filtered to remove the white precipitate, then chromatographed by MPLC (Merck 9385 silica, 30% EtOAc/Hexane), and pure fractions evaporated to give the title compound as clear glass (286 mg, 65%).

NMR (400 Mz, DMSO-d6), δ/ppm: δ 2.27 (n, 2H), 3.78 (m, 2H), 3.89 (dd, 1H), 4.16 (m, 4H), 4.35 (dd, 1H), 5.02 (m, 3H), 5.87 (br s, 1H), 6.85 (d, 1H), 7.26 (m, 2H), 8.87 (d, 1H). MS: ES+ (M+H)=552 (3× Cl isotope pattern).

EXAMPLE 39

5(S)-Isoxazol-3-ylaminomethyl-3-(3-fluoro-4-(1-(2-(N-ethoxycarbonylmethyl)-carbamoyloxy)-acetyl-1, 2,5,6-tetrahydropyrid-4-yl)phenyl)oxazolidin-2-one In portions, ethyl 2-isocyanatoacetate (3×170 mg, 3.96 mmol) was added dropwise to a stirred suspension of Example 5, (500 mg, 1.2 mmol), triethylamine (33411, 2.40 mmol) and 4-(dimethylamino) pyridine (8 mg) in dioxane (20 ml) and the reaction heated to 80° C. for 64 h. The solvent was removed by rotary evaporation and the title compound isolated after MPLC (Merck 9385 silica, 80–100% EtOAc/Hexane) and trituration with diethyl ether as a white powder (410 mg, 63%).

NMR (300 Mz, DMSO-d6), δ/ppm: 1.77 (t, 3H), 2.41 (m, 2H), 3.43 (t, 2H), 3.53 (m, 1H), 3.62 (m, 1H), 3.74 (d, 2H), 3.80 (dd, 1H), 4.03–4.18 (m, 5H), 4.68–4.77 (m, 2H), 4.87 (m, 1H), 5.98 (m, 2H), 6.50 (t, 1H), 7.27–7.52 (m, 3H), 7.73 (t, 1H), 8.37 (d, 1H). MS: ES+ (M+H)=546.

EXAMPLE 40

5(S)-Isoxazol-3-ylaminomethyl-3-(3-fluoro-4-(1-(2-(N-carboxymethyl)-carbamoyloxy)-acetyl-1,2,5,6-tetrahydropyrid-4-yl)phenyl)oxazolidin-2-one To a stirred solution of Example 39, (500 mg, 0.9 mmol) in methanol/water (1:1,25 ml) was added a solution of lithium hydroxide monohydrate (43.5 mg, 11.0 mmol) in water (2.5 ml). The reaction was stirred at ambient temperature for 20 min, added to water (100 ml) and stirred with Dowex 50Wx8(H) resin (4 ml) for 5 minutes. The resin was removed by filtration and the solvent removed by rotary evaporation to give a gum which was dissolved in 10% methanol/dichloromethane and the title compound was obtained as a crisp pale yellow foam (433 mg, 93%) by evaporation and drying.

NMR (300 Mz, DMSO-d6), δ/ppm: 2.42 (m, 2H), 3.10 (t, 1H), 3.33–3.67 (m, 6H), 3.81 (dd, 1H), 3.98–4.20 (m, 3H), 4.72 (m, 2H), 4.86 (m, 1H), 5.99 (m, 2H), 6.52 (t, 1H), 7.15–7.53 (m, 4H), 8.37 (d, 1H). MS: ES– (M–H)–=516.

EXAMPLE 41

5(S)-Thiazol-2-ylaminomethyl)-3-(3-fluoro-4-(3,6-dihydro-(2H)-pyran-4-yl)phenyl)oxazolidin-2-one To a stirred solution of 2-aminothiazole (228 mg, 2.22 mmol) in dry THF (5 ml), cooled to –78° C., under argon, was added slowly n-BuLi (1.33M, 1.67 mL 2.22 mmol), followed after 30 mins by 5(R)-methylsulfonyloxymethyl-3-(3-fluoro (3,6-dihydro-(2H)-pyran-4-yl)phenyl)oxazolidin-2-one (prepared using standard chemistry from the 5(R) hydroxy methyl compound by analogy with the 3,5-difluoro compound; see WO97/30995; 542 mg, 1.46 mol) suspended in dry THF (25 ml). The reaction was stirred, for 18 h at the mixture with chloroform (3×10 ml). The extracts were dried (magnesium sulfate ambient temperature, then heated to 50° C. for 2 h. The reaction was quenched with ammonium chloride solution (10% w/v, 30 ml) and acidified to pH 3.0 with aqueous HCl, extracting) concentrated by rotary evaporation, chromatographed by MPLC (Merck 9385 silica, 3% methanol/dichloromethane eluent) and the pure fractions combined to give the crude product (68 mg) that was recrystallised from ethanol, washed with diethyl ether and dried, giving the title compound as a yellow powder (40 mg, 7.3%).

NMR (300 Mz, DMSO-d6), δ/ppm: 2.41 (m, 2H), 3.25 (m, 2H), 3.65 (dd, 1H), 3.80 (t, 1H), 3.91 (dd, 1H), 3.99 (dd, 1H), 4.18 (m, 3H), 4.63 (m, 1H), 6.06 (m, 1H), 7.23 (dd, 1H), 7.38 (m, 2H), 7.44 (d, 1H), 7.59 (dd, 1H). MS: ES+ (M+H)=376.

EXAMPLE 42

5(S(N-Methyl)imidazol-2-ylaminomethyl)-3-(3-fluoro-4(3,6-dihydro-(2H)-pyran-4-yl)phenyl)oxazolidin-2-one To a stirred solution of 1-methyl-2-aminoimidazole (401 mg, 3.0 mmol) in dry THF (10 ml), cooled to −78° C., under argon, was added slowly n-BuLi (1.33M, 4.5 ml, 6.0 mmol), followed after 1 h by 5(R)-methylsulfonyloxymethyl-3-(3-fluoro-4-(3,6-dihydro-(2H)-pyran-4-yl)phenyl)oxazolidin-2-one (see Example 41; 542 mg, 1.46 mol) suspended in dry THF (20 ml). The reaction was allowed to come to room temperature and then refluxed for 18 h. The reaction was quenched with ammonium chloride solution (10% w/v, 30 ml), extracting the mixture with chloroform (5×20 ml). The extracts were dried (sodium sulfate) concentrated by rotary evaporation, chromatographed by MPLC (Merck 9385 silica, 3% methanol/dichloromethane eluent) and the pure fractions combined to give the title compound (25 mg, 4.6%).

NMR (300 Mz, DMSO-d6), δ/ppm: 2.40 (m, 2H), 3.36–3.56 (m, 5H), 3.82 (m, 3H), 4.06–4.32 (m, 4H), 5.06 (m, 1H), 6.05 (m, 1H), 6.82 (s, 1H), 7.11 (s, 1H), 7.32 (m, 2H), 7.55 (d, 1H). MS: ES+ (M+H)=373.

EXAMPLE 43

5(S)Oxazol-2-ylaminomethyl-3-(3-fluoro-4-(3,6-dihydro-(2H)-pyran-4 yl)phenyl)oxazolidin-2-one To a stirred partial solution of 2-aminooxazole (169 mg, 2.0 mmol) in dry THF (10 ml), cooled to −78° C., under argon, was added slowly n-BuLi (1.33M, 1.5 ml, 2.0 mmol), followed after 1 h by 5(R)-methylsulfonyloxymethyl-3-(3-fluoro-4-(3,6-dihydro-(2H)-pyran-4-yl)phenyl)oxazolidin-2-one (see Example 41; 371 mg, 11.0 mol) suspended in dry THF (20 ml). The reaction was allowed to come to room temperature and then refluxed for 24 h. The reaction was quenched with ammonium chloride solution (10% w/v, 30 ml), extracting the mixture with chloroform (3×50 ml). The extracts were dried (magnesium sulfate), concentrated by rotary evaporation chromatographed by MPLC (Merck 9385 silica, 3–10% gradient methanol/dichloromethane eluent) and the pure fractions combined, concentrated and triturated with diethyl ether to give the title compound (25 mg, 4.6%).

NMR (300 Mz, DMSO-d6), δ/ppm: 2.31 (m, 2H), 3.35 (m, 2H, obscured), 3.64 (dd, 1H), 3.84 (t, 2H), 3.90 (m, 1H), 4.15 (m, 1H), 4.24 (m, 2H), 4.46 (m, 1H), 5.97 (m, 1H), 6.90 (m, 1H), 7.19 (m, 2H, partially obscured), 7.37 (dd, 1H), 7.44 (dd, 1H).

MS: ES+ (M+H) 360.

EXAMPLE 44

5(S)-(Isoxazol-3-ylaminomethyl)-3-(4-(1,2,5,6-tetrahydropyrid-4-yl)phenyl)oxazolidin-2-one, trifluoroacetate The starting material Reference Example 14, (2.65 g, 4.9 mM) was disolved in TFA (10 ml), giving a transient intense yellow colour and gas evolution. It was then heated briefly to reflux. The TFA was evaporated and the residue was taken into ethyl acetate. The title compound crystallised (1.56 g, 70%).

NMR (300 Mz, DMSO-d6): δ 2.69(s, 2H), 3.31(d, 2H), 3.44(t, 2H), 3.78(s, 2H), 3.84(d of d, 1H), 4.18(t, 1H), 4.88(m, 1H), 6.00(s, 1H), 6.20(s, 1H), 6.59(t, 1H), 7.53(AB, 4H), 8.40(s, 1H), 8.89(s, 2H). MS: ES+ (M+H)=312.

The starting material was prepared as follows:

REFERENCE EXAMPLE 14

5(R)-(N-isoxazol-3-yl-N-tertbutoxycarbonyl)aminomethyl)-3-(4-(1-tertbutoxycarbonyl-1,2,5,6-tetrahydropyrid-4-yl)phenyl)oxazolidin-2-one To a stirred solution of 5(R)-hydroxymethyl-3-(1-tertbutoxycarbonyl-1,2,5,6-tetrahydropyrid-4-yl)phenyl)oxazolidin-2-one (prepared by analogy to the 3,5-difluoro compound—see WO97/30995 Reference Example 11; 2.24 g, 6.0 mM) and N-Boc-isoxazole (1.66 g, 9.0 mM) in dry THF (30 ml) under $N_2$, was added tri-N-butylphosphine (1.82 g, 9.0 mM) followed by portionwise addition of ADDP (2.27 g, 9.0 mM). The reaction mixture was stirred for 18 hrs at ambient temperature. It was evaporated and chromatographed by MPLC (35% ethyl acetate/isohexane, Merck 9385 silica). The title compound crystallised on trituration with isohexane (2.75 g, 85%).

NMR (300 Mz, DMSO-d6): δ 1.35(s, 9H), 1.43(s, 9H), 2.4(partially obscured by DMSO), 3.48(t, 1H), 3.78(4 line, 1H), 3.92(m, 3H), 4.18(m, 2H), 4.92(m, 1H), 6.18(s, 1H), 6.80(s, 1H), 7.43(AB, 4H), 8.75(s, 1H). MS: ES+ (M+H) =485 (-butylene), 429 (−2× butylene).

EXAMPLE 45

5(S)-(Isoxazol-3-ylaminomethyl)-3-(4=(1-acetoxyacetyl-1,2,5,6-tetrahydropyrid-4-yl)phenyl)oxazolidin-2-one To a stirred solution of the starting material Example 44, (590 mg, 1.3 mM) in acetone (20 ml)/water (10 ml), was added $NaHCO_3$ (1.09 g, 13 mM) and the mixture was cooled to 04° C. Acetoxyacetyl chloride (350 mg, 2.6 mM) was added slowly and the reaction mixture was stirred at 0–5° C. for 20 mins then allowed to warm to room temperature. The reaction mixture was diluted with water and extracted with ethyl acetate. The organic phase was washed with sat. NaCl, dried over anh. $Na_2SO_4$ and evaporated. The title compound crystallised on trituration with ether (570 mg, 100%).

NMR (300 Mz, DMSO-d6): δ 2.08(s, 3H), 2.55(partially obscured by DMSO), 3.45(t, 2H), 3.58(t, 1H), 3.67(t, 1H), 3.84(d of d, 1H), 4.10(s, 2H), 4.18(t, 1H), 4.85(m, 3H), 6.00(s, 1H), 6.15(broad d, 1H), 6.53(t, 1H), 7.50(m, 4H), 8.38(s, 1H).

MS: ES+ (M+H)=441.

EXAMPLE 46

5(S)-(Isoxazol-3-ylaminomethyl)-3-(4-(1-hydroxyacetyl-1,2,5,6-tetrahydropyrid-4-yl)phenyl)oxazolidin-2-one A partial solution of the starting material Example 45, (500 mg, 1.1 mM) in sat. $NH_3$/methanol (15 ml) was warmed to give a clear solution after 5 min. The reaction mixture was stirred for 18 hr. at ambient temperature. The solvent was evaporated to a small volume and ether was added giving the title compound as a crystalline solid (394 mg, 90%).

NMR (300 Mz, DMSO-d6): δ 2.5(obscured by DMSO), 3.38(t, 2H), 3.48(t, 1H), 3.62(t, 1H), 3.73(d of d, 1H), 4.6(m, 5H), 4.52(m, 1H), 4.79(m, 1H), 5.94(s, 1H), 6.09(d, 1H), 6.50(t, 1H), 7.44(AB, 4H), 8.32(s, 1H). MS: ES+ (M+H)=399.

EXAMPLE 47

5(S)-(Isoxazol-3-ylaminomethyl)-3-(4-(1-(2,2-dimethyl-1,3-dioxolan-4(S) ylcarbonyl)-1,2,5,6-tetrahydropyrid-4-yl)phenyl)oxazolidin-2-one A stirred partial solution of the starting material Example 44, (300 mg, 0.66 mM) and NaHCO$_3$ (278 mg, 3.3 mM) in acetone (8 ml)/water (4 ml), was cooled to 0–4° C. A solution of (S)-(+)-2,3,0-isopropylideneglycinoyl chloride (217 mg, 1.32 mM) in acetone (1 ml) was added slowly and the reaction mixture was then allowed to warm to room temperature. A further addition of the acyl chloride (139 mg, 0.66 mM) was required for complete reaction. The reaction mixture was diluted with water and extracted with ethyl acetate. The organic phase was washed with sat. NaCl, dried over anh. Na$_2$SO$_4$ and evaporated. The title compound crystallised on trituration with ether (258 mg, 84%).

NMR (300 Mz, DMSO-d6): δ 1.32(m, 6H), 2.55(partially obscured by DMSO), 3.44(t, 2H), 3.68(m, 2H), 3.82(d of d, 11H), 4.15(m, 5H), 4.88(m, 2H), 6.01(s, 2H), 6.16(s, 1H), 6.55(t, 1H), 7.50(AB, 4H), 8.40(s, 1H). MS: ES+ (M+H)=429.

EXAMPLE 48

5(S)-(Isoxazol-3-ylaminomethyl)-3-(4-(1-(2(S),3-dihydroxypropanoyl)-1,2,5,6-tetrahydropyrid-4-yl) phenyl)oxazolidin-2-one A solution of the starting material Example 47, (220 mg, 0.47 mM) in THF (6 ml)/1 N.aq.HCl (2 ml) was stirred for 3 days at ambient temperature. The solution was partially evaporated giving a gum and the aqueous was decanted off. The title compound crystallised on trituration of the gum with ethanol I ether (141 mg, 70%).

NMR (300 Mz, DMSO-d6): δ 2.5(obscured by DMSO), 3.45(m, 4H), 3.80(m, 3H), 4.25(m, 4H), 4.73(broad s, 1H), 4.89(m, 2H), 5.98(s, 1H), 6.15(s, 1H), 6.55(s, 1H), 7.48(m, 4H), 8.36(s, 1H). MS: ES+ (M+H)=429.

EXAMPLE 49

5(S)-(1,2,4-Oxadiazol-3-yl-aminomethyl)-3-(3,5-difluoro-4-(1-(2(S),3-dihydroxypropanoyl)-1,2,5,6-tetrahydropyridyl)phenyl)oxazolidin-2-one To a stirred solution of Reference Example 15, (278 mg, 0.46 mmol) in dichloromethane (4 ml) was added trifluoroacetic acid (4 ml) and the reaction allowed to stir at room temperature for 0.5 hours. Water (0.8 ml) was then added and the reaction stirred for a further 2 hours. The solvent was removed under reduced pressure and the resulting residue taken into methanol (15 ml). The solution was made slightly basic (pH9) by the addition of conc.ammonia solution. The solvent was removed by evaporation and the reaction purified by silica Bond Elute (5% methanol in dichloromethane).

Again the solvent was removed to yield the title compound as a white foam (152 mg, 71%).

$^1$H-NMR (300 MHz, DMSO-d6): δ=2.27–2.43 (m, 2H), 3.40–3.60 (m, 4H), 3.73 (d, 2H), 3.83 (dd, 1H), 4.05–4.41 (m, 4H), 4.72 (m, 1H), 4.90 (m, 1H), 5.02 (m, 1H), 5.88 (broad s, 1H), 7.26–7.39 (m, 3H), 9.04 (s, 1H). MS: ESP+ (M+H)$^+$=466.

The starting material was prepared as follows:

REFERENCE EXAMPLE 15

5(R)-(N-1,2,4-oxadiazol-3-yl-N-tertbutoxycarbonyl)-aminomethyl)-3-(3,5-difluoro-4-(1-(2,2-dimethyl-1,3-dioxolan-4(S)-ylcarbonyl)-1,2,5,6-tetrahydropyrid-4-yl)phenyl)oxazolidin-2-one To a stirred solution of the appropriate intermediate of Example 20 (600 mg, 1.37 mmol) in anhydrous THF (30 ml) under an atmosphere of nitrogen was added 3-t-butyloxycarbonylamino-1,2,4-oxadiazole (304 mg, 1.64 mmol) and tri-n-butylphosphine (510 μL, 2.05 mmol). The mixture was cooled to 0° C. and 1,1'-(azodicarbonyl)-di-piperidine (518 mg, 2.05 mmol) was added portionwise. The reaction was allowed to warn to room temperature and stir for 18 hours. The THF was removed under reduced pressure and the resulting residue taken into dichloromethane (15 ml) and cooled to 0° C. A white solid precipitated and the solution was filtered and purified by MPLC (Merck 9385 silica, 40–60% ethyl acetate in iso-hexane). The solvent was removed under reduced pressure to give a clear, colourless oil which was triturated with ether to yield the title compound as a fine white powder (291 mg, 35%).

$^1$H-NMR (300 MHz, DMSO-d6): δ=1.31 (d, 6H), 1.47 (s, 9H), 2.27–2.48 (m, 2H), 3.61–4.28 (m, 10H), 4.87–5.02 (m, 2H), 5.89 (broad s, 1H), 7.33 (d, 2H), 9.54 (s, 1H).

MS: ESP+ (M+H)$^+$=606.

EXAMPLE 50

5(S)-(1,2,4-Oxadiazol-3-yl-aminomethyl)-3-(3,5-difluoro-4-(1-hydroxyacetyl-1,2,5,6-tetrahydropyrid-4-yl)phenyl)oxazolidin-2-one To a stirred solution of Reference Example 19 (240 mg, 0.55 mmol) in dichloromethane (4 ml) was added trifluoroacetic acid (4 ml) and the reaction allowed to stir at room temperature for 1 hour. The solvent was removed under reduced pressure and the resulting residue taken into methanol (15 ml). The solution was made slightly basic (pH9) by the addition of conc. ammonia solution. The solvent was removed by evaporation and the reaction purified by MPLC (Merck 9385 silica, 5% methanol in dichloromethane). The solvent was concentrated under reduced pressure and the product precipitated in the remaining solvent. The product was filtered, washed with fresh ice-cold methanol and then triturated with ether to give the title compound as a white solid (135 mg, 69%).

$^1$H-NMR (300 MHz, DMSO-d6): δ=2.25–2.44 (m, 2H), 3.42–3.59 (m, 3H), 3.69 (m, 1H), 3.83 (dd, 1H), 4.0–4.21 (m, 5H), 4.55–4.70 (m, 1H), 4.89 (m, 1H), 5.81–5.91 (m,

1H), 7.29–7.40 (m, 3H), 9.05 (s, 1H). MS: ESP+ (M+H)+ =436.

The starting material was prepared as follows:

REFERENCE EXAMPLE 16

5(R)-(N-1,2,4-oxadiazol-3-yl-N-tertbutoxycarbonyl) amino-methyl)-3-(3,5-difluoro-4(1-benzyl-1,2,5,6-tetrahydropyrid-4-yl)phenyl)oxazolidin-2-one 5(R)-hydroxymethyl-3-(3,5-difluoro-4-(1-benzyl-1,2,5,6-tetrahydropyrid-4-yl)phenyl)oxazolidin-2-one (Reference Example 9D; 1.65 g, 4.13 mmol), 3-t-butyloxycarbony-lamino-1,2,4-oxadiazole (1.14 g, 6.19 mmol), tri-n-butylphosphine (1.52 ml, 6.19 mmol), and 1,1'-(azodicarbo-nyl)-di-piperidine (1.56 g, 6.19 mmol) were reacted in anhydrous THF (60 ml) using the general method of Reference Example 15. The reaction mixture was then purified by MPLC (Merck 9385 silica, 60% ethyl acetate in isohexane) and the solvent removed under reduced pressure to give the title compound as a white foam (1.56 g, 67%).

$^1$H-NMR (300 MHz, DMSO-d6): δ=1.47 (s, 9H), 2.32 (broad s, 2H), 2.62 (t, 2H), 3.05 (broad s, 2H), 3.60 (s, 2H), 3.85 (dd, 1H), 4.0 (m, 1H), 4.14–4.28 (m, 2H), 4.97 (m, 1H), 5.79 (broad s, 1H), 7.21–7.38 (m, 7H), 9.53 (s, 1H). MS: ESP+ (M+H)+=568.

REFERENCE EXAMPLE 17

5(R)-(N-1,2,4-oxadiazol-3-yl-N-tertbutoxycarbonyl) amino-methyl)-3 (3,5-difluoro-4-(1,2,5,6-tetrahydro-pyrid-4-yl)phenyl)oxazolidin-2-one To a stirred solution of Reference Example 16 (1.55 g, 2.73 mmol) and N,N-diisopropylethylamine (142 µL, 20.3 mmol) in dichloromethane (25 ml) under an atmosphere of nitrogen and at 0–4° C. was added dropwise 1-chloroethyl chloroformate (384 µL, 3.55 mmol). The reaction was allowed to stir for 30 minutes at 0° C. and the dichloromethane removed under reduced pressure to yield a brown residue. Methanol (25 ml) was added and the resulting brown solution heated at 60° C. for 30 minutes on a water bath. The methanol was removed under reduced pressure to yield a brown/red residue which was purified by silica Bond Elut (25% methanol in dichloromethane). The solvent was removed under reduced pressure to give the title compound as a white foam (726 mg, 52%).

$^1$H-NMR (300 MHz, DMSO-d6): δ=1.44 (s, 9H), 2.50 (2H, Obscured by DMSO), 3.28 (t, 2H), 3.74 (broad s, 2H), 3.86 (dd, 1H), 3.95–4.03 (m, 1H), 4.15–4.25 (m, 2H), 4.98 (m, 1H), 5.90 (broad s, 1H), 7.37 (d, 2H), 9.28 (broad s, 2H), 9.55 (s, 1H).
MS: ESP+ (M+H)+=478.

REFERENCE EXAMPLE 18

5(R)-(N-1,2,4-oxadiazol-3-yl-N-tertbutoxycarbonyl) amino-methyl)-3-(3,5-difluoro-4-(1-acetoxyacetyl-1, 2,5,6-tetrahydropyrid-4-yl)phenyl)-oxazolidin-2-one To a stirred solution of Reference Example 17 (720 mg, 1.40 mmol) and NaHCO$_3$ (1.18 g, 14.0 mmol) in acetone (20 ml)/water (10 ml) at 0–4° C. was added dropwise acetoxy-acetyl chloride (301 µL, 2.80 mmol). The reaction was allowed to warm to room temperature and stir for 1 hour. The reaction was diluted with water and the product extracted with ethyl acetate. The combined organic phases were washed with sat. NaCl, dried over MgSO$_4$, and evaporated under reduced pressure. The resulting yellow oil was triturated with ether to give the title compound as an off-white solid (647 mg, 80%).

$^1$H-NMR (300 MHz, DMSO-d6): δ=1.45 (s, 9H), 2.10 (s, 3H), 2.26–2.46 (m, 2H), 3.51–3.68 (m, 2H), 3.85 (dd, 1H), 3.95–4.01 (m, 1H), 4.07–4.13 (m, 2H), 4.16–4.27 (m, 2H), 4.79–4.88 (m, 2H), 4.96 (m, 1H), 5.86 (m, 1H), 7.33 (d, 2H), 9.53 (s, 1H).
MS: ESP+ (M+H)+=578.

REFERENCE EXAMPLE 19

5(R)-(N-1,2,4-oxadiazol-3-yl-N-tertbutoxycarbonyl) amino-methyl)-3-(3,5-difluoro-4-(1-hydroxyacetyl-1,2,5,6-tetrahydropyrid-4-yl)phenyl)-oxazolidin-2-one Reference Example 18, (640 mg, 1.1 mmol) was stirred under an atmosphere of nitrogen in saturated methanolic ammonia solution (25 ml) with slight warming to aid dissolution of the starting material. Once in solution, the reaction was allowed to stir at room temperature for 20 hours. The solvent was removed under reduced pressure and the resulting residue purified by MPLC (Merck 9385 silica, 5% methanol in dichloromethane). The solvent was again removed to give the title compound as a white foam (255 mg, 43%).

$^1$H-NMR (300 MHz, DMSO-d6): δ=1.48 (s, 9H), 2.25–2.43 (m, 2H), 3.53 (m, 1H), 3.69 (m, 1H), 3.84 (dd, 1H), 3.95–4.27 (m, 7H), 4.56–4.70 (m, 1H), 4.97 (m, 1H), 5.84–5.92 (m, 1H), 7.35 (d, 2H), 9.54 (s, 1H). MS: ESP+ (M+H)+=536.

EXAMPLE 51

5(S)-Isoxazol-3-yl-aminomethyl)-3-(4-morpholinopheny)-oxazolidin-2-one

Reference Example 20, (400 mg, 0.90 mmol) was stirred in trifluoroacetic (5 ml) with warning to aid dissolution of the starting material. Once in solution, the reaction was allowed to stir at 60° C. for 15 minutes. The trifluoroacetic acid was removed under reduced pressure and the residue azeotroped with toluene. The residue was then taken into dichloromethane and washed with sat. NaHCO$_3$, water, sat. NaCl, and finally dried over MgSO$_4$. The solvent was removed under reduced pressure and the resulting solid triturated with ether to yield the title compound as an off-white solid (260 mg, 84%).

$^1$H-NMR (300 MHz, DMSO-d6): δ=3.06 (t, 4H), 3.42 (t, 2H), 3.70–3.83 (m, 5H), 4.10 (t, 1H), 4.81 (m, 1H), 6.0 (d, 1H), 6.55 (t, 1H), 6.97 (d, 2H), 7.40 (d, 2H), 8.40 (d, 1H).
MS: ESP+ (M+H)+=345.

The starting material was prepared as follows:

REFERENCE EXAMPLE 20

5(R)-(N-isoxazol-3-yl-N-tertbutoxycarbonyl)ami-nomethyl)-3-(4-morpholinophenyl)oxazolidin-2-one 5(R)-Hydroxymethyl-3-(4-morpholinophenyl)oxazoli-din-2-one (prepared by analogy to the 3-fluoro compound—see WO95/07271; 0.50 g, 1.80 mmol), 3-t-butyloxycarbo nylamino-isoxazole (0.50 g, 2.70 mmol), tri-n-butylphosphine (0.66 ml, 2.70 mmol), and 1,1'-(azodicarbonyl)-dipiperidine (0.68 g, 2.70 mmol) were reacted in anhydrous THF (30 ml) using the general method of Reference Example 15. The reaction was then purified by MPLC (Merck 9385 silica, 70% ethyl acetate in iso-hexane) and the solvent removed under reduced pressure to give a solid which was triturated with ether to give the title compound as an off-white solid.

$^1$H-NMR (300 MHz, DMSO-d6): δ=1.50 (s, 9H), 3.08 (t, 4H), 3.70–3.80 (m, 5H), 3.93–4.01 (m, 1H), 4.14–4.30 (m, 2H), 4.95 (m, 1H), 6.88 (s, 1H), 6.99 (d, 2H), 7.40 (d, 2H), 8.81 (s, 1H). MS: ESP+ (M+H)$^+$=445.

EXAMPLE 52

5(S)-Isoxazol-3-ylaminomethyl-3-(3,5-difluoro-(4-(1-(2(R,S)hydroxy-3-methylthiopropanoly)-1,2,5,6-tetrahydropyrid-4-yl)phenyl)oxazolidin-2-one Reference Example 21 (300 mg, 0.50 mM), was dissolved in trifluoroacetic acid (2 ml) and dichloromethane (2 ml) and stirred for 15 min. The TFA was removed by azeotroping with toluene and the resulting residue was purified by Bond elute (Merck 9385 silica, 60–100% EtOAc in hexane) to give the title compound as an off white solid (200 mg, 80%).

$^1$H-NMR (300 MHz, DMSO): δ=2.08 (s, 3H), 2.40 (m, 2H partially obscured by DMSO), 2.57, 2.79 (m, 2H Partially obscured by DMSO), 3.24 (t, 2H) 3.29–3.84 (m, 3H), 3.99–4.31 (m, 3H), 4.48 (m, 1H), 4.88 (m, 1H), 5.42 (m, 1H), 5.86 (s, 1H), 5.98 (s, 1H), 6.54 (t, 1H), 7.33 (d, 2H), 8.38 (s, 1H). MS: ESP$^+$ (M+H)$^+$=495.

The starting material was prepared as follows:

REFERENCE EXAMPLE 21

5(R)-isoxazol-3-yl-N-tertbutoxycarbonyl)aminomethyl-3-(3,5-difluoro-(4-(1-(2(R,S)-hydroxy-3-methylthiopropanoyl)-1,2,5,6-tetrahydropyrid yl)phenyl)oxazolidin-2-one Reference Example 10 (1.00 g, 2.10 mM), 2-hydroxy-3-(methylthio)propionic acid (0.23 g, 1.68 mM), 1-hydroxybenzotriazole (0.29 g, 2.18 mM), and N-methyl morpholine (0.22 g, 2.18 mM), were taken up in DMF (5 ml), and 1-(3-dimethylaminopropyl)-3-ethylcarbodiimide hydrochloride (0.42 g, 2.18 mM) was added. The resulting solution was stirred overnight. The DMF was removed by evaporation and the residue was taken up in dichloromethane, washed with water, dried (MgSO$_4$) and the solvent reduced by evaporation. This was purified by MPLC (Merck 9385 silica, 40–60% EtOAc in hexane) to give the title compound as a pale yellow solid after trituration with diethyl ether (310 mg, 27%).

$^1$H-NMR (300 MHz, DMSO): δ 1.48 (s, 9H), 2.18 (s, 3H), 2.39 (m, 2H partially obscured by DMSO), 2.57, 2.79 (m, 2H), 3.68–4.33 (m, 8H), 4.48 (m, 1H), 5.01 (m, 1H), 5.42 (dd, 1H), 5.88 (s, 1H), 6.84 (s, 1H), 7.32 (d, 2H), 8.79 (s, 1H). MS: ESP$^+$ (M+H)$^+$=595.

EXAMPLE 53

5(S)-(Isoxazol-3-ylaminomethyl)-3-(3,5-difluoro-(4-(1-(2(R,S)-hydroxy-3-methylsulfonylpropanoyl)-1,2,5,6-tetrahydropyrid-4-yl)phenyl)oxazolidin-2-one Example 52 (188 mg, 0.38 mM), was stirred in dichloromethane (10 ml) at 0° C., and 3-chloroperoxybenzoic acid (57–86%, 0.22 g, 0.76 mM), was added portionwise. The solution was stirred at 0° C. for 3 hr. Excess dichloromethane was added and this was washed with saturated NaHCO$_3$ solution, dried (MgSO$_4$) and the solvent removed by evaporation to give the title compound as a white powder after trituration with diethyl ether (60 mg, 30%).

H-NMR (300 MHz, DMSO): δ=2.31 (m, 2H partially obscured by DMSO), 3.04 (s, 3H), 3.41 (m, 4H partially obscured by water), 3.52–3.87 (m, 3H), 3.91–4.37 (m, 3H), 4.86 (m, 2H), 5.88 (s, 1H), 5.99 (s, 1H), 6.07 (d, 1H), 6.56 (t, 1H), 7.34 (d, 2H), 8.39 (s, 1H). MS: ESP$^+$ (M+H)$^+$=527.

EXAMPLE 54

5(S)(Isoxazol-3-yl-aminomethyl)-3-(3-fluoro-(4-(1-(2(R,S)-hydroxy-3-methylthiopropanoyl)-1,2,5,6-tetrahydropyrid-4-yl)phenyl)oxazolidin-2-one Reference Example 22 (290 mg, 050 mM), was dissolved in trifluoroacetic acid (2 ml) and dichloromethane (2 ml) and stirred for 15 min. The TFA was removed by azeotroping with toluene and the resulting residue was triturated to give the title compound as an off white solid (150 mg, 63%).

$^1$H-NMR (300 MHz, DMSO): δ=2.10 (s, 3H), 2.42 (m, 2H partially obscured by DMSO), 2.61, 2.81 (m, 2H Partially obscured by DMSO), 3.43 (t, 2H Partially obscured by water) 3.53–3.87 (m, 3H), 4.02–4.39 (m, 3H), 4.50 (m, 1H), 4.88 (quintet, 1H), 5.45 (broad, 1H) 5.88 (s, 1H), 6.02 (s, 1H), 6.56 (t, 1H), 7.24–7.56 (m, 3H), 8.37 (s, 1H). MS: ESP$^+$ (M+H)$^+$=477.

The starting material was prepared as follows:

REFERENCE EXAMPLE 22

5(R)-N-isoxazol-3-yl-N-tertbutoxycarbonyl)aminomethyl)-3-(3-fluoro-(4-(1-(2(R,S)-hydroxy-3-methylthiopropanoyl) 1,2,5,6-tetrahydropyrid-4-yl) phenyl)oxazolidin-2-one 5(R)-(N-isoxazol-3-yl-N-tertbutoxycarbonyl)aminomethyl)-3-(3-fluoro-4-(1,2,5,6-tetrahydropyrid-4-yl)phenyl) oxazolidin-2-one, hydrochloride (prepared in an analogous manner to Reference Example 10, but using 3-fluoro-substituted intermediates; 1.00 g, 2.02 mM), 2-hydroxy-3-(methylthio)propionic acid (0.22 g, 1.62 mM), 1-hydroxybenzotriazole (0.28 g, 2.10 mM), and N-methyl morpholine (0.22 g, 2.10 mM), were taken up in dichloromethane (5 ml), and 1-(3-dimethylaminopropyl)-3-ethylcarbodiimide hydrochloride (0.40 g, 2.10 mM) was added. The resulting solution was stirred overnight. Excess dichloromethane was added and this was washed with water, dried (MgSO$_4$) and the solvent reduced by evaporation. This was purified by MPLC (Merck 9385 silica, 40–60% EtOAc in hexane) to give the title compound as a pale yellow solid after trituration with diethyl ether (300 mg, 26%).

$^1$H-NMR (300 MHz, DMSO): δ=1.47 (s, 9H), 2.06 (s, 3H), 2.42 (m, 2H partially obscured by DMSO), 2.58, 2.79 (m, 2H), 3.48–4.32 (m, 8H), 4.48 (m, 1H), 4.99 (m, 1H), 5.39 (dd, 1H), 6.02 (s, 1H), 6.85 (s, 1H), 7.28–7.53 (m, 3H), 8.78 (s, 1H). MS: ESP+ (M+H)$^+$=577.

EXAMPLE 55

5(S)-(Isoxazol-3=yl-aminomethyl)-3-(3-fluoro-(4-(1-(2(R,S)-hydroxy-3-methylsulfonylpropanoyl)-1,2,5, 6-tetrahydropyridyl)phenyl)oxazolidin-2-one Example 54 (140 mg, 0.29 mM), was stirred in dichloromethane (10 ml), and 3-chloroperoxybenzoic acid (57–86%, 0.17 g, 0.76 mM), was added portionwise. The solution was stirred for 3 hr. Excess dichloromethane was added and this was washed with saturated NaHCO$_3$ solution, dried (MgSO$_4$) and the solvent removed by evaporation and purified by bondelute (Merk 9385 silica, 70–100% EtOAc in hexane) to give the title compound as a white powder after trituration with diethyl ether (56 mg, 27%).

H-NMR (300 MHz, DMSO): δ=2.41 (m, 2H partially obscured by DMSO), 3.02 (s, 3H), 3.41 (m, 4H partially obscured by water), 3.49–3.86 (m, 3H), 3.86–4.36 (m, 3H), 4.72–4.95 (m, 2H), 5.95–6.10 (m, 3H), 6.54 (t, 1H), 7.27–7.57 (m, 3H), 8.39 (s, 1H). MS: ESP$^+$ (M+H)$^+$=509.

EXAMPLE 56

5(S)-Isoxazol-3-ylaminomethyl-3-[3-fluoro-4-(1-(2-phosphorylacetyl-1,2,5,6-tetrahydropyrid-4-yl)phenyl]oxazolidin-2-one Trifluoroacetic acid (5.0 ml) was added dropwise at room temperature to a stirred solution of Reference Example 23 (250 mg, 0.41 mmol) in dichloromethane (5.0 ml). The resulting solution was stirred at room temperature for 10 min then evaporated to a pale yellow gum. Trituration with diethyl ether gave the title compound (200 mg, 98%) as a pale yellow solid.

$^1$H-NMR (300 MHz, DMSO-d6+CD$_3$COOD): δ=2.30–2.50 (m, 2H), 3.40 (d, 2H), 3.52 (t) & 3.61 (t) (2H), 3.76 (dd, 1H), 4.05 (m, 2H), 4.10 (t, 1H), 4.51 (t, 2H), 4.77–4.90 (m, 1H), 5.90–6.00 (m, 2H), 7.20–7.37 (m, 2H), 7.43 (d, 1H), 8.30 (d, 1H). MS: ESP$^+$ (M+H)$^+$=497.

The starting material was prepared as follows:

REFERENCE EXAMPLE 23

5(S)-Isoxazol-3-ylaminomethyl-3-(3-fluoro-4-(1-(2-t-butoxyphosphorylacetyl)-1,2,5,6-tetrahydropyrid-4-yl)phenyl)oxazolidin-2-one Di-tert-butyl N,N diethylphosphoramidite (503 mg, 1.88 mmol) was added dropwise at room temperature, under an atmosphere of nitrogen, to a stirred suspension of Example 5, (600 mg, 1.44 mmol) and 1H-tetrazole (303 mg, 4.33 mmol) in tetrahydrofuran (20 ml). The resulting mixture was stirred for 1 hr then a further 224 mg phosphoramidite was added and the reaction stirred for 1.5 hr. The reaction was then cooled to −40° C. and treated portionwise with 3-chloroperoxybenzoic acid (750 mg 70% strength, 3.0 mmol). The reaction was stirred at −40 to −20° C. for 1 hr then diluted with dichloromethane (60 ml), washed succesively with 10% aqueous sodium bisulfite solution, sat. sodium bicarbonate solution and water, dried over magnesium sulfate and evaporated to give a colourless oil. Purified by flash chromatography (Merck 9385 silica, 5% methanol/dichloromethane) to give the title compound (550 mg, 63%) as a colourless foam.

$^1$H-NMR (300 MHz, DMSO-d6): δ=1.42 (s, 18H), 2.40–2.60 (m, 2H), 3.44 (t, 2H), 3.57 (t) & 3.66 (t) (2H), 3.81 (dd, 1H), 4.10 (m, 2H), 4.16 (t, 1H), 4.60 (t, 2H), 4.83–4.95 (m, 1H), 5.95–6.05 (m, 2H), 6.56 (t, 1H), 7.27–7.44 (m, 2H), 7.50 (d, 1H), 8.38 (d, 1H).

EXAMPLE 57

5(S)-Isoxazol-3-yl-aminomethyl-3-(3,5-difluoro-4-(1-(2(S)-acetoxypropanoyl)-1,2,5,6-tetrahydropyrid-4-yl)phenyl)oxazolidin-2-one Trifluoroacetic acid (2.0 ml) was added dropwise at room temperature to a stirred solution of Reference Example 24 (167 mg, 0.28 mmol) in dichloromethane (2.0 ml). The resulting solution was stirred at room temperature for 30 min then evaporated to a colourless gum. Trituration with diethyl ether gave the title compound (114 mg, 82%) as a colourless solid.

$^1$H-NMR (300 MHz, DMSO-d6): δ=1.27–1.40 (m, 3H), 2.05 (s, 3H), 2.24–2.50 (m, 2H), 3.42 (m, 2H), 3.57–3.77 (m, 2H), 3.81 (dd, 1H), 3.95–4.10 (m, 1H), 4.10–4.30 (m, 2H), 4.84–4.96 (m, 1H), 5.32–5.50 (m, 1H), 5.87 (m, 1H), 6.00 (s, 1H), 6.56 (t, 1H), 7.34 (d, 2H), 8.40 (s, 1H). MS: ESP+ (M+H)$^+$=491.

The starting material was prepared as follows:

REFERENCE EXAMPLE 24

5(R)-(N-Isoxazol-3-yl-N-tertbutoxycarbonyl)-aminomethyl-3-(3,5-difluoro-4-(1-(2(S)-acetoxypropanoyl)-1,2,5,6-tetrahydropyrid-4-yl)phenyl)-oxazolidin-2-one (S)-2-Acetoxypropanoyl chloride (65 mg, 0.43 mmol) was added dropwise at room temperature to a stirred suspension of Reference Example 10 (200 mg, 0.39 mmol) and N,N diisopropyl ethylamine (106 mg, 0.82 mmol) in dichloromethane (10 ml). The reaction was stirred at room temperature for 2 hr then purified by flash chromatography (Merck 9385 silica, ethyl acetate/iso-hexane (7/3)) to give the title compound (177 mg, 77%) as a colourless solid.

$^1$H-NMR (300 MHz, CDCl$_3$): δ=1.45–1.52 (m, 3H), 1.57 (s, 9H), 2.14 (s, 3H), 2.42–2.62 (m, 2H), 3.69 (t, 2H), 3.80 (dd, 1H), 3.93–4.20 (m, 2H), 4.20–4.26 (m, 2H), 4.37 (dd, 1H), 5.04–5.16 (m, 1H), 5.37–5.55 (m, 1H), 5.81(m) & 5.89 (m) (1H), 6.90 (s(br), 1H), 7.16 (d, 2H), 8.27 (s, 1H). MS: ESP$^+$ (M+H)$^+$=591.

EXAMPLE 58

5(S)-Isoxazol-3-yl-aminomethyl-3-(3,5-difluoro-4(1-(2(S)-hydroxypropanoyl)-1,2,5,6-tetrahydropyrid-4-yl)phenyl)oxazolidin-2-one Example 57, (80 mg, 0.16 mmol) in 4.0 ml of a saturated solution of ammonia in methanol was stirred at room temperature for 18 hr then the resulting clear solution evaporated to a colourless gum. Trituration with diethyl ether gave the title compound (59 mg, 80%) as a colourless solid.

$^1$H-NMR (300 MHz, DMSO-d6): δ=1.20 (m, 3H), 2.20–2.45 (m, 2H), 3.40–3.65 (m, 2H), 3.72 (m, 2H), 3.82 (dd, 1H), 3.98–4.37 (m, 3H), 4.40–4.45 (m, 1H), 4.92 (m, 1H), 4.96(d) & 5.03 (d) (1H), 5.88 (m, 1H), 6.00 (s, 1H), 6.55(t, 1H), 7.33 (d, 2H), 8.40 (s, 1H). MS: ESP$^+$ (M+H)$^+$=449.

EXAMPLE 59

3-(4-(1-((2S)-2,3-Dihydroxypropanoyl)-1,2,5,6-tetrahydropyrid-4-yl)-3,5-difluorophenyl)-5(S)-(3-methylisothiazol-5-ylaminomethyl)oxazolidin-2 one Using essentially the technique of Example 20, but starting from 3-(4-(1-(2,2-dimethyl-1,3-dioxolan-4(S)-ylcarbonyl)-1,2,5,6-tetrahydropyridyl)-3,5-difluorophenyl)-5(R)-(N-(t-butoxycarbonyl)-3-methylisothiazol-5-ylaminomethyl)oxazolidin-2-one (250 mg, 0.39 mM), and using a gradient increasing in polarity from 0 to 20% methanol in dichloromethane for chromatography, gave the desired product (92 mg).

NMR (DMSO-$d_6$) δ: 2.16 (s, 3H); 2.29 (m, 1H); 2.37 (m, 1H); 3.42 (t, 2H); 3.47 (m, 1H); 3.55 (m, 1H); 3.73 (m, 1H); 3.76 (dd, 1H); 4.10 (m, 2H); 4.14 (t, 1H); 4.24 (m, 1H); 4.36 (t, 1H); 4.68 (t, 1H); 4.87 (m, 1H); 4.97 (m, 1H); 5.86 (s, 1H); 6.97 (s, 1H); 7.31 (d, 2H); 7.38 (t, 1H). MS (ESP): 495 (MH$^+$) for $C_{22}H_{24}F_2N_4O_5S$ The intermediates for this compound were prepared as follows:

3-(4-(1-(2,2-Dimethyl-1,3-dioxolan-4(S)-ylcarbonyl)-1,2,5,6-tetrahydropyrid-4-yl)-3,5-difluorophenyl)-5(R)-(N-(t-butoxycarbonyl)-3-methylisothiazol-5-ylaminomethyl)oxazolidin-2-one Essentially the technique of the relevant intermediate for Example 20 was used, but starting from 5-(t-butoxycarbonylamino)isothiazole (321 mg, 1.5 mM) as the amino component, gave the title product (221 mg). After chromatography on a 10 g silica Mega Bond Elut® column, the product was still impure, and was re-chromatographed by HPLC on a Hichrome 10×2.5 cm RPB column, eluting with a gradient from 0 to 100% acetonitrile in water containing 0.1% formic acid. Relevant fractions were combined to give the desired product (265 mg). MS (ESP): 635 (MH$^+$) for $C_{30}H_{36}F_2N_4O_7S$

5-(t-Butoxycarbonylamino)-3-methylisothiazole

Using essentially the technique of the relevant intermediate for Example 20, but starting from 3-methyl-5-aminoisothiazole hydrochloride (1.5 g, 10 mM) as the amino component, gave the title product (950 mg) after chromatography.

MS (ESP): 215 (MH$^+$) for $C_9H_{14}N_2O_2S$
NMR (DMSO-$d_6$): 1.46 (s, 9H); 2.23 (s, 3H); 6.50 (s, 1H); 11.07 (br, 1H).

EXAMPLE 60

3-(4-(1-(3-Hydroxypropanoyl)-1,2,5,6-tetrahydroyrid-4-yl)-3,5-difluorophenyl)-5(S)-(isoxazol-3-ylaminomethyl)oxazolidin-2-one 3-(4-(1-(3-Hydroxypropanoyl)-1,2,5,6-tetrahydropyrid 4-yl)-3,5-difluorophenyl)-5(R)-(N-(t-butoxycarbonyl)isoxazol-3-ylaminomethyl)oxazolidin-2-one (176 mg, 0.32 mM), was dissolved in dichloromethane (1 ml) and treated with trifluoroacetic acid (1 ml) at ambient temperature. After stirring for 10 minutes, the mixture was diluted with water (15 ml) and dichloromethane (15 ml), the organic layer separated, washed with water (2×15 ml), and dried (magnesium sulfate). Solvent was removed, and the residue triturated with diethyl ether to give the desired product (102 mg).

NMR (DMSO-$d_6$) δ: 2.20 (m, 1H); 2.28 (m, 1H); 2.48 (m overlapped by DMSO, 2H); 3.42 (br m overlapped by H$_2$O, ~4H); 3.55 (br m, ~3H); 3.83 (t, 1H); 4.01 (m, 1H); 4.06 (m, 2H); 4.81 (m, 1H); 5.78 (s, 1H); 5.92 (s, 1H); 6.47 (br s, 1H); 7.26 (d, 2H); 8.31 (s, 1H).

MS (ESP): 449 (MH$^+$) for $C_{21}H_{22}F_2N_4O_5$

The intermediate for this compound was prepared as follows:

3-(4-(1-(3-Hydroxypropanoyl)-1,2,5,6-tetrahydropyrid-4-yl)-3,5-difluorophenyl)-5(R)-(N-(t-butoxycarbonyl)isoxazol-3-ylaminomethyl)oxazolidin-2-one To a solution of 3-hydroxypropionic acid (45 mg, 0.5 mM) in N,N dimethylformamide (2 ml) was added 3-(4-(1, 2,5,6-tetrahydropyrid-4-yl)-3,5-difluorophenyl)-5(R)(N-(t-butoxy-carbonyl)isoxazol-3-ylaminomethyl)oxazolidin-2-one hydrochloride (256 mg, 0.5 mM, reference example 10), and O-benzotriazol-1-yl-N,N,N',N'-tetramethyluronium hexafluorophosphate (190 mg, 0.5 mM). The mixture was cooled to 0°, N,N-diisopropylethylamine (129 mg, 1 mM) added, and the mixture stirred 18 hours, allowing the temperature to rise to ambient. The mixture was poured into a mixture of ethyl acetate (40 ml) and water (40 ml), the organic layer separated and washed with aqueous sodium dihydrogen phosphate (2%, 40 ml), sodium bicarbonate (40 ml) and brine (40 ml). Solvent was removed, and the residue chromatographed on a 10 g silica Mega Bond Elut® column, eluting with a mixture of 2.5% methanol in dichloromethane. Relevant fractions were combined and evaporated to give the title product (203 mg).

NMR (DMSO-$d_6$) δ: 1.47 (s, 9H); 2.28 (m, 1H); 2.37 (m, 1H); 2.54 (m overlapped by DMSO, 2H); 3.66 (brm, 4H); 3.86 (dd, 1H); 3.95 (dd, 1H); 4.08 (m, 1H); 4.17 (m, 1H); 4.26 (dd, 2H); 4.53 (m, 1H); 5.02 (m, 1H); 5.87 (s, 1H); 6.86 (s, 1H); 7.33 (d, 2H); 8.82 (s, 1H). MS (ESP): 549 (MH$^+$) for $C_{26}H_{30}F_2N_4O_7$

EXAMPLE 61

The following illustrate representative pharmaceutical dosage forms containing a compound of the formula (I), an in-vivo hydrolysable ester or a pharmaceutically-acceptable salt thereof, including a pharmaceutically-acceptable salt of an in-vivo hydrolysable ester, (hereafter compound X), for therapeutic or prophylactic use in humans:

|  | mg/tablet |
|---|---|
| (a) Tablet I | |
| Compound X | 500 |
| Lactose Ph. Eur | 430 |
| Croscarmellose sodium | 40 |
| Polyvinylpyrrolidone | 20 |
| Magnesium stearate | 10 |
| (b) Tablet II | |
| Compound X | 100 |
| Lactose Ph. Eur | 179 |
| Croscarmellose sodium | 12 |
| Polyvinylpyrrolidone | 6 |
| Magnesium stearate | 3 |

-continued (c) Tablet III

| | |
|---|---|
| Compound X | 50 |
| Lactose Ph. Eur | 229 |
| Croscarmellose sodium | 12 |
| Polyvinylpyrrolidone | 6 |
| Magnesium stearate | 3 |

(d) Tablet IV

| | |
|---|---|
| Compound X | 1 |
| Lactose Ph. Eur | 92 |
| Croscarmellose sodium | 4 |
| Polyvinylpyrrolidone | 2 |
| Magnesium stearate | 1 |

| | mg/capsule |
|---|---|
| (e) Capsule | |
| Compound X | 10 |
| Lactose Ph. Eur | 389 |
| Croscarmellose sodium | 100 |
| Magnesium stearate | 1 |
| (f) Injection I | |
| Compound X | 50% w/v |
| Isotonic aqueous solution | to 100% |
| (g) Injection II (e.g. bolus) | |
| Compound X | 10% w/v |
| Isotonic aqueous solution | to 100% |
| (h) Injection III | |
| Compound X | 5% w/v |
| Isotonic aqueous solution | to 100% |
| (i) Injection IV (e.g. infusion) | |
| Compound X | 1% w/v |
| Isotonic aqueous solution | to 100% |

Buffers, pharmaceutically-acceptable surfactants, oils or cosolvents such as polyethylene glycol, polypropylene glycol, glycerol or ethanol, glidants (such as silicon dioxide) or complexing agents such as a cyclodextrin (for example, hydroxy-propyl β-cyclodextrin or sulfo-butyl-ether β-cyclodextrin) may be used to aid formulation. Also, improvements in aqueous solubility, if desired, may be achieved, for example, by conjugation of a compound of formula (I) with a phospholipid (such as a (phospho)choline derivative) to form a micellar emulsion.

Note: The above formulations may be obtained by conventional procedures well known in the pharmaceutical art, for example as described in "Remington: The Science & Practice of Pharmacy" Vols. I & II (Ed. A. R.-Gennaro (Chairman) et al; Publisher: Mack Publishing Company, Easton, Pa.; 19th Edition—1995) and "Pharmaceutics—The Science of Dosage Form Design" (Ed. M. E. Aulton; Publisher: Churchill Livingstone; first published 1988). The tablets (a)–(d) may be (polymer) coated by conventional means, for example to provide an enteric coating of cellulose acetate phthalate.

The invention claimed is:

1. A compound of formula (I), or a pharmaceutically acceptable salt, or an in-vivo hydrolysable ester thereof,

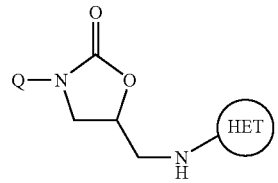

(I)

wherein
HET is a C-linked 5-membered heteroaryl ring containing 2 to 4 heteroatoms independently selected from N, O and S, which ring is optionally substituted on an available carbon atom by 1 or 2 substituents independently selected from (1–4C)alkyl, amino, (1–4C)alkylamino, (1–4C) alkoxy, (1–4C)alkoxycarbonyl and halogen, and/or on an available nitrogen atom (provided that the ring is not thereby quaternised) by (1–4C)alkyl; or HET is a C-linked 6-membered heteroaryl ring containing 2 or 3 nitrogen heteroatoms, which ring is optionally substituted on any available C atom by 1, 2 or 3 substituents independently selected from (1–4C)alkyl, amino, (1–4C)alkylamino, (1–4C)alkoxy, (1–4C) alkoxycarbonyl and halogen;

Q is Q3

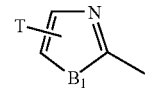

Q3 wherein $B_1$ is O or S wherein T is selected from the groups in (TA) to (TD) below (wherein AR1, AR2, AR2a, AR2b, AR3, AR3a, AR3b, AR4, AR4a, CY1 and CY2 are defined hereinbelow);

(TA) T is selected from the following groups (TAa) AR1, AR1-(1–4C)alkyl-, AR2 (carbon linked), AR3;

(TAb) AR1-CH(OH)—, AR2-CH(OH)—, AR3-CH(OH)—;

(TAc) AR1-CO—, AR2-CO—, AR3-CO—, AR4-CO—;

(TAd) AR1-O—, AR2-O—, AR3-O—;

(TAe) AR1-S(O)$_q$—, AR2-S(O)$_q$—, AR3-S(O)$_q$— (q is 0, 1 or 2);

(TAf) an optionally substituted N-linked (fully unsaturated) 5-membered heteroaryl ring system containing 1, 2 or 3 nitrogen atoms;

(TAg) a carbon linked tropol-3-one or tropol-4-one, optionally substituted in a position not adjacent to the linking position; or (TB) T is selected from the following groups:

(TBa) -(1–4C)alkyl {optionally substituted by one or more groups each independently selected from hydroxy, (1–4C)alkoxy, (1–4C)alkanoyl, cyano, halo, trifluoromethyl, (1–4C)alkoxycarbonyl, —NRvRw, (1–6C)alkanoylamino, (1–4C)alkoxycarbonylamino, N-(1–4C)alkyl-N-(1–6C)alkanoylamino, (1–4C)alkylS(O)$_q$— (q is 0, 1 or 2), CY1, CY2 or AR1;

(TBb) —NRv$^1$Rw$^1$;

(TBc) ethenyl, 2-(1–4C)alkylethenyl, 2-cyanoethenyl, 2-cyano-2-((1–4C)alkyl)ethenyl, 2-nitroethenyl, 2-nitro-2-((1–4C)alkyl)ethenyl, 2-((1–4C)alkylaminocarbonyl)ethenyl, 2-((1–4C)alkoxycarbonyl)ethenyl, 2-(AR1)ethenyl, 2-(AR2)ethenyl;

(TBd) $R^{10}CO$—, $R^{10}S(O)_q$— (q is 0, 1 or 2) or $R^{10}CS$— wherein $R^{10}$ is selected from the following groups:

(TBda) CY1 or CY2;

(TBdb) hydrogen, (1–4C)alkoxycarbonyl, trifluoromethyl, ethenyl, 2-(1–4C)alkylethenyl, 2-cyanoethenyl, 2-cyano-2-((1–4C)alkyl)ethenyl, 2-nitroethenyl, 2-nitro-2-((1–4C)alkyl)ethenyl, 2-((1–4C)alkylaminocarbonyl)ethenyl,2-((1–4C)alkoxycarbonyl)ethenyl, 2-(AR1)ethenyl or 2-(AR2)ethenyl; or (TBdc) (1–4C)alkyl {optionally substituted as defined in (TBa) above, or by (1–4C) alkylS(O)$_p$NH— or (1–4C) alkylS(O)$_p$-((1–4C)alkyl)N— (p is 1 or 2)};

wherein Rv is hydrogen or (1–4C)alkyl; Rw is hydrogen or (1–4C)alkyl; Rv$^1$ is hydrogen, (1–4C)alkyl or (3–8C)cycloalkyl; Rw$^1$ is hydrogen, (1–4C)alkyl, (3–8C)cycloalkyl, (1–4C)alkyl-CO— or (1–4C)alkylS(O)$_q$— (q is 1 or 2); or (TC) T is selected from the following groups:

(TCa) an optionally substituted, fully saturated 4-membered monocyclic ring containing 1 heteroatom selected from O, N and S (optionally oxidised), and linked via a ring nitrogen or sp$^3$ carbon atom;

(TCb) an optionally substituted 5-membered monocyclic ring containing 1 heteroatom selected from O, N and S (optionally oxidised), and linked via a ring nitrogen atom or a ring sp$^3$ or sp$^2$ carbon atom, which monocyclic ring is fully saturated other than (where appropriate) at a linking sp$^2$ carbon atom;

(TCc) an optionally substituted 6- or 7-membered monocyclic ring containing 1 or 2 heteroatoms independently selected from O, N and S (optionally oxidised), and linked via a ring nitrogen atom or a ring sp$^3$ or sp$^2$ carbon atom, which monocyclic ring is fully saturated other than (where appropriate) at a linking sp$^2$ carbon atom; or (TD) T is selected from the following groups:

(TDa) a bicyclic spiro-ring system containing 0, 1 or 2 ring nitrogen atoms as the only ring heteroatoms, the structure consisting of a 5- or 6-membered ring system (linked via a ring nitrogen atom or a ring sp$^3$ or sp$^2$ carbon atom) substituted (but not adjacent to the linking position) by a 3-, 4-, or 5-membered spiro-carbon-linked ring; which bicyclic ring system is (i) fully saturated other than (where appropriate) at a linking sp$^2$ carbon atom;

(ii) contains one —N(Rc)— group in the ring system (at least two carbon atoms away from the linking position when the link is via a nitrogen atom or an sp$^2$ carbon atom) or one —N(Rc)— group in an optional substituent (not adjacent to the linking position) and is (iii) optionally further substituted on an available ring carbon atom; or (TDb) a 7-, 8- or 9-membered bicyclic ring system (linked via a ring nitrogen atom or a ring sp$^3$ or sp carbon atom) containing 0, 1 or 2 ring nitrogen atoms (and optionally a further O or S ring heteroatom), the structure containing a bridge of 1, 2 or 3 carbon atoms; which bicyclic ring system is (i) fully saturated other than (where appropriate) at a linking sp$^2$ carbon atom;

(ii) contains one O or S heteroatom, or one —N(Rc)— group in the ring (at least two carbon atoms away from the linking position when the link is via a nitrogen atom or an sp$^2$ carbon atom) or one —N(Rc)— group in an optional substituent (not adjacent to the linking position) and is (iii) optionally further substituted on an available ring carbon atom;

wherein Rc is selected from groups (Rc1) to (Rc5):

(Rc1) (1–6C)alkyl {optionally substituted by one or more (1–4C)alkanoyl groups (including geminal disubstitution) and/or optionally monosubstituted by cyano, (1–4C)alkoxy, trifluoromethyl, (1–4C)alkoxycarbonyl, phenyl (optionally substituted by up to three substituents independently selected from (1–4C)alkyl {optionally substituted by one substituent selected independently from hydroxy, trifluoromethyl, (1–4C)alkylS(O)$_q$— (q is 0, 1 or 2), (1–4C)alkoxy, (1–4C)alkoxycarbonyl, cyano, nitro, (1–4C)alkanoylamino, —CONRvRw or —NRvRw}, trifluoromethyl, hydroxy, halo, nitro, cyano, thiol, (1–4C)alkoxy, (1–4C)alkanoyloxy, dimethylaminomethyleneaminocarbonyl, di(N-(1–4C)alkyl)aminomethylimino, carboxy, (1–4C)alkoxycarbonyl, (1–4C)alkanoyl, (1–4C)alkylSO$_2$amino, (2–4C)alkenyl {optionally substituted by carboxy or (1–4C)alkoxycarbonyl}, (2–4C)alkynyl, (1–4C)alkanoylamino, oxo(=O), thioxo (=S), (1–4C)alkanoylamino {the (1–4C)alkanoyl group being optionally substituted by hydroxy}, (1–4C)alkylS(O)$_q$— (q is 0, 1 or 2) {the (1–4C)alkyl group being optionally substituted by one or more groups independently selected from cyano, hydroxy and (1–4C)alkoxy}, —CONRvRw, —NRvRw, trifluoromethoxy, benzoylamino, benzoyl, phenyl {optionally substituted by up to three substituents independently selected from halo, (1–4C)alkoxy or cyano}, furan, pyrrole, pyrazole, imidazole, triazole, pyrimidine, pyridazine, pyridine, isoxazole, oxazole, isothiazole, thiazole, thiophene, hydroxyimino(1–4C)alkyl, (1–4C)alkoxyimino(1–4C)alkyl, halo-(1–4C)alkyl, (1–4C)alkanesulfonamido, —SO$_2$NRvRw (wherein Rv is hydrogen or (1–4C)alkyl; Rw is hydrogen or (1–4C)alkyl), (1–4C)alkylS(O)$_q$— (q is 0, 1 or 2); or, on any but the first carbon atom of the (1–6C)alkyl chain, optionally substituted by one or more groups (including geminal disubstitution) each independently selected from hydroxy and fluoro, and/or optionally monosubstituted by oxo, —NRvRw (wherein Rv is hydrogen or (1–4C)alkyl; Rw is hydrogen or (1–4C)alkyl), (1–6C)alkanoylamino, (1–4C)alkoxycarbonylamino, N-(1–4C)alkyl-N-(1–6C)alkanoylamino, (1–4C)alkylS(O)$_p$NH— or (1–4C)alkylS(O)$_p$-((1–4C)alkyl)N— (p is 1 or 2)};

(Rc2) $R^{13}CO$—, $R^{13}SO_2$— or $R^{13}CS$— wherein $R^{13}$ is selected from (Rc2a) to (Rc2e):

(Rc2a) AR1, AR2, AR2a, AR2b, AR3, AR3a, AR3b, AR4, AR4a, CY1, CY2;

(Rc2b) hydrogen, (1–4C)alkoxycarbonyl, trifluoromethyl, —NRvRw (wherein Rv is hydrogen or (1–4C)alkyl; Rw is hydrogen or (1–4C)alkyl), ethenyl, 2-(1–4C)alkylethenyl, 2-cyanoethenyl, 2-cyano-2-((1–4C)alkyl)ethenyl-2-nitroethenyl, 2-nitro-2-((1–4C)alkyl)ethenyl, 2-((1–4C)alkylaminocarbonyl)ethenyl, 2-((1–4C)alkoxycarbonyl)ethenyl, 2(AR1)ethenyl, 2-(AR2)ethenyl, 2-(AR2a)ethenyl;

(Rc2c) (1–10C)alkyl {optionally substituted by one or more groups (including geminal disubstitution) each independently selected from hydroxy, (1–10C)alkoxy, (1–4C)alkoxy-(1–4C)alkoxy, (1–4C)alkoxy-(1–4C)

alkoxy-(1–4C)alkoxy, (1–4C)alkanoyl, phosphoryl (—O—P(O)(OH)$_2$, and mono- and di-(1–4C)alkoxy derivatives thereof), phosphiryl (—O—P(OH)$_2$ and mono- and di-(1–4C)alkoxy derivatives thereof), and amino; and/or optionally substituted by one group selected from carboxy, phosphonate (phosphono, —P(O)(OH)$_2$, and mono- and di-(1–4C)alkoxy derivatives thereof), phosphinate (—P(OH)$_2$ and mono- and di-(1–4C)alkoxy derivatives thereof), cyano, halo, trifluoromethyl, (1–4C)alkoxycarbonyl, (1–4C)alkoxy-(1–4C)alkoxycarbonyl, (1–4C)alkoxy-(1–4C)alkoxy-(1–4C)alkoxycarbonyl, (1–4C)alkylamino, di((1–4C)alkyl)amino, (1–6C)alkanoylamino, (1–4C)alkoxycarbonylamino, N-(1–4C)alkyl-N-(1–6C)alkanoylamino, (1–4C)alkylaminocarbonyl, di((1–4C)alkyl)aminocarbonyl, (1–4C)alkylS(O)$_p$NH—, (1–4C)alkylS(O)$_p$-((1–4C)alkyl)N—, fluoro(1–4C)alkylS(O)$_p$NH—, fluoro(1–4C)alkylS(O)$_p$((1–4C)alkyl)N—, (1–4C)alkylS(O)$_q$— (the (1–4C)alkyl group of (1–4C)alkylS(O)$_q$-being optionally substituted by one substituent selected from hydroxy, (1–4C)alkoxy, (1–4C)alkanoyl, phosphoryl (—O—P(O)(OH)$_2$, and mono- and di-(1–4C)alkoxy derivatives thereof), phosphiryl (—O—P(OH)$_2$ and mono- and di-(1–4C)alkoxy derivatives thereof), amino, cyano, halo, trifluoromethyl, (1–4C)alkoxycarbonyl, (1–4C)alkoxy-(1–4C)alkoxycarbonyl, (1–4C)alkoxy-(1–4C)alkoxy-(1–4C)alkoxycarbonyl, carboxy, (1–4C)alkylamino, di((1–4C)alkyl)amino, (1–6C)alkanoylamino, (1–4C)alkoxycarbonylamino, N-(1–4C)alkyl-N-(1–6C)alkanoylamino, (1–4C)alkylaminocarbonyl, di((1–4C)alkyl)aminocarbonyl, (1–4C)alkylS(O)$_p$NH—, (1–4C)alkylS(O)$_p$-((1–4C)alkyl)N—, (1–4C)alkylS(O)$_q$—, AR1-S(O)$_q$—, AR2-S(O)$_q$—, AR3-S(O)$_q$— and also AR2a, AR2b, AR3a and AR3b versions of AR2 and AR3 containing groups), CY1, CY2, AR1, AR2, AR3, AR1-O—, AR2-O—, AR3-O—, AR1-S(O)$_q$—, AR2-S(O)$_q$—, AR3-S(O)$_q$—, AR1-NH—, AR2-NH—, AR3-NH— (p is 1 or 2 and q is 0, 1 or 2), and also AR2a, AR2b, AR3a and AR3b versions of AR2 and AR3 containing groups};

(Rc2d) R$^{14}$C(O)O(1–6C)alkyl wherein R$^{14}$ is AR1, AR2, (1–4C)alkylamino (the (1–4C)alkyl group being optionally substituted by (1–4C)alkoxycarbonyl or by carboxy), benzyloxy-(1–4C)alkyl or (1–10C)alkyl {optionally substituted as defined for (Rc2c)};

(Rc2e) R$^{15}$O— wherein R$^{15}$ is benzyl, (1–6C)alkyl {optionally substituted as defined for (Rc2c)}, CY1, CY2 or AR2b;

(Rc3) hydrogen, cyano, 2-cyanoethenyl, 2-cyano-2-((1–4C)alkyl)ethenyl, 2-((1–4C) alkylaminocarbonyl)ethenyl, 2-((1–4C)alkoxycarbonyl)ethenyl, 2-nitroethenyl, 2-nitro-2-((1–4C)alkyl)ethenyl, 2-(AR1)ethenyl, 2-(AR2)ethenyl, or of the formula (Rc3a)

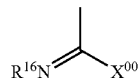

(Rc3a)

wherein X$^{00}$ is —OR$^{17}$, —SR$^{17}$, NHR$^{17}$ and —N(R$^{17}$)$_2$;
wherein R$^{17}$ is hydrogen (when X$^{00}$ is —NHR$^{17}$ and —N(R$^{17}$)$_2$), and R$^{17}$ is (1–4C)alkyl, phenyl or AR2 (when X$^{00}$ is —OR$^{17}$, —SR$^{17}$ and —NHR$^{17}$); and R$^{16}$ is cyano, nitro, (1–4C)alkylsulfonyl, (4–7C)cycloalkylsulfonyl, phenylsulfonyl, (1–4C)alkanoyl and (1–4C) alkoxycarbonyl;

(Rc4) trityl, AR1, AR2, AR2a, AR2b, AR3, AR3a, AR3b;
(Rc5) RdOC(Re)=CH(C=O)—, RfC(=O)C(=O)—, RgN=C(Rh)C(=O)— or RiNHC(Rj)=CHC(=O)— wherein Rd is (1–6C)alkyl; Re is hydrogen or (1–6C)alkyl, or Rd and Re together form a (3–4C)alkylene chain; Rf is hydrogen, (1–6C)alkyl, hydroxy(1–6C)alkyl, (1–6C)alkoxy(1–6C)alkyl, —NRvRw (wherein Rv is hydrogen or (1–4C)alkyl; Rw is hydrogen or (1–4C)alkyl), (1–6C)alkoxy, (1–6C)alkoxy(1–6C)alkoxy, hydroxy(2–6C)alkoxy, (1–4C)alkylamino (2–6C)alkoxy, di-(1–4C)alkylamino(2–6C)alkoxy; Rh is (1–6C)alkyl, hydroxy or (1–6C)alkoxy; Rh is hydrogen or (1–6C)alkyl; Ri is hydrogen, (1–6C)alkyl, AR1, AR2, AR2a, AR2b and Rj is hydrogen or (1–6C)alkyl;
wherein
AR1 is an optionally substituted phenyl or optionally substituted naphthyl;
AR2 is an optionally substituted 5- or 6-membered, fully unsaturated (i.e. with the maximum degree of unsaturation) monocyclic heteroaryl ring containing up to four heteroatoms independently selected from O, N and S (but not containing any O—O, O—S or S—S bonds), and linked via a ring carbon atom, or a ring nitrogen atom if the ring is not thereby quaternised;
AR2a is a partially hydrogenated version of AR2 (i.e. AR2 systems retaining some, but not the full, degree of unsaturation), linked via a ring carbon atom or linked via a ring nitrogen atom if the ring is not thereby quaternised;
AR2b is a fully hydrogenated version of AR2 (i.e. AR2 systems having no unsaturation), linked via a ring carbon atom or linked via a ring nitrogen atom;
AR3 is an optionally substituted 8-, 9- or 10-membered, fully unsaturated (i.e. with the maximum degree of unsaturation) bicyclic heteroaryl ring containing up to four heteroatoms independently selected from O, N and S (but not containing any O—O, O—S or S—S bonds), and linked via a ring carbon atom in either of the rings comprising the bicyclic system;
AR3a is a partially hydrogenated version of AR3 (i.e. AR3 systems retaining some, but not the full, degree of unsaturation), linked via a ring carbon atom, or linked via a ring nitrogen atom if the ring is not thereby quaternised, in either of the rings comprising the bicyclic system;
AR3b is a fully hydrogenated version of AR3 (i.e. AR3 systems having no unsaturation), linked via a ring carbon atom, or linked via a ring nitrogen atom, in either of the rings comprising the bicyclic system;
AR4 is an optionally substituted 13- or 14-membered, fully unsaturated (i.e. with the maximum degree of unsaturation) tricyclic heteroaryl ring containing up to four heteroatoms independently selected from O, N and S (but not containing any O—O, O—S or S—S bonds), and linked via a ring carbon atom in any of the rings comprising the tricyclic system;
AR4a is a partially hydrogenated version of AR4 (i.e. AR4 systems retaining some, but not the full, degree of unsaturation), linked via a ring carbon atom, or linked via a ring nitrogen atom if the ring is not thereby quaternised, in any of the rings comprising the tricyclic system;
CY1 is an optionally substituted cyclobutyl, cyclopentyl or cyclohexyl ring;

CY2 is an optionally substituted cyclopentenyl or cyclohexenyl ring.

2. A compound of the formula (I), or a pharmaceutically acceptable salt, or an in-vivo hydrolysable ester thereof, as claimed in claim 1 wherein T is an optionally substituted N-linked (fully unsaturated) 5-membered heteroaryl ring system containing 1, 2 or 3 nitrogen atoms (group (TAf)) selected from a group of formula (TAf1) to (TAf6):

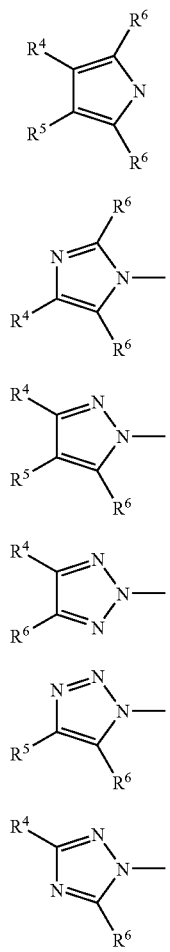

TAf1

TAf2

TAf3

TAf4

TAf5

TAf6 wherein:
R$^6$ is selected (independently where appropriate) from hydrogen, (1–4C)alkyl, (1–4C)alkoxycarbonyl, (1–4C)alkanoyl, carbamoyl and cyano;

R$^4$ and R$^5$ are independently selected from hydrogen, halo, trifluoromethyl, cyano, nitro, (1–4C)alkoxy, (1–4C)alkylS(O)$_q$— (q is 0, 1 or 2), (1–4C)alkanoyl, (1–4C)alkoxycarbonyl, (2–4C)alkanoyloxy-(1–4C)alkyl, benzoxy-(1–4C)alkyl, (2–4C)alkanoylamino, —CONRvRw, —NRvRw and (1–4C)alkyl {optionally substituted by hydroxy, trifluoromethyl, cyano, nitro, (1–4C)alkoxy, (1–4C)alkylS(O)$_q$— (q is 0, 1 or 2), (1–4C)alkoxycarbonyl, (1–4C)alkanoylamino, —CONRvRw, —NRvRw; wherein Rv is hydrogen or (1–4C)alkyl; Rw is hydrogen or (1–4C)alkyl};

or R$^4$ is selected from one of the groups in (TAfa) to (TAfc) below, or (where appropriate) one of R$^4$ and R$^5$ is selected from the above list of R$^4$ and R$^5$ values, and the other is selected from one of the groups in (TAfa) to (TAfc) below:

(TAfa) a group of the formula (TAfa1)

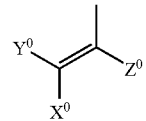

wherein Z$^0$ is hydrogen or (1–4C)alkyl;

X$^0$ and Y$^0$ are independently selected from hydrogen, (1–4C)alkyl, (1–4C)alkoxycarbonyl, halo, cyano, nitro, (1–4C)alkylS(O)$_q$— (q is 0, 1 or 2), RvRwNSO$_2$—, trifluoromethyl, pentafluoroethyl, (1–4C)alkanoyl and —CONRvRw (wherein Rv is hydrogen or (1–4C)alkyl; Rw is hydrogen or (1–4C)alkyl); or one of X$^0$ and Y$^0$ is selected from the above list of X$^0$ and Y$^0$ values, and the other is selected from phenyl, phenylcarbonyl, —S(O)$_q$-phenyl (q is 0, 1 or 2), N-(phenyl)carbamoyl, phenylaminosulfonyl, AR2, (AR2)-CO—, (AR2)-S(O)$_q$— (q is 0, 1 or 2), N-(AR2)carbamoyl and (AR2)aminosulfonyl; wherein any phenyl group in (TAfa) may be optionally substituted by up to three substituents independently selected from (1–4C)alkyl, cyano, trifluoromethyl, nitro, halo and (1–4C)alkylsulfonyl;

(TAfb) an acetylene of the formula —≡—H or -≡-(1–4C)alkyl;

(Tafc) —X$^1$—Y$^1$—AR2, —X$^1$—Y$^1$—AR2a, —X$^1$—Y$^1$—AR2b, —X$^1$—Y$^1$—AR3, —X$^1$—Y$^1$—AR3a or —X$^1$—Y$^1$—AR3b;

wherein X$^1$ is a direct bond or —CH(OH)— and

Y$^1$ is —(CH$_2$)$_m$—, —(CH$_2$)$_n$—NH—(CH$_2$)$_m$—, —CO—(CH$_2$)$_m$—, —CONH—(CH$_2$)$_m$—, —C(=S)NH—(CH$_2$)$_m$— or —C(=O)O—(CH$_2$)$_m$—;

or wherein X$^1$ is —(CH$_2$)$_n$— or —CH(Me)—(CH$_2$)$_m$— and

Y$^1$ is —(CH$_2$)$_m$—NH—(CH$_2$)$_m$—, —CO—(CH$_2$)$_m$—, —CONH—(CH$_2$)$_m$—, C(=S)NH—(CH$_2$)$_m$—, C(=O)O—(CH$_2$)$_m$— or —S(O)$_q$—(CH$_2$)$_m$—;

or wherein X$^1$ is —CH$_2$O—, —CH$_2$NH— or —CH$_2$N((1–4C)alkyl)- and

Y$^1$ is —CO—(CH$_2$)$_m$—, —CONH—(CH$_2$)$_m$— or —C(=S)NH—(CH$_2$)$_m$—; and additionally Y$^1$ is —SO$_2$— when X$^1$ is —CH$_2$NH— or —CH$_2$N((1–4C)alkyl)-, and Y$^1$ is —(CH$_2$)$_m$— when X$^1$ is —CH$_2$O— or —CH$_2$N((1–4C)alkyl)-; wherein n is 1, 2 or 3; m is 0, 1, 2 or 3 and q is 0, 1 or 2; and when Y$^1$ is —(CH$_2$)$_m$—NH—(CH$_2$)$_m$— each m is independently selected from 0, 1, 2 or 3.

3. A compound of the formula (I), or a pharmaceutically acceptable salt, or an in-vivo hydrolysable ester thereof, as claimed in claim 1 wherein T is a 7-, 8- or 9-membered bicyclic ring system containing a bridge of 1, 2 or 3 carbon atoms (group (TDb)) selected from a group defined by the ring skeletons shown in formulae (TDb1) to (TDb14):

7-membered ring skeletons

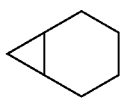
[4,1,0]

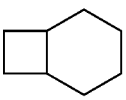
[3,2,0]

[3,1,1]

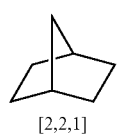
[2,2,1]

8-membered ring skeletons

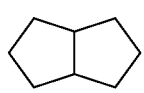
[3,3,0]

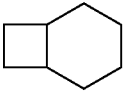
[4,2,0]

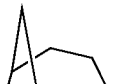
[4,1,1]

[3,2,1]

[2,2,2]

9-membered ring skeletons

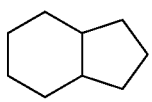
[4,3,0]

-continued (TDb1)

(TDb2)

(TDb3)

(TDb4)

(TDb5)

(TDb6)

(TDb7)

(TDb8)

(TDb9)

(TDb10)

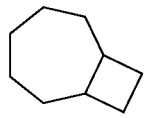
[5,2,0]   (TDb11)

[4,2,1]   (TDb12)

[3,3,1]   (TDb13)

[3,2,2]   (TDb14)

wherein;

(i) the ring system contains 0, 1 or 2 ring nitrogen atoms (and optionally a further O or S ring heteroatom), and when present the ring nitrogen, O or S heteroatom/s are at any position other than as part of the 3-membered ring in (TDb1);

(ii) the ring system is linked via a ring nitrogen atom or a ring sp$^3$ or sp$^2$ carbon atom (with the double bond, where appropriate, orientated in either direction) from any position in either ring (other than from a bridgehead position or from an sp$^2$ carbon atom in the 4-membered ring in (TDb2), (TDb6) and (TDb11));

(iii) one of the ring carbon atoms at a position not adjacent to the linking position, is replaced (other than when the ring contains an O or S heteroatom) by one of the following groups —NRc— (not at a bridgehead position), >C(H)—NHRc, >C(H)—NRc-(1–4C)alkyl, >C(H)—CH$_2$—NHRc, >C(H)—CH$_2$—NRc-(1–4C)alkyl (wherein the hydrogen atom shown in brackets is not present when the replacement is made at a bridgehead position and wherein a central —CH$_2$-chain link is optionally mono- or di-substituted by (1–4C)alkyl); with the proviso that when the ring system is linked via a ring nitrogen atom or an sp$^2$ carbon atom any replacement of a ring carbon atom by —NRc—, O or S is at least two carbon atoms away from the linking position; and (iv) the ring system is optionally (further) substituted on an available ring carbon atom as for the bicyclic spiro-ring systems described in (TDa); wherein Rc is as defined in claim 1.

4. A compound of the formula (I), or a pharmaceutically acceptable salt, or an in-vivo hydrolysable ester thereof, as claimed in claim 1 wherein T is (TC) (groups (TCa) to (TCc)) and is defined by formulae (TC1) to (TC4):

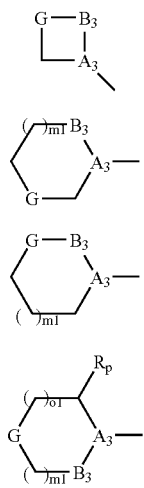

(TC1)

(TC2)

(TC3)

(TC4)

wherein in (TC1): >A₃—B₃— is >C(Rq)—CH(Rr)— and G is —O—, —S—, —SO—, —SO₂— or >N(Rc);

wherein in (TC2): m1 is 0, 1 or 2; >A₃—B₃— is >C=C(Rr)— or >C(Rq)—CH(Rr)— and G is —O—, —S—, —SO—, —SO₂— or >N(Rc);

wherein in (TC3): m1 is 0, 1 or 2; >A₃—B₃— is >C(Rq)—CH(Rr)— (other than when Rq and Rr are both together hydrogen) and G is —O—, —S—, —SO—, —SO₂— or >N(Rc);

wherein in (TC4): n1 is 1 or 2; o1 is 1 or 2 and n1+o1=2 or 3; >A₃—B₃— is >C=C(Rr)— or >C(Rq)—CH(Rr)— or >N—CH₂— and G is —O—, —S—, —SO—, —SO₂— or >N(Rc); Rp is hydrogen, (1–4C) alkyl (other than when such substitution is defined by >A₃—B₃—), hydroxy, (1–4C)alkoxy or (1–4C)alkanoyloxy;

wherein in (TC1), (TC2) and (TC4); m1, n1 and o1 are as defined hereinbefore: >A₃—B₃— is >N—CH₂— and G is >C(R¹¹)(R¹²), >C=O, >C—OH, >C-(1–4C)alkoxy, >C=N—OH, >C=N-(1–4C)alkoxy, >C=N—NH-(1–4C)alkyl, >C=N—N((1–4C)alkyl)₂ (the last two (1–4C)alkyl groups above in G being optionally substituted by hydroxy) or >C=N—N—CO-(1–4C)alkoxy;

wherein > represents two single bonds;

Rq is hydrogen, hydroxy, halo, (114C)alkyl or (114C)alkanoyloxy;

Rr is (independently where appropriate) hydrogen or (1–4C)alkyl;

R¹¹ is hydrogen, (1–4C)alkyl, fluoro(1–4C)alkyl, (1–4C)alkyl-thio-(1–4C)alkyl or hydroxy-(1–4C)alkyl and R¹² is —(C(Rr)(Rr))ₘ₂—N(Rr)(Rc) wherein m2 is 0, 1 or 2;

and, other than the ring substitution defined by G, >A₃—B₃— and Rp, each ring system may be optionally further substituted on a carbon atom not adjacent to the link at >A₃— by up to two substituents independently selected from (1–4C)alkyl, fluoro(1–4C)alkyl (including trifluoromethyl), (1–4C)alkyl-thio-(1–4C)alkyl, hydroxy-(1–4C)alkyl, amino, amino-(1–4C)alkyl, (1–4C)alkanoylamino, (1–4C)alkanoylamino-(1–4C)alkyl, carboxy, (1–4C)alkoxycarbonyl, AR-oxymethyl, AR-thiomethyl, oxo (=O) (other than when G is >N—Rc and Rc is group (Rc2) defined in claim 1) or independently selected from Rc; and also hydroxy or halo (the last two optional substituents only when G is —O— or —S—);

wherein AR is optionally substituted phenyl, optionally substituted phenyl(1–4C)alkyl, optionally substituted naphthyl, optionally substituted 5- or 6-membered heteroaryl;

optionally substituted 5/6 or 6/6 bicyclic heteroaryl ring system, in which the bicyclic heteroaryl ring systems may be linked via an atom in either of the rings comprising the bicyclic system, and wherein both the mono- and bicyclic heteroaryl ring systems are linked via a ring carbon atom and may be (partially) hydrogenated; and wherein Rc is as defined in claim 1.

5. A compound of the formula (I), or a pharmaceutically acceptable salt, or an in-vivo hydrolysable ester thereof, as claimed in claim 1, wherein T is (in the groups in (TCa) to (TCc)) defined by formulae (TC5) to (TC¹¹):

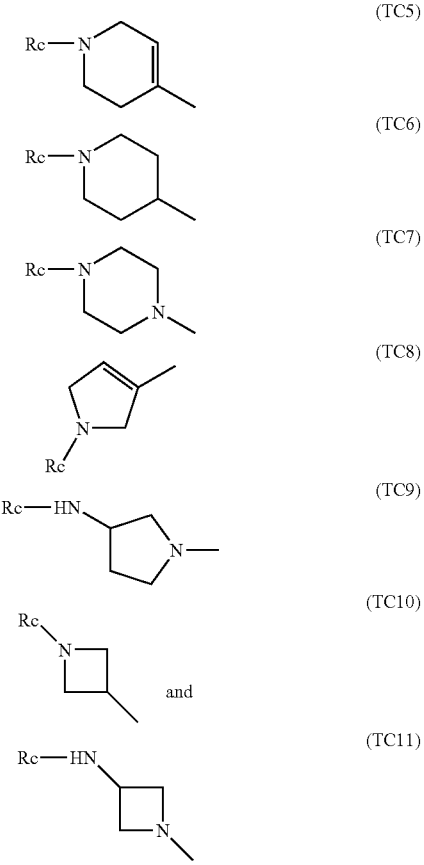

wherein Rc is as defined in claim 1.

6. A pharmaceutical composition which comprises a compound of claim 1, or a pharmaceutically acceptable salt or an in-vivo hydrolysable ester thereof, and a pharmaceutically acceptable diluent or carrier.

7. A pharmaceutical preparation comprising a pharmaceutically acceptable excipient and a compound of claim 1 or a pharmaceutically acceptable salt or in-vivo hydrolysable ester thereof.

* * * * *